(12) United States Patent
Nakamura et al.

(10) Patent No.: US 12,042,176 B2
(45) Date of Patent: Jul. 23, 2024

(54) PUNCTURING INSTRUMENT AND PUNCTURING DEVICE

(71) Applicant: TRANSELL Co., Ltd., Tokyo (JP)

(72) Inventors: Shuji Nakamura, Kanagawa (JP); Ken Masamune, Tokyo (JP); Kohei Miki, Tokyo (JP); Katsuyuki Sado, Tokyo (JP); Hirokazu Takagawa, Gunma (JP); Fumiya Iwashima, Gunma (JP); Akihiro Nabeshima, Tokushima (JP)

(73) Assignee: TRANSELL Co., Ltd., Tokyo (JP)

( * ) Notice: Subject to any disclaimer, the term of this patent is extended or adjusted under 35 U.S.C. 154(b) by 228 days.

(21) Appl. No.: 17/851,877

(22) Filed: Jun. 28, 2022

(65) Prior Publication Data

US 2023/0015695 A1    Jan. 19, 2023

Related U.S. Application Data

(62) Division of application No. 16/480,975, filed as application No. PCT/JP2018/003178 on Jan. 31, 2018, now Pat. No. 11,478,273.

(30) Foreign Application Priority Data

| Jan. 31, 2017 | (JP) | 2017-015764 |
| Jan. 31, 2017 | (JP) | 2017-015767 |
| Jan. 31, 2017 | (JP) | 2017-015795 |

(51) Int. Cl.
    *A61B 17/34* (2006.01)
    *A61B 10/02* (2006.01)
    (Continued)

(52) U.S. Cl.
    CPC ........ *A61B 17/3472* (2013.01); *A61B 10/025* (2013.01); *A61B 17/32* (2013.01);
    (Continued)

(58) Field of Classification Search
    CPC .................................................. A61B 17/3472
    See application file for complete search history.

(56) References Cited

U.S. PATENT DOCUMENTS 4,969,870 A * 11/1990 Kramer ............... A61B 10/025
                                                   604/93.01
5,556,399 A    9/1996 Huebner
(Continued)

FOREIGN PATENT DOCUMENTS

| JP | 3042299 | 5/2000 |
| JP | 2002-537007 | 11/2002 |

(Continued)

OTHER PUBLICATIONS

International Search Report issued in International Application No. PCT/JP2018/003178, May 1, 2018, 3 pages.
(Continued)

*Primary Examiner* — Christian A Sevilla
(74) *Attorney, Agent, or Firm* — HSML P.C.

(57) ABSTRACT

The present invention provide a puncture instrument capable of administering (supplying) a drug solution. The puncture instrument includes a puncture tip section (2); a first tubular body (3) connected to the puncture tip section (2) at the distal end; and an outer tubular body (5) at least partially covering the first tubular body (3). The first tubular body (3) is formed to be rotatable around an axis along the longitudinal direction. The first tubular body (3) has an outer diameter smaller than an inner diameter of the outer tubular body (5). A drug solution supply path (5a) is provided on the outside of the first tubular body (3).

12 Claims, 22 Drawing Sheets

(51) Int. Cl.
  *A61B 17/32* (2006.01)
  *A61M 1/00* (2006.01)
  *A61M 5/145* (2006.01)
  *A61M 5/158* (2006.01)
  *A61M 25/00* (2006.01)

(52) U.S. Cl.
  CPC ........... *A61B 17/3421* (2013.01); *A61M 1/60* (2021.05); *A61M 1/77* (2021.05); *A61M 5/1452* (2013.01); *A61M 5/1582* (2013.01); *A61B 2010/0258* (2013.01); *A61M 2025/0004* (2013.01); *A61M 2202/10* (2013.01); *A61M 2210/02* (2013.01)

(56) References Cited

U.S. PATENT DOCUMENTS

| | | | |
|---|---|---|---|
| 5,954,671 | A | 9/1999 | O'Neill |
| 6,478,751 | B1 | 11/2002 | Krueger et al. |
| 2002/0058945 | A1* | 5/2002 | Steiner ............... A61B 17/1635 606/80 |
| 2003/0078586 | A1 | 4/2003 | Shapira |
| 2003/0225364 | A1 | 12/2003 | Kraft et al. |
| 2004/0068267 | A1* | 4/2004 | Harvie ............... A61B 17/8836 606/92 |
| 2004/0191897 | A1 | 9/2004 | Muschler |
| 2007/0276352 | A1 | 11/2007 | Crocker et al. |
| 2008/0215056 | A1* | 9/2008 | Miller ............... A61B 17/32002 606/80 |
| 2008/0221580 | A1* | 9/2008 | Miller ............... A61B 17/1622 606/80 |
| 2009/0131827 | A1 | 5/2009 | Crocker et al. |
| 2010/0030105 | A1* | 2/2010 | Noishiki ............... A61B 10/025 600/567 |
| 2010/0286714 | A1 | 11/2010 | Gyrn et al. |
| 2010/0324506 | A1* | 12/2010 | Pellegrino .......... A61B 18/1492 604/528 |
| 2011/0152866 | A1* | 6/2011 | Knutson ............ A61B 17/3472 606/86 R |
| 2014/0148808 | A1 | 5/2014 | Inkpen et al. |
| 2015/0342756 | A1 | 12/2015 | Bays et al. |
| 2016/0346003 | A1 | 12/2016 | Grothe et al. |
| 2016/0354162 | A1 | 12/2016 | Yen et al. |

FOREIGN PATENT DOCUMENTS

| | | |
|---|---|---|
| JP | 2010-533525 | 10/2010 |
| JP | 4808961 | 11/2011 |
| JP | 2014-512876 | 5/2014 |
| JP | 2016-154599 | 9/2016 |

OTHER PUBLICATIONS

Extended European Search Report issued corresponding European Patent Application No. 18747412.7, Oct. 29, 2020, 6 pages.
Extended European Search Report issued in corresponding European Patent Application No. 21162001.8, May 31, 2021, 6 pages.
Office Action issued in corresponding Australian Patent Application No. 2020203807, Jun. 8, 2021, 8 pages.
Office Action issued in corresponding Korean Patent Application No. 10-2021-7009621, Jun. 23, 2021, 11 pages w/ translation.
Examination Report issued in corresponding Australian Patent Application No. 2020203807, Sep. 24, 2021, 4 pages.

* cited by examiner

PUNCTURING INSTRUMENT AND PUNCTURING DEVICE

TECHNICAL FIELD

The present invention relates to a puncture instrument and a puncture device.

BACKGROUND ART

Conventionally, a needle for manually puncturing the ilium with a bone marrow puncture needle to collect a bone marrow fluid has been used. In this kind of device, the bone marrow puncture needle is configured by inserting an inner needle into a guide tube and causing the tip of the inner needle to project from the guide tube. In recent years, for example, as described in the Patent Literature 1, a device where a drill blade is formed at the tip of the inner needle, and the inner needle is rotated by an electric drill to perform perforation (puncturing) in a short time has been proposed. However, in any of this kind of bone marrow puncture needle, a large amount of bone marrow fluid containing peripheral blood is required to obtain a sufficient amount of bone marrow hematopoietic stem cells, and stem cells have not been efficiently collected.

Moreover, the collected bone marrow (hereinafter also referred to as the "bone marrow fluid") coagulates immediately after the collection. Thus, the inner needle for collecting a bone marrow fluid has been designed such that an anticoagulant is supplied into the inner needle to mix the bone marrow fluid and the anticoagulant. Also in the Patent Literature 1, an anticoagulant supply port is connected to the vicinity of the base of the inner needle, and the anticoagulant is supplied from the supply port into the inner needle.

In addition, with the histological structure of the bone marrow tissue, a bone marrow fluid does not flow into the outer edge of the perforation hole (puncture hole) formed immediately after collection of a certain amount of bone marrow fluid from the periphery, and peripheral blood is mainly supplied to the outer edge at the time of duplicate collection. Therefore, in the past, the outer needle has been re-punctured into the ilium by changing the location and angle of the outer needle many times without changing the hole made in the skin. After completion of a certain treatment for one hole made in the skin, another hole has been made in a different location in the skin, and the same treatment has been performed.

As a result, the number of holes in the skin was, for example, 2 to 6 in total, but the number of places where the outer needle was punctured into the cortical bone of the ilium was 100 to 200 or more.

The reason for collection from multiple sites as described above is that the amount of bone marrow fluid collected at one site was limited to 3 to 5 mL. At this time, there was no method to check the inside of the ilium and the position of the tip of the puncture needle in the ilium from the outside. There was much duplication of the collecting site. In other words, conventionally, it has been impossible to check the position of the collecting site from the outside, and it has been necessary to employ a method to increase the probability of collecting the required amount of bone marrow fluid by randomly changing the collecting site over a wide range.

CITATION LIST

Patent Literature

Patent Literature 1: Japanese Patent No. 4808961

SUMMARY OF INVENTION

Technical Problem

However, in the Patent Literature 1, an opening is provided in a side wall in the vicinity of the tip of the inner needle, and a bone marrow fluid collected from the opening is aspirated by an aspiration device. Thus, there was a problem where the anticoagulant supplied from the supply port in the vicinity of the base of the inner needle does not reach the vicinity of the opening and coagulates before reaching the supply port from the opening.

It is conceivable to insert a tube for supplying an anticoagulant into an inner space of the inner needle. However, it is not preferable because a hollow portion of the inner needle serving as an aspiration path for bone marrow fluid is blocked by the tube. Moreover, if the outer diameter of the inner needle is made larger in accordance with the tube for supplying the anticoagulant, the perforation hole (puncture hole) made by the inner needle becomes too large, which is not preferable.

In addition to the case of collecting the bone marrow fluid, the above-described problem also arises when a predetermined drug solution is administered (supplied) to the body tissue while the puncture needle or the like is moved in the body.

Hence, a first object of the present invention is to provide a puncture instrument capable of administering (supplying) a drug solution, for example, a puncture instrument or puncture device capable of reliably administering (supplying) a drug solution without unnecessarily enlarging a perforation hole (puncture hole) to be formed in a body tissue.

In addition, in any of the bone marrow puncture needles, a large amount of bone marrow fluid containing peripheral blood is required to obtain a sufficient amount of bone marrow hematopoietic stem cells, and stem cells have not been efficiently collected.

Furthermore, if the tip of the inner needle with a drill blade is sharp as in the Patent Literature 1, this sharp tip may puncture (perforate) the medullary cavity or the like, leading to a serious accident. In addition, if an opening for aspirating the bone marrow fluid is formed on the side of the tubular body connected to the inner needle as in the Patent Literature 1, the opening may be separated from the tip of the perforating (puncturing) inner needle. Further, the opening may be orthogonal to the puncturing direction of the tip of the inner needle. Therefore, it is difficult to aspirate the bone marrow fluid efficiently, which may cause clogging in some cases.

Hence, a second object of the present invention is to provide a bone marrow puncture device capable of efficiently aspirating a bone marrow fluid. The second object of the present invention also is to provide a bone marrow puncture device with which, for example, the tip in the puncturing direction does not puncture (perforate) out the medullary cavity (e.g., the possibility of puncturing out is reduced).

Further, in the method of the Patent Literature 1 mentioned above, the angle of the outer needle and the direction for moving the inner needle must rely on the intuition of the operator. Thus, the operator may move the inner needle to the same site where the collection was once performed. Accordingly, the efficiency of the collection of bone marrow is not good.

In addition, if the aspiration rate is too slow, blood may be aspirated too much, and in contrast, if the aspiration rate is too fast, the amount of the collected bone marrow fluid may decrease. In order to maintain a good quality of collecting a bone marrow fluid, it is necessary to move the inner needle at an appropriate rate. However, conventionally, this collection rate also has depended on the intuition of the operator.

In order to solve the above-mentioned problems, it is conceivable that the inside of the ilium and the positions of the outer and inner needles inside the ilium are caused to be capable of being checked from the outside by using the ultrasonic device. However, the attenuation of ultrasound is large inside the bone, and it is very difficult to use the ultrasonic device for a deep region where the bone marrow fluid is collected.

Further, the above-mentioned problem similarly arises when a puncture needle or the like is advanced into the body and at the same time, a predetermined treatment is performed on the body tissue, in addition to the case of collecting the bone marrow fluid.

Hence, a third object of the present invention is to provide a puncture device capable of keeping the quality of treatment constant regardless of the experience of an operator. The third object of the present invention also is to provide a puncture device capable of, for example, improving the efficiency of the treatment on the body tissue and shortening the time required for the treatment.

Solution to Problem

In order to achieve the first object, the first puncture instrument or puncture device according to the present invention comprises: a puncture tip section; a first tubular body connected to the puncture tip section at a distal end; and an outer tubular body at least partially covering the first tubular body. The first tubular body is formed to be rotatable around an axis along the longitudinal direction and has an outer diameter smaller than an inner diameter of the outer tubular body, and a drug solution supply path is provided on the outside of the first tubular body.

In order to achieve the second object, the bone marrow puncture instrument or bone marrow puncture device according to the present invention comprises, in a bone marrow puncture instrument or bone marrow puncture device with a tip that is at least inserted into a medullary cavity to collect a bone marrow fluid, a tubular body comprising a distal end and an opening in a surface at the distal end; a tip rotation section configured to perforate (puncture) a tissue in a medullary cavity while rotating together with the tubular body, the tip rotation section being disposed on a distal side of the surface at the distal end in the tubular body; and a connection member configured to connect the tubular body and the tip rotation section.

In order to achieve the third object, the second puncture device according to the present invention comprises: a puncture unit comprising a puncture tip section and a tubular body connected to the puncture tip section, the puncture unit being configured to subject a body tissue to a predetermined treatment while moving in a body; and a moving rate calculation unit configured to calculate a moving rate of the puncture unit.

Advantageous Effects of Invention

With the first puncture instrument or puncture device according to the present invention, a drug solution can be administrated. Moreover, with the first puncture instrument or puncture device according to the present invention, a drug solution can be transferred to the outer surface of the first tubular body through a drug solution supply path provided on the outside of the first tubular body, for example. The drug solution transferred to the outer surface of the first tubular body is transferred to the puncture tip section side and mixed with the tissue collected with the puncture tip section, such as a bone marrow fluid, for example. Moreover, for example, the first tubular body has an outer diameter smaller than an inner diameter of the outer tubular body and is rotatable around an axis along the longitudinal direction. The drug solution transferred to the outer surface of the first tubular body is thus transferred to the puncture tip section side and mixed with a bone marrow fluid or the like immediately after collection by the puncture tip section by the rotation of the first tubular body. Moreover, with the first puncture instrument or puncture device according to the present invention, the bone marrow fluid or the like can be reliably prevented from coagulating when an anticoagulant is used as the drug solution, for example. The first tubular body that transfers a drug solution is placed in the outer tubular body, for example. The aspiration path for the bone marrow fluid or the like thus can be sufficiently secured without unnecessarily enlarging the perforation hole (puncture hole) for collecting the bone marrow fluid or the like. More specifically, the first puncture instrument or puncture device according to the present invention can transfer the drug solution without providing a member for transferring the drug solution separately from the first tubular body and the outer tubular body, for example. The present invention can provide a puncture instrument (e.g., a bone marrow puncture instrument) or a puncture device (e.g., bone marrow puncture device) capable of reliably administering a drug solution without unnecessarily enlarging a perforation hole (puncture hole) formed in the body tissue. That is, with the first puncture instrument or puncture device according to the present invention, the size (e.g., diameter) of the puncture instrument or puncture device can be small, and a perforation hole (puncture hole) formed in the body tissue thus can be small.

With the bone marrow puncture instrument or bone marrow puncture device according to the present invention, a bone marrow fluid can be efficiently aspirated. Specifically, with the bone marrow puncture instrument or bone marrow puncture device according to the present invention, for example, the tissue in the medullary cavity is perforated (punctured) by the tip rotation section rotating together with the tubular body, and the surface at the distal end of the tubular body connected from the tip rotation section with the connection member is provided with an opening. Thus, the bone marrow fluid can be efficiently aspirated from the tissue in the medullary cavity perforated (punctured) by the tip rotation section.

In the second puncture device according to the present invention, a moving rate of the bone marrow puncture unit is calculated by a moving rate calculation unit when the position of the puncture unit moving in the body is changed. Thus, with the second puncture device according to the present invention, by referring to the calculated moving rate of the bone marrow puncture unit, the moving rate of the puncture unit can be set to be in an appropriate range, and the quality of the treatment can be kept constant regardless of the experience of the operator.

BRIEF DESCRIPTION OF DRAWINGS

FIG. 4A is a plan view illustrating an entire guide tube where an inner needle is inserted into an outer needle. FIG. 4B is a cross-sectional view of FIG. 4A. FIG. 4C is a plan view illustrating the outer needle. FIG. 4D is a plan view illustrating the inner needle. FIG. 4E is a cross-sectional view of FIG. 4D.

FIG. 9A illustrates a puncture mark when puncturing is performed at an angle of entry of 5°. FIG. 9B illustrates a puncture mark at an angle of entry of 10°. FIG. 9C illustrates a puncture mark when puncturing is performed at an angle of entry of 15°.

FIG. 20A illustrates a puncture mark when puncturing is performed at an angle of entry of 5°. FIG. 20B illustrates a puncture mark at an angle of entry of 10°. FIG. 20C illustrates a puncture mark when puncturing is performed at an angle of entry of 20°.

DESCRIPTION OF EMBODIMENTS

In the description of the first puncture instrument or puncture device according to the present invention, the "distal end" herein refers to the end of the first tubular body that is farther as viewed from the operator when the operator punctures the puncture tip of the puncture device (puncture instrument) into the surgical site.

In the description of the first puncture instrument or puncture device according to the present invention, the "proximal end" herein refers to the end of the first tubular body that is closer as viewed from the operator when the operator punctures the puncture tip section of the puncture device (puncture instrument) into the surgical site.

In the description of the bone marrow puncture instrument or bone marrow puncture device according to the present invention, the "distal end" herein refers to the end of the tubular body that is farther as viewed from the operator when the operator inserts the tip of the bone marrow puncture device (bone marrow puncture instrument) into a medullary cavity. In the description of the bone marrow puncture instrument or bone marrow puncture device according to the present invention, the "distal side" herein refers to the side that is farther from the surface at the distal end of the tubular body as viewed from the operator. In the description of the bone marrow puncture instrument or bone marrow puncture device according to the present invention, the "proximal side" herein refers to the side that is closer to the tubular body as viewed from the operator.

The following describes the embodiment of the present invention with reference to the drawings.

(Configuration of Bone Marrow Puncture System)

Figure 1:
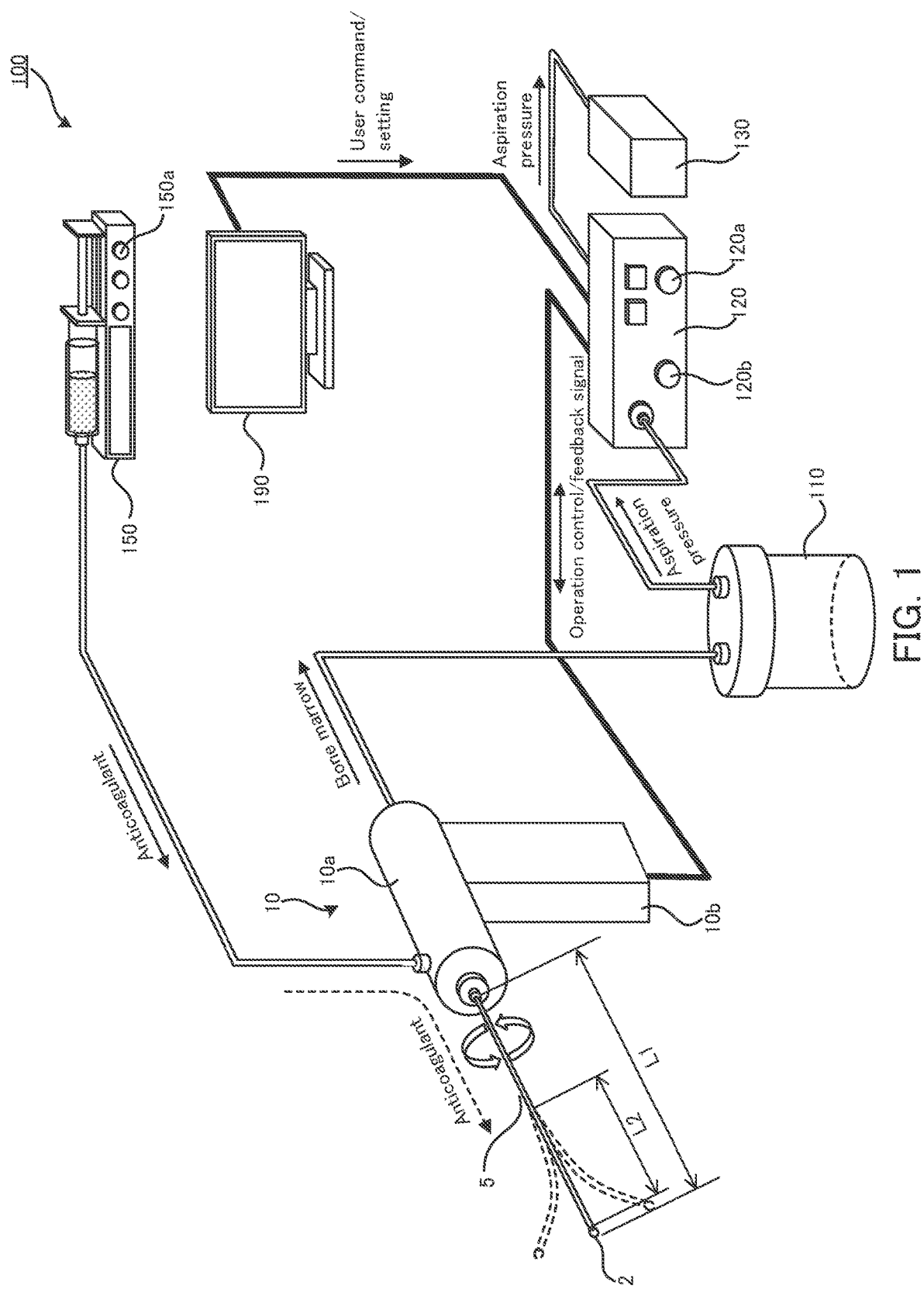
FIG. 1 is a drawing schematically illustrating a bone marrow puncture system according to an embodiment of the present invention.
Figure 2:
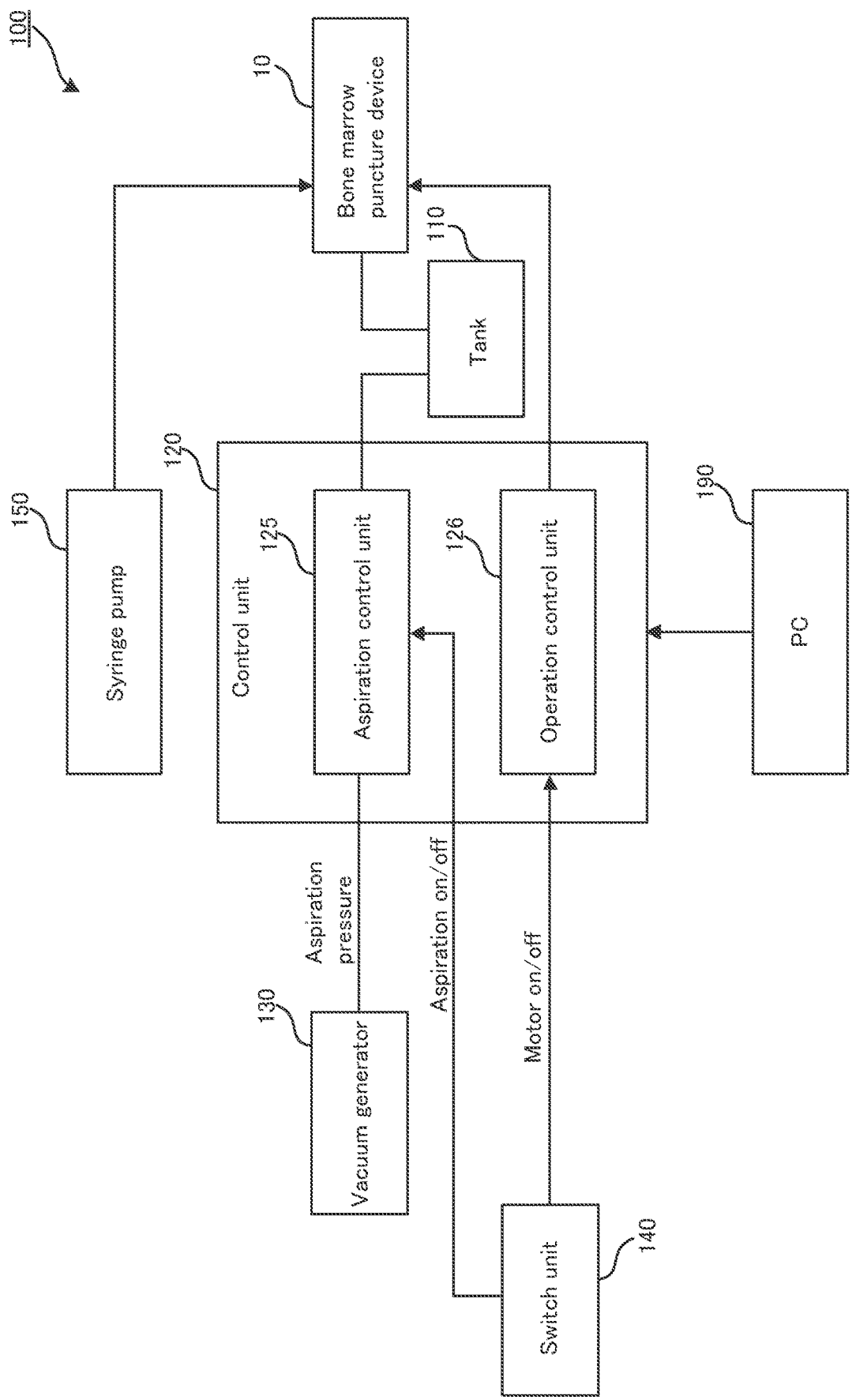
FIG. 2 is a block diagram illustrating a configuration of the bone marrow puncture system.

A configuration of a bone marrow puncture system 100 will be described with reference to the drawings. FIG. 1 is a drawing schematically illustrating a bone marrow puncture system 100 according to an embodiment of the present invention. FIG. 2 is a block diagram illustrating a configuration of the bone marrow puncture system 100. Parts relating to navigation, which will be described later, are omitted in FIGS. 1 and 2.

As shown in FIGS. 1 and 2, the bone marrow puncture system 100 includes a bone marrow puncture device 10, a tank 110, a control unit 120, a vacuum generator 130, a switch unit 140, a syringe pump 150, and a personal computer (hereinafter referred to as PC) 190.

The bone marrow puncture device 10 as an example of the puncture device includes a housing 10a, and a bone marrow puncture unit 1 to be described below and a drive unit that includes a motor (not shown) are provided in an inner space of the housing 10a. A handle 10b is formed in the housing 10a so as to be easily operated by an operator.

As shown in FIG. 1, a mantle (outer tubular body) 5 covering a first tubular body 3 and a second tubular body 4 of the bone marrow puncture unit 1 to be described below is projected from the housing 10a, and a puncture tip section 2 is attached to the end of the first tubular body 3 covered with the mantle 5. The length of the projection from the housing 10a, including the first tubular body 3, the second tubular body 4, the mantle 5, and the puncture tip section 2 is represented by L1. The mantle 5 covering the first tubular body 3 and the first tubular body 3 has flexibility as indicated by a dotted line of FIG. 1. The length of a portion of the mantle 5 having flexibility is represented by L2. The first tubular body 3, the second tubular body 4, and the puncture tip section 2 covered with the mantle 5 are rotatable counterclockwise or clockwise. The bone marrow puncture unit 1 including the puncture tip section 2, the first tubular body 3, the second tubular body 4, and mantle 5 will be described later.

The tank 110 is a container for storing the bone marrow fluid aspirated by the bone marrow puncture device 10 and is connected to the bone marrow puncture device 10. The tank 110 is connected to the aspiration control unit 125 of the control unit 120, and the values of the aspiration pressure in and the on/off of application of the aspiration pressure to the tank 110 and the bone marrow puncture device 10 connected to the tank 110 are controlled by the aspiration control unit 125.

The control unit 120 includes a central processing unit (CPU), a read only memory (ROM), a random access memory (RAM), and the like (not shown) and functions as the aspiration control unit 125 and the operation control unit 126. The aspiration control unit 125 is connected to the vacuum generator 130 and the switch unit 140. The vacuum generator 130 as an aspiration device generates predetermined negative pressure. The predetermined negative pressure is, for example, −90 kpa or more and less than 0 kpa.

The switch unit 140 is placed near the operator and includes a switch for turning aspiration on/off and a switch for turning a motor on/off. The switch unit 140 is not shown in FIG. 1. The switch unit 140 may be provided separately from or integrally with the bone marrow puncture device 10. For example, in the case where the switch unit 140 is configured separately from the bone marrow puncture device 10, the switch unit 140 may be provided as a foot switch. For example, in the case where the switch unit 140 is configured integrally with the bone marrow puncture device 10, the switch unit 140 may be provided on the handle 10b.

The aspiration control unit 125 includes a valve (not shown), and when the switch unit 140 receives an aspiration on/off signal through an operation by an operator, the valve is turned on/off. The valve may be provided in an internal tank connected to the control unit 120 and the vacuum generator 130, for example. Accordingly, the on/off of application of the aspiration pressure to the bone marrow puncture device 10 is controlled. A knob 120a is provided in the control unit 120, and values of the aspiration pressure can be adjusted by turning the knob 120a. The valve may be turned off after the elapse of a predetermined time when the aspiration control unit 125 receives an off signal, for example. Accordingly, the aspiration control unit 125 can prevent leakage of anticoagulant supplied from an opening 20b of a tube 20 to the bone marrow puncture unit 1, for example.

An operation control unit 126 is connected to the drive unit of the bone marrow puncture device 10 and the switch unit 140. When the switch unit 140 receives a motor on/off signal through an operation by an operator, the motor on/off signal is sent to a motor in the drive unit. Accordingly, rotation and stopping of the bone marrow puncture unit 1 in the bone marrow puncture device 10 are controlled. A knob 120b is provided in the control unit 120, and a rotation rate of the motor can be adjusted by turning the knob 120b. The rotation rate and the torque of the motor are, for example, the rotation rate and the rotation torque at which a tissue in a medullary cavity can be punctured, for example. The rotation rate is, for example, 60 to 150 rpm. The rotation torque is, for example, 500 mN·m or less, or 300 mN·m or less. The propulsive force of the bone marrow puncture unit 1 is, for example, 15N to 20N. The propulsive rate of the bone marrow puncture unit 1 is, for example, about 1 mm/sec. In the present embodiment, the rotation rate is set at 120 rpm as an example and can be set at 90, 120, or 150 rpm by the knob 120b, for example. The operation control unit 126 may calculate the amount of current of the motor in the drive unit based on the rotation torque of the deformation limit of the first tubular body 3, for example, in order to prevent perforating out of the cortical bone and breakage of the first tubular body 3. In this case, the operation control unit 126 may send an OFF signal to the motor in the drive unit at the time of an overload in which a current exceeding the above-mentioned current value is required. That is, the operation control unit 126 may interrupt driving of the motor. When an overload protection unit such as a torque limiter is mounted on the shaft of the motor in the drive unit, the operation control unit 126 may send a signal for suppressing the rotation rate to the overload protection unit. That is, the operation control unit 126 may mechanically interrupt the overload of the motor in the drive unit. For example, the operation control unit 126 may notify the state of the rotation torque and the current value of the motor in the drive unit to the operator by blinking of a lamp, a warning sound, or the like. When the overload is eliminated, the operation control unit 126 may send an ON signal to the motor in the drive unit to drive the motor again, for example.

The syringe pump 150 is a pump for supplying an anticoagulant as the drug solution to the bone marrow puncture device 10. The syringe pump 150 is connected to the bone marrow puncture device 10. A knob 150a is provided in the syringe pump 150, and an anticoagulant supply rate can be adjusted by turning the knob 150a. In the present embodiment, an anticoagulant such as heparin is supplied at 40 μl/sec as an example. An anticoagulant supply system will be described in detail later. In present embodiment, an anticoagulant is supplied using the syringe pump 150. The present invention, however, is by no means limited thereto, and an anticoagulant may be supplied using another liquid transfer unit such as a ring pump, for example.

The PC 190 is connected to the control unit 120 and can output a command to the control unit 120 and output data for setting. The PC 190 includes, for example, a CPU, a main memory (an ROM, an RAMs, etc.), a secondary storage device (a hard disc, a flash memory, etc., hereinafter also referred to as a "recording unit"), a video codec, and an I/O (input-output) interface, etc., which are controlled and operated by a controller (a system controller, an I/O controller, etc.). The PC 190 may include an input unit (e.g., a keyboard) and an output unit (e.g., a display such as a liquid crystal display, or a printer), for example. In the present embodiment, the PC 190 is a personal computer but may have a configuration similar to a server computer, a workstation, or the like. The PC 190 may be configured by, for example, a mobile terminal (a smartphone, a tablet, etc.), a smart speaker, and the like.

Figure 21:
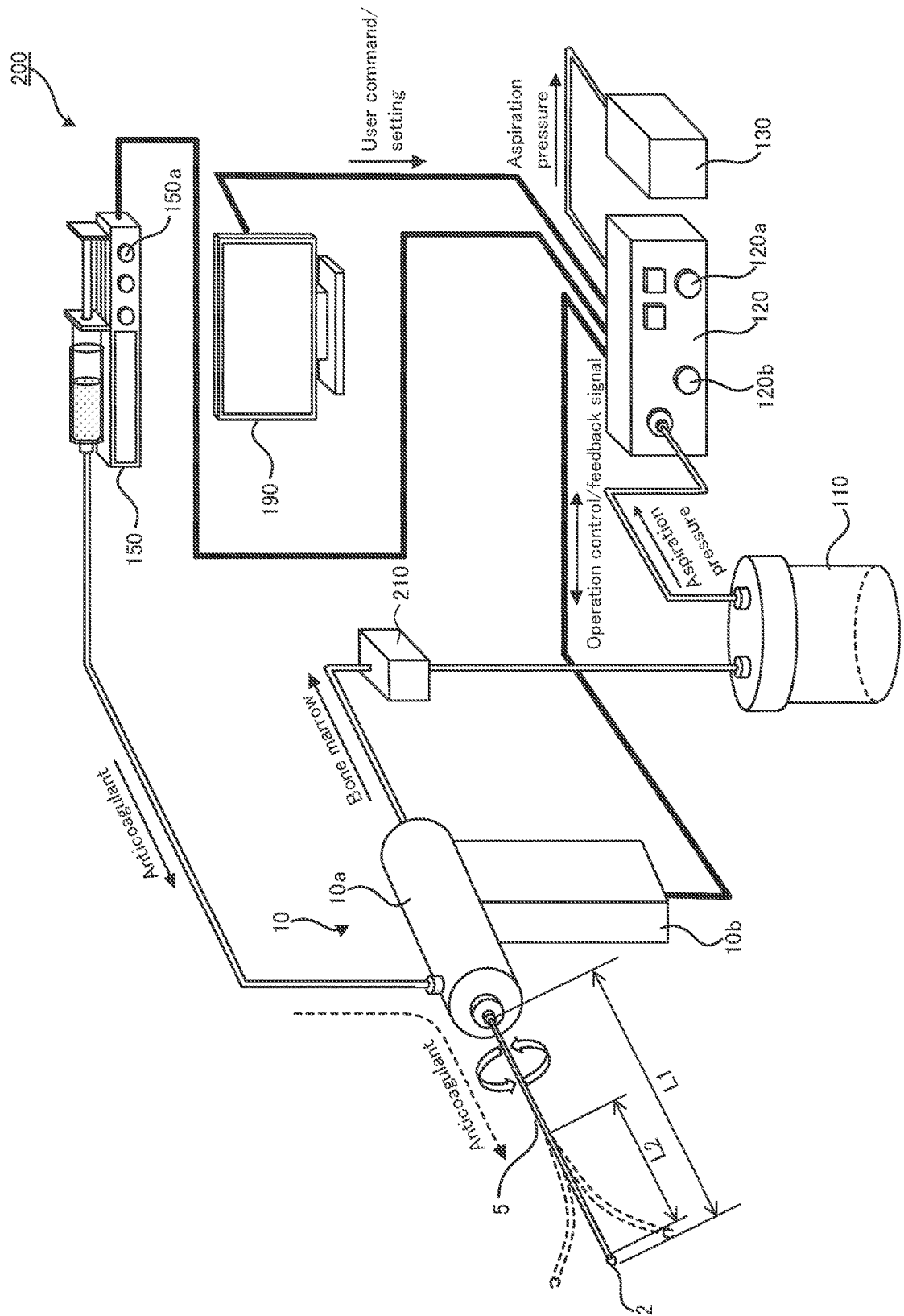
FIG. 21 is a drawing schematically illustrating a modification of a bone marrow puncture system according to the present invention.
Figure 22:
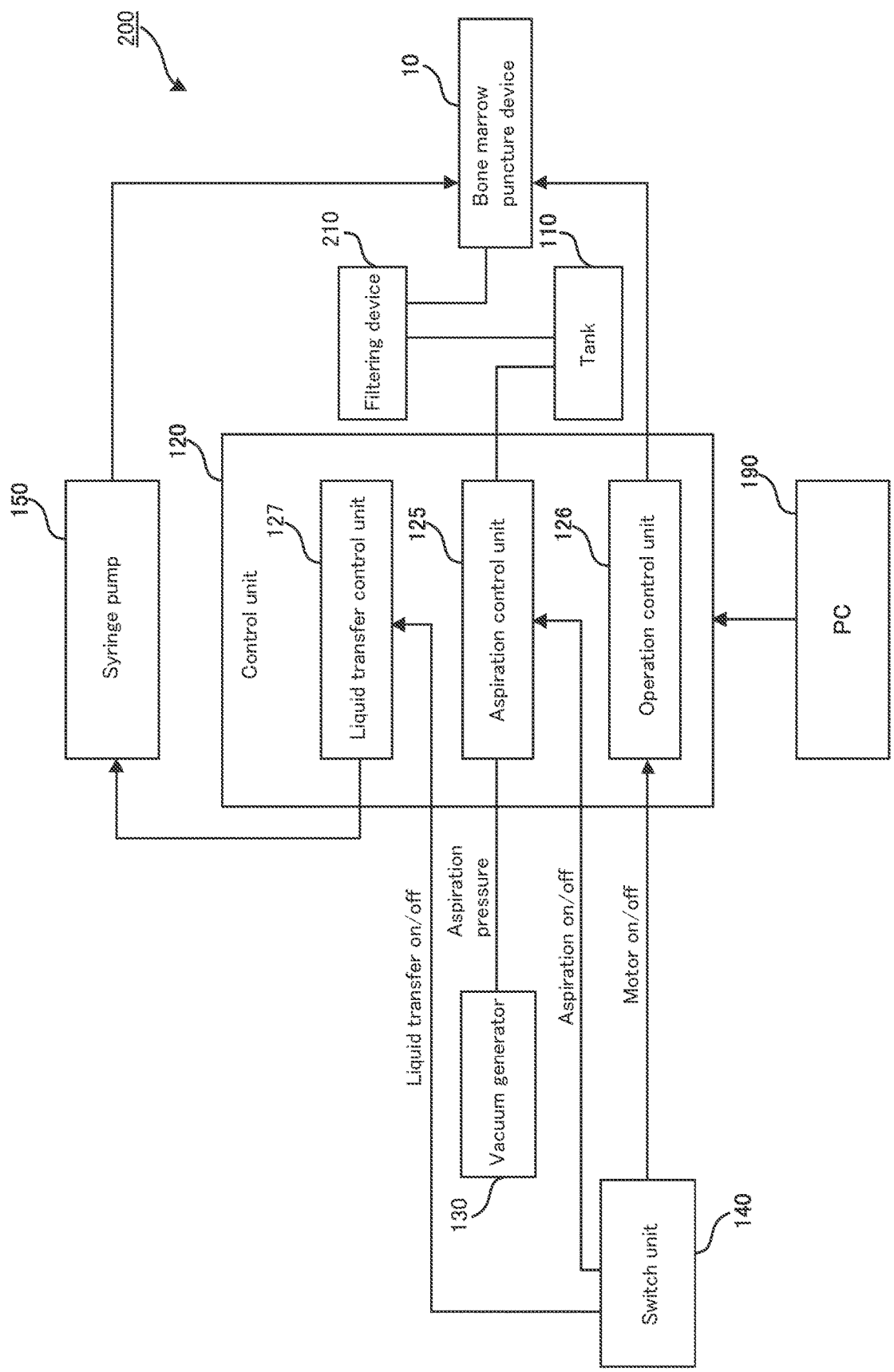
FIG. 22 is a block diagram illustrating a configuration of a modification of the bone marrow puncture system.

FIG. 21 is a drawing schematically illustrating a bone marrow puncture system 200 of a modification. FIG. 22 is a block diagram illustrating a configuration of the bone marrow puncture system 200 of the modification. Parts relating to navigation, which will be described later, are omitted in FIGS. 21 and 22.

As shown in FIGS. 21 and 22, a bone marrow puncture system 200 includes a filtering device 210 in addition to the configuration of the bone marrow puncture system 100. The control unit 120 includes a liquid transfer control unit 127 in addition to the aspiration control unit 125 and the operation control unit 126. The syringe pump 150 is electrically connected to the control unit 120.

The filtering device 210 is a device for filtering the bone marrow fluid aspirated by the bone marrow puncture device 10 and removes the cancellous bone in the bone marrow fluid. The filtering device 210 may be, for example, a commercially available filter, a housing, or the like. The filtering device 210 is connected to the bone marrow puncture device 10 and the tank 110. The tank 110 connected to the filtering device 210 is connected to the aspiration control unit 125 of the control unit 120 as mentioned above. Therefore, the pressure value of the aspiration pressure and the on/off of application of the aspiration pressure of the bone marrow puncture device 10 connected to the tank 110, the filtering device 210, and the tank 110 are controlled by the aspiration control unit 125.

The control unit 120 functions as the aspiration control unit 125, the operation control unit 126, and the liquid transfer control unit 127.

The liquid transfer control unit 127 is connected to the syringe pump 150 and the switch unit 140. When the liquid transfer control unit 127 receives a liquid transfer on/off signal from the switch unit 140 by the operation of the operator, the liquid transfer control unit 127 sends the liquid transfer on/off signal to the syringe pump 150. Thus, the start/stop of the liquid transfer from the syringe pump 150 is controlled. Accordingly, the on/off of liquid transfer from the syringe pump 150 is controlled in synchronism with the on/off of application of aspiration pressure to the bone marrow puncture device 10. Therefore, the anticoagulant supplied to the bone marrow puncture unit 1 can be prevented from leaking out of the opening 20b of the tube 20. A knob 150a is provided in the syringe pump 150, and an anticoagulant supply rate can be adjusted by turning the knob 150a, as mentioned above. The present invention, however, is not limited thereto, and for example, the liquid transfer control unit 127 may be capable of adjusting the supply rate of a drug solution such as an anticoagulant.

In the bone marrow puncture system 200 of a modification, the aspiration control unit 125, the operation control unit 126, and the liquid transfer control unit 127 are connected to the switch unit 140. However, the switch unit 140 may be connected to the operation control unit 126, and the operation control unit 126 may be connected to the aspiration control unit 125 and the liquid transfer control unit 127. In this case, when the operation control unit 126 receives a motor on/off signal, an aspiration on/off signal, and a liquid delivery on/off signal from the switch unit 140 through an operation by an operator, the operation control unit 126 sends the aspiration on/off signal and the liquid transfer on/off signal to the aspiration control unit 125 and the liquid transfer control unit 127. Then, the operation control unit 126 sends an on/off signal to the motor in the drive unit. The aspiration control unit 125 controls on/off of application of aspiration pressure to the bone marrow puncture device 10. The liquid transfer control unit 127 controls on/off of liquid transfer from the syringe pump 150. The control unit 120 of the bone marrow puncture system 100 may be configured in the same manner as described above.

(Configuration of Bone Marrow Puncture Unit)

Figure 3:
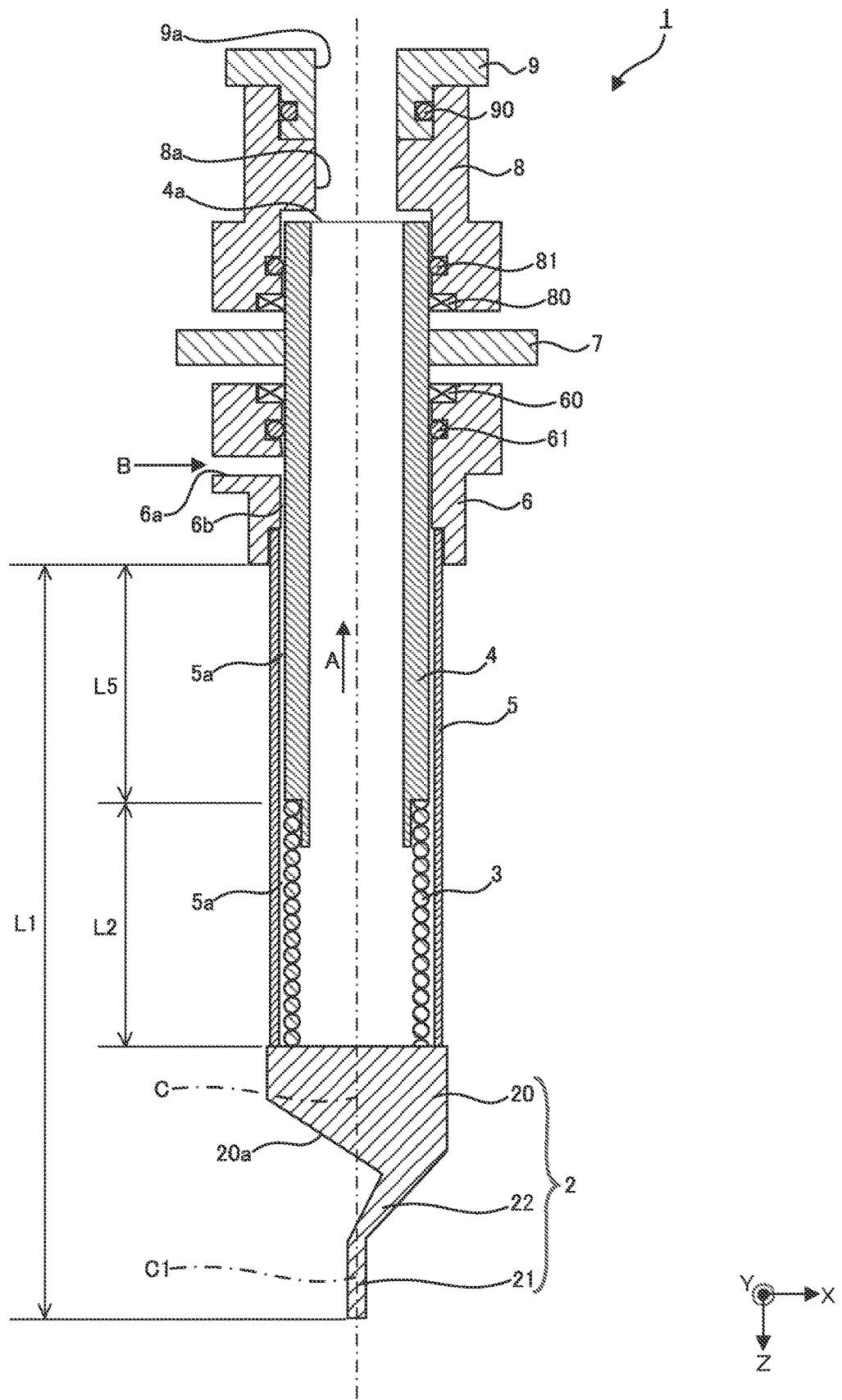
FIG. 3 is a cross-sectional view schematically illustrating a bone marrow puncture unit in the bone marrow puncture device.

The configurations of the bone marrow puncture device 10 and the bone marrow puncture unit 1 will be described with reference to the drawings. FIG. 3 is a cross-sectional view schematically illustrating a bone marrow puncture unit 1 in the bone marrow puncture device 10 according to the present embodiment. Please note that FIG. 3 is a drawing schematically illustrating the bone marrow puncture unit 1 and does not show the actual length, thickness, or ratio.

As shown in FIG. 3, the bone marrow puncture unit 1 according to the present embodiment includes a puncture tip section 2, a first tubular body 3, a second tubular body 4, a mantle 5, a first shaft 6, a gear 7, a second shaft 8, and a tank connection member 9. The puncture tip section 2, the first tubular body 3, the second tubular body 4, and the mantle 5 (hereinafter also referred to as a "bone marrow puncture needle" or a "puncture needle") in the bone marrow puncture unit 1, are attached detachably to the insides of the first shaft 6, the gear 7, and the second shaft 8. A magnetic sensor utilized in navigation, which will be described later, is omitted in FIG. 3.

Figure 5:
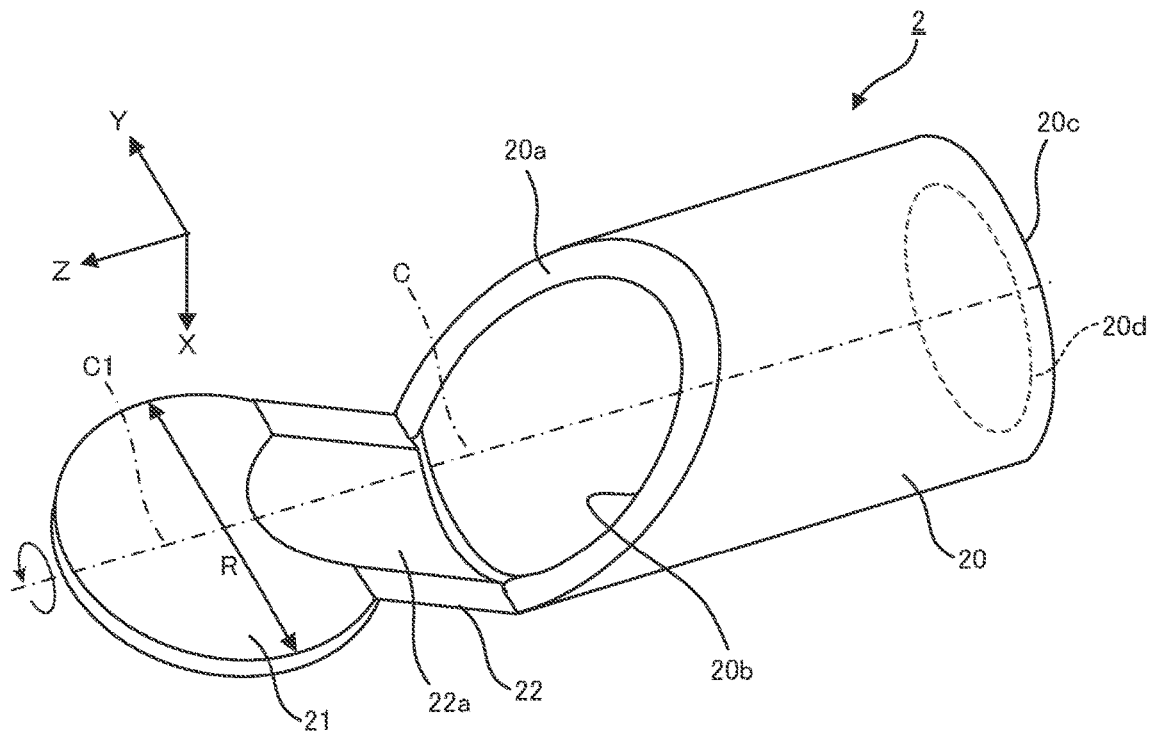
FIG. 5 is a perspective view illustrating a puncture tip section.
Figure 7:
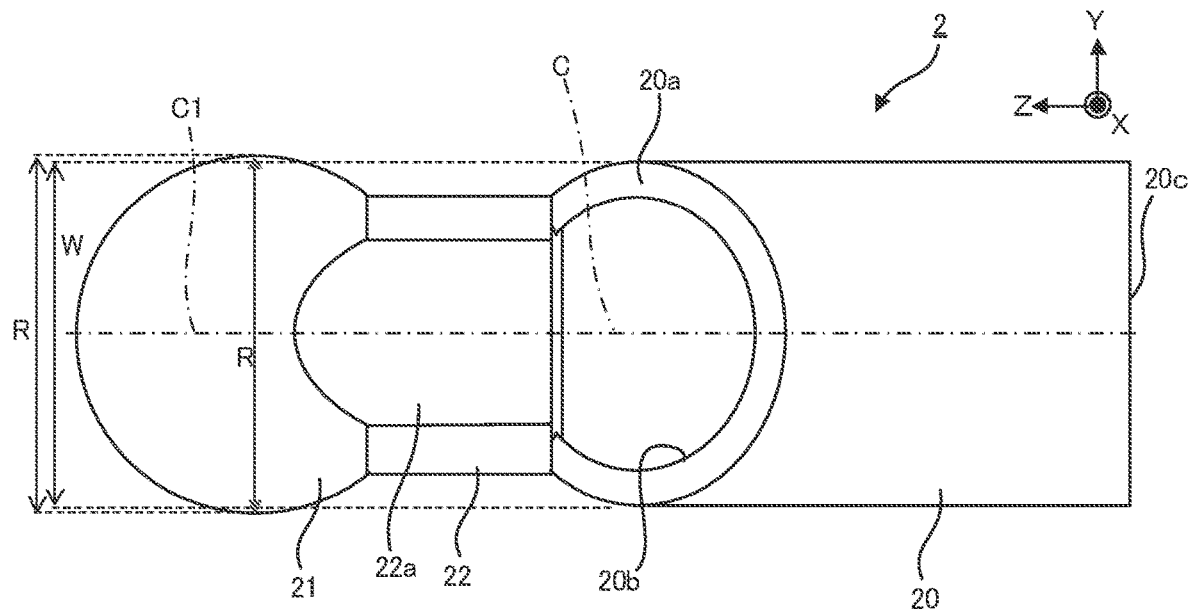
FIG. 7 is a plan view illustrating the puncture tip section.
Figure 8:
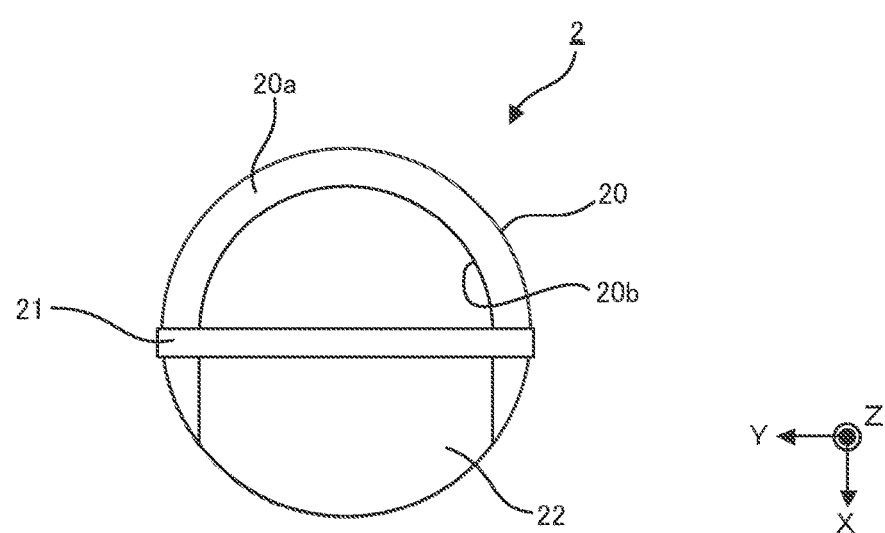
FIG. 8 is a front view showing the puncture tip section.

The puncture tip section 2 includes a tube 20, a disc-shaped member 21 as a tip rotation section, and a connection member 22. As shown in FIGS. 5, 7, and 8 to be described later, the tube 20 includes an opening 20b. The tube 20 here forms a tubular body with the first tubular body 3 and the second tubular body 4, and the opening 20b is provided in the surface at the distal end of the tubular body. The disc-shaped member 21 has a radial central axis C1, which coincides with the central axis C of the tube 20 and is positioned at the tip in the puncturing direction indicated by an arrow Z. In the specification of the present application, the "puncturing direction" means the direction in which the puncture tip section 2 of the bone marrow puncture device 10 perforates (punctures) the bone marrow. The connection member 22 connects between a part of an end surface 20a of the tube 20 (the surface at the distal end of the tubular body) and the disc-shaped member 21. The tube 20, the disc-shaped member 21, and the connection member 22 in the puncture tip section 2 are formed of metals such as stainless steel, a titanium alloy, a precious metal alloy, and cobalt alloy (hereinafter also referred to as "a metal such as stainless") and are integrally formed by carving or the like. The disc-shaped member 21 and the connection member 22 may be formed integrally by carving or the like, and the connection member 22 may then be jointed to the tube 20. Alternatively, the tube 20, the disc-shaped member 21, and the connection member 22 may each be formed by carving or the like and may then be jointed to each other. The puncture tip section 2 will be described in detail later.

The first tubular body 3 is a tube body connected to the tube 20 of the puncture tip section 2 and is formed to be rotatable around an axis along the longitudinal direction. The first tubular body 3 can also be referred to as a tube that is rotatable around an axis in a longitudinal axis, for example. The first tubular body 3 is, for example, a coil body of a round wire of stainless steel or the like and is formed by winding a round wire into a coil shape. The coil body may be formed of metals other than stainless steel such as a titanium alloy, a precious metal alloy, or a cobalt alloy. The coil body may be a coil body of a wire other than a round wire such as a rectangular wire. A direction for winding the first tubular body 3 agrees with a direction for rotating the first tubular body 3 (e.g., a counterclockwise or clockwise (CW)). The first tubular body 3 is formed into a coil shape and thus has flexibility and is formed such that a drug solution such as an anticoagulant is permeable from gaps between coil turns of the round wire (e.g., permeation holes). The outer diameter of the first tubular body 3 is formed to have an outer diameter that is smaller than the inner diameter of the mantle 5 and is rotatable inside the mantle 5. A drug solution supply path 5a is formed between the outer peripheral surface of the first tubular body 3 and the inner peripheral surface of the mantle 5. A portion of the mantle 5 covering the first tubular body 3 and the first tubular body 3 has a length L2 and corresponds to a flexible portion of the mantle 5 having a length L2 shown in FIG. 1.

The second tubular body 4 is a rigid cylindrical tube connected to the first tubular body 3 and is formed of a metal such stainless, for example. The second tubular body 4 is formed to have an outer diameter smaller than the inner diameter of the mantle 5 and is rotatable inside the mantle 5 together with the first tubular body 3. A drug solution supply path 5*a* is formed between the outer peripheral surface of the second tubular body 4 and the inner peripheral surface of the mantle 5 and is continuously formed from the drug solution supply path 5*a* formed between the outer peripheral surface of the first tubular body 3 and the inner peripheral surface of the mantle 5. The length of the second tubular body 4 is preferably a length such that the second tubular body 4 is not exposed from the distal end of a guide tube to be mentioned below when the bone marrow puncture needle is moved in the direction of the distal end, for example, within the guide tube. That is, a length L5 in FIG. 3 is preferably the length L4 shown in FIG. 4 to be described later or less. The length L5 can also be said to be, for example, a longitudinal length of an area of the second tubular body 4, projecting from the first shaft 6 and excluding the connection member with the first tubular body 3. With this configuration, the puncture tip section 2 can be pushed out in the axial direction of the guide tube by the second tubular body 4. Thus, the puncturing direction of the puncture tip section 2 in the bone marrow puncture unit 1 agrees, for example, with the axial direction of the guide tube. That is, with the length of the second tubular body 4, the puncturing direction of the bone marrow puncture device 10 can be easily set, for example.

The mantle 5 is, for example, a cylindrical tube formed of a plastic such as polytetrafluoroethylene (PTFE) or a resin and has a length such that the mantle 5 can cover the entire first tubular body 3 and a part of the second tubular body 4. The mantle 5 has flexibility. As mentioned above, the mantle 5 is formed to have an inner diameter that is larger than the outer diameters of the first tubular body 3 and the second tubular body 4. The first tubular body 3 and the second tubular body 4 are rotatable in an inner space of the mantle 5. A drug solution supply path 5*a* is formed between the inner peripheral surface of the mantle 5 and the outer peripheral surfaces of the first tubular body 3 and the second tubular body 4. One end of the mantle 5 is in contact with an end surface of the tube 20 of the puncture tip section 2 such that rotation of the puncture tip section 2 is not interrupted, and the other end is inserted into the first shaft 6. That is, the mantle 5 is configured such that the mantle 5 itself is not rotated. With this configuration, generation of friction caused by rotation of the mantle 5 can be prevented, and generation of heat, increase in rotational load, and the like caused by the friction can be prevented.

The length of a portion including a portion of the second tubular body 4 projecting from the first shaft 6, a portion of the mantle 5 covering the first tubular body 3, and the puncture tip section 2 is represented by L1, and the portion having the length L1 corresponds to the projection having the length L1 shown in FIG. 1.

The first shaft 6 is a non-rotation body formed of a metal such as stainless, plastic, a resin, or the like and is attached to the outer periphery of the second tubular body 4 via a bearing 60. An O-ring 61 is attached between the first shaft 6 and the second tubular body 4 to ensure a tight fit between the first shaft 6 and the second tubular body 4 toward the bearing 60 side. An inlet 6*a* for a drug solution such as an anticoagulant is formed in the first shaft 6, and a drug solution such as an anticoagulant is supplied from the syringe pump 150 as a drug solution supply section shown in FIGS. 1 and 2 in a direction indicated by an arrow B. A drug solution supply path 6*b* is formed between the inner periphery of the first shaft 6 in the vicinity of the inlet 6*a* and the outer periphery of the second tubular body 4, and the drug solution supply path 6*b* continues from the above-mentioned drug solution supply path 5*a*. Thus, a drug solution supplied from the inlet 6*a* is transferred to the outer periphery of the first tubular body 3 through the drug solution supply paths 6*b* and 5*a* and is permeated from gaps between coil turns of the round wire of the first tubular body 3.

The gear 7 is, for example, formed of carbon steel, a metal such as stainless, plastic, a resin, or the like and fits in the second tubular body 4. A rotational force of the motor (not shown) is propagated to the gear 7 via a pinion gear (not shown) or the like, thereby rotating the second tubular body 4. As a result, the first tubular body 3 and the puncture tip section 2 are rotated together with the second tubular body 4. In the present embodiment, the number of revolutions of the second tubular body 4, the first tubular body 3, and the puncture tip section 2 is set to 120 rpm as an example. The gear ratio of the gear 7 is not particularly limited and can be set, as appropriate, according to an installation method of the drive unit.

For example, the second shaft 8 is a non-rotation body formed of a metal such as stainless, plastic, a resin, or the like and is attached to the outer periphery of the second tubular body 4 via a bearing 80. An O-ring 81 is attached between the second shaft 8 and the second tubular body 4 to ensure a tight fit between the second shaft 8 and the second tubular body 4 toward the bearing 80 side. A communication hole 8*a* communicating with a rear end opening 4*a* of the second tubular body 4 is formed inside the second shaft 8.

For example, the tank connection member 9 is formed of plastic, a resin, or the like and is attached to the second shaft 8. An O-ring 90 is provided between the tank connection member 9 and the second shaft 8 to ensure a tight fit between the tank connection member 9 and the second shaft 8. A communication hole 9*a* communicating with the communication hole 8*a* of the second shaft 8 is formed in an inner space of the tank connection member 9. The tank connection member 9 is connected to the tank 110 shown in FIGS. 1 and 2, and a vacuum generator 130 shown in FIGS. 1 and 2 is connected to the tank 110.

When the vacuum generator 130 generates negative pressure as the aspiration pressure, the negative pressure is applied to the tank, the communication hole 9*a* of the tank connection member 9, a hollow portion of the second tubular body 4, and a hollow portion of the first tubular body 3. The puncture tip section 2, the mantle 5, and the first tubular body 3 covered with the mantle 5 moves inside the medullary cavity perforated with the puncture tip section 2 by moving the entire bone marrow puncture unit 1 in the puncturing direction while rotating the second tubular body 4, the first tubular body 3, and the puncture tip section 2. In this stage, the bone marrow fluid is aspirated in a direction indicated by an arrow A by negative pressure through the opening 20*b* of the puncture tip section 2, the hollow portion of the first tubular body 3, the hollow portion of the second tubular body 4, and the communication hole 9*a* of the tank connection member 9 and is accumulated in the sterile tank 110 without exposing to the outside of the bone marrow puncture device 10 during the transfer, for example. Moreover, the anticoagulant is supplied to the bone marrow fluid immediately after the aspiration from the opening 20*b* of the puncture tip section 2 through the first tubular body 3. Thus, the bone marrow fluid is accumulated in the tank 110 without coagulation.

In the present embodiment, the opening 20b, the rear end opening 4a, and a connection member between the drug solution supply paths 5a and 6a may be sealed or covered with a sealing member such as a cap or a covering member such as a cover for example, in the state where the bone marrow puncture needle is detached from the first shaft 6, the gear 7, and the second shaft 8. Thus, the bone marrow puncture needle can be sterilized, for example. Therefore, the inside of the bone marrow puncture needle can be brought to aseptic conditions, and sterility of the bone marrow puncture system 100 can be maintained. Moreover, the opening of the tank 110 can be sealed or covered with a sealing member such as a cap or a cover member such as a cover. With this configuration, the tank 110 can be sterilized, for example, and the inside of the tank 110 and the surface of the cap can be brought to aseptic conditions and can be transferred to a treatment facility by placing a cover thereon after collection of the bone marrow fluid while maintaining the aseptic conditions.

Figure 23:
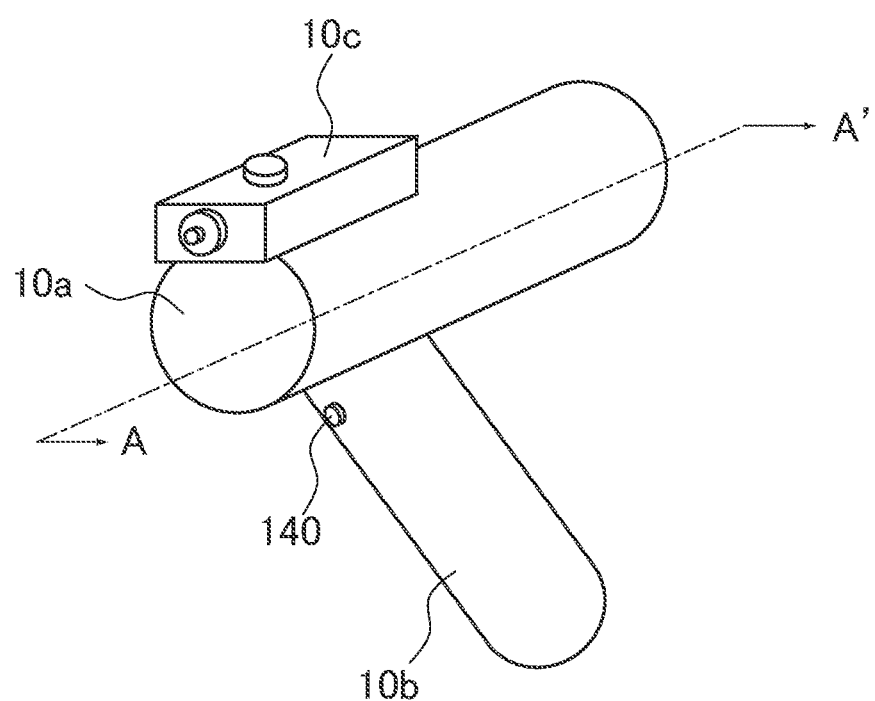
FIG. 23 is a perspective view showing a modification of a bone marrow puncture device.
Figure 24:
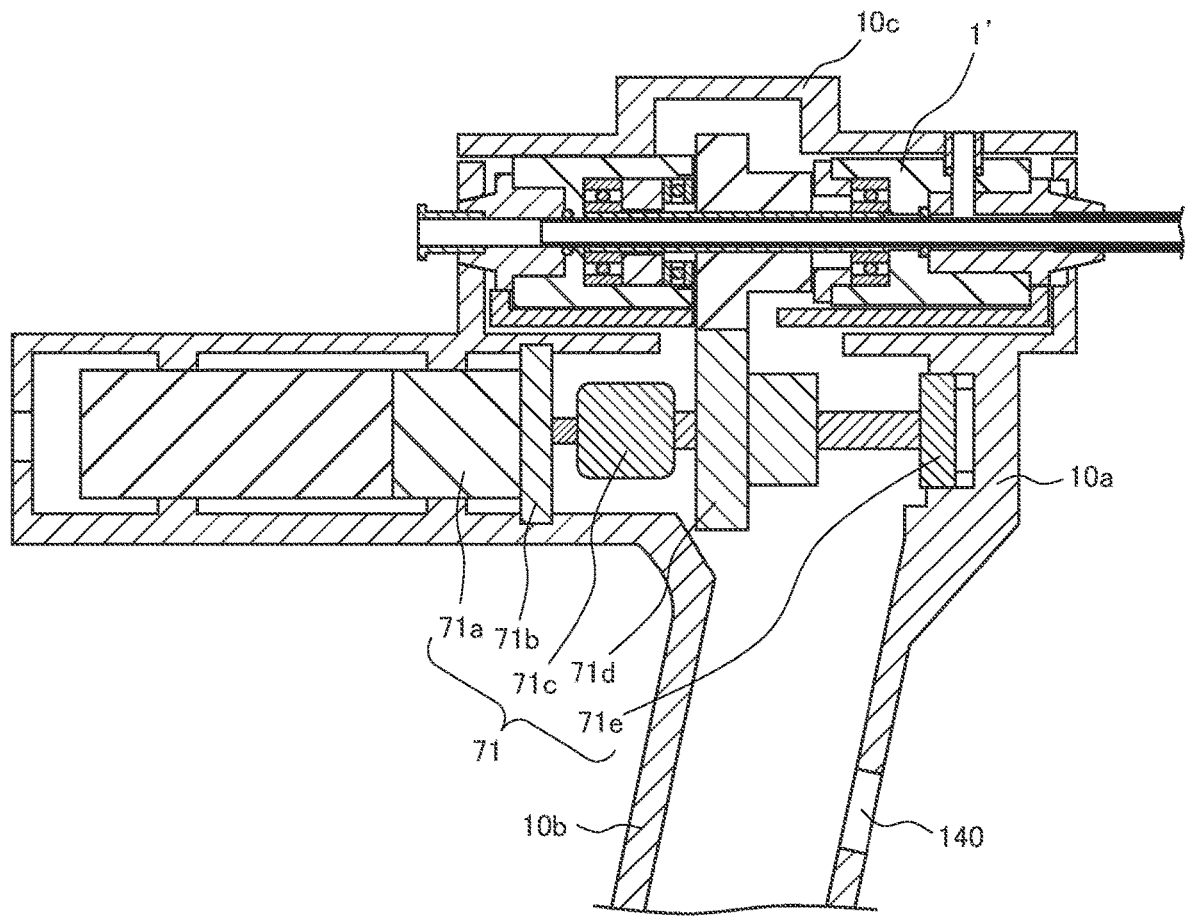
FIG. 24 is a cross-sectional view taken along the line A-A' of FIG. 23.
Figure 25:
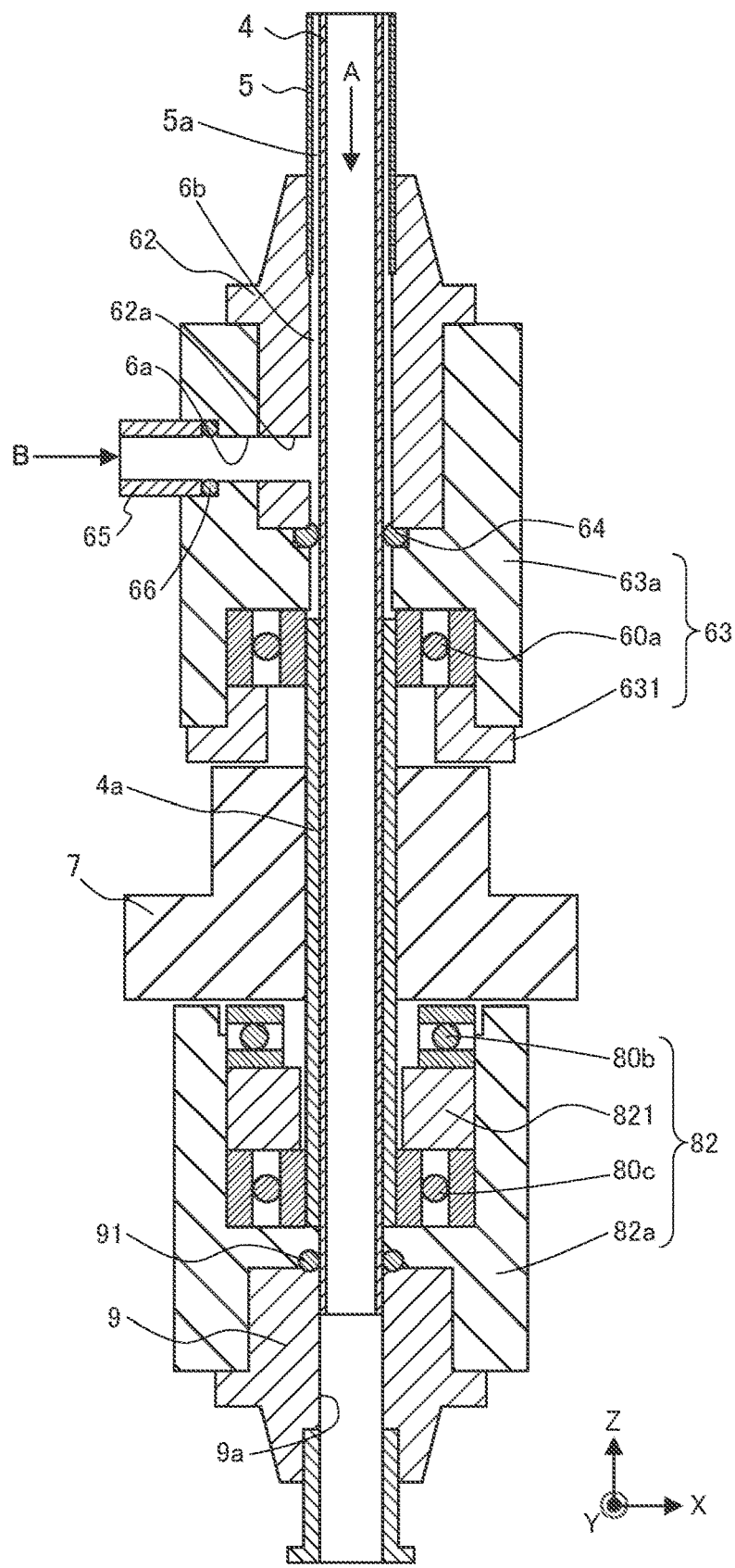
FIG. 25 is an enlarged view of a modification of the bone marrow puncture unit in FIG. 23.

The bone marrow puncture device 10 including the bone marrow puncture unit 1' of a modification is described below with reference to FIGS. 23, 24, and 25. FIG. 23 is a perspective view of the bone marrow puncture device 10. FIG. 24 is a cross-sectional view taken along the line A-A' of FIG. 23. FIG. 25 is an enlarged view of the bone marrow puncture unit 1' in FIG. 23. In FIGS. 23, 24, and 25, illustration of a magnetic sensor utilized in navigation to be mentioned later is omitted.

As shown in FIGS. 23 and 24, the bone marrow puncture device 10 includes a housing 10a, and a bone marrow puncture unit 1' to be mentioned later and a drive unit 71 including a motor 71a and the like are provided inside the housing 10a. A handle 10b is formed in the housing 10a so as to be easily operated by an operator. A switch unit 140 is provided on a handle 10b. An upper lid 10c is attached detachably to an upper part of the housing 10a. The bone marrow puncture unit 1' is detachable inside the housing 10a in the state where the upper lid 10c is removed from the housing 10a. Accordingly, when the first tubular body 3 or the second tubular body 4 of the bone marrow puncture unit 1' in the bone marrow puncture device 10 is clogged, the bone marrow puncture unit 1' can be easily replaced.

As shown in FIG. 24, the drive unit 71 includes a motor 71a, a motor fixing member 71b, a joint 71c, a gear 71d, and a radial bearing 71e. The motor 71a is fixed to a motor fixing member 71b formed of plastic, a resin, or the like by a fixing member such as a screw. The shaft of the motor 71a and the shaft of the gear 71d are connected by the joint 71c. The gear 71d is fixed by the gear fixing member using shaft tightening, and an shaft end is placed in a radial bearing 71e. With this configuration, when the motor 71a is rotated, the rotational force is propagated to the gear 71d via the joint 71c. The gear 71d fits in the gear 7 of the bone marrow puncture unit 1' and transfers the rotational force transferred from the motor 71a to the gear 7.

As shown in FIG. 25, the bone marrow puncture unit 1' includes a second tubular body 4, a mantle 5, a puncture connection member 62, a first bearing unit 63 corresponding to the first shaft 6, a gear 7, a second bearing unit 82 corresponding to the second shaft 8, and a tank connection member 9. The puncture tip section 2 of the bone marrow puncture unit 1' and the first tubular body 3 are not shown because of having the same configuration as the puncture tip section 2 of the bone marrow puncture unit 1 and the first tubular body 3.

For example, the puncture connection member 62 is formed of plastic, a resin, or the like and is attached detachably to the first bearing unit 63. An O-ring 64 is provided among the second tubular body 4, the puncture connection member 62, and the first bearing unit 63 to ensure a tight fit among the second tubular body 4, the puncture connection member 62, and the first bearing unit 63. That is, liquid tightness of the drug solution supply path 6b is ensured. A communication hole 62a communicating between the inlet 6a for a drug solution such as an anticoagulant and a hollow portion of the puncture connection member 62 is formed in the puncture connection member 62. A drug solution such as an anticoagulant is supplied from the syringe pump 150 as a drug solution supply section shown in FIGS. 1 and 2 to a communication hole 62a in a direction indicated by an arrow B through the inlet 6a. A drug solution supply path 6b is formed between the inner periphery of the puncture connection member 62 in the vicinity of the communication hole 62a and the outer periphery of the second tubular body 4, and the drug solution supply path 6b continues from the above-mentioned drug solution supply path 5a. Thus, a drug solution supplied from the inlet 6a is transferred to the outer periphery of the first tubular body 3 via the communication hole 62a and the drug solution supply paths 6b and 5a and is permeated from gaps between coil turns of the round wire of the first tubular body 3.

The first bearing unit 63 includes a first bearing housing 63a, a first radial bearing 60a, and a bearing holder 631. For example, the first bearing housing 63a is a non-rotation body formed of plastic, a resin, or the like and is attached to the outer periphery of the second tubular body 4 covered with a protective sheath 4a that is a protection member for a tube wall via the first radial bearing 60a. The first radial bearing 60a is held inside the first bearing housing 63a by the adjoining bearing holder 631. An inlet 6a is formed in the first bearing housing 63a and is connected to the syringe pump 150 via a connector 65 such as a luer rock connector, for example. An O-ring 66 is provided between the inlet 6a and the connector 65 to ensure a tight fit between the first bearing housing 63a and the connector 65. A washer or the like may be disposed between the first bearing housing 63a and the first radial bearing 60a and between the first radial bearing 60a and the bearing holder 631, to disperse the surface pressure, for example.

The gear 7 is, for example, formed of carbon steel, a metal such as stainless, plastic, a resin, or the like and fits in the outer periphery of the second tubular body 4 covered with a protective sheath 4 for protecting a pipe wall. A rotational force of the motor 71a is transferred to the gear 7 via a gear 71d of the drive unit 71, thereby rotating the second tubular body 4.

The second bearing unit 82 includes a second bearing housing 82a, a thrust bearing 80b, a second radial bearing 80c, and a bearing holder 821. For example, the second bearing housing 82a is a non-rotation body formed of plastic, a resin, or the like and is attached to the outer periphery of the second tubular body 4 covered with a protective sheath 4a via the second radial bearing 80c. The thrust bearing 80b is disposed inside the second bearing housing 82a. The thrust bearing 80b and the second radial bearing 80c are held inside the second bearing housing 82a by the adjoining bearing holder 821. A washer or the like may be disposed between the second bearing housing 82a and the second radial bearing 80c, between the second radial bearing 80c and the bearing holder 821, and between the thrust bearing 80b and the gear 7, to disperse the surface pressure, for example.

For example, the tank connection member 9 is formed of plastic, a resin, or the like and is attached detachably to the second bearing unit 82. An O-ring 91 is provided among the second tubular body 4, the tank connection member 9, and the second bearing unit 82 to ensure a tight fit between the tank connection member 9 and the second bearing unit 82. A communication hole 9a communicating with the second tubular body 4 is formed inside the tank connection member 9. The tank connection member 9 is connected to a tank 110 shown in FIGS. 1 and 2, and a vacuum generator 130 shown in FIGS. 1 and 2 is connected to the tank 110.

The bone marrow puncture unit 1' includes a first radial bearing 60a, a gear 7, a thrust bearing 80b, and a second radial bearing 80c. Thus, the drag to axial rotation in the direction for rotating the bone marrow puncture unit 1' is received by the first radial bearing 60a, the gear 7, and the second radial bearing 80c, which are attached indirectly to the second tubular body 4. The drag to the propulsive force of the bone marrow puncture unit 1' is received by the thrust bearing 80b. Thus, the bone marrow puncture unit 1' can receive each drag received during puncture through the entire bone marrow puncture unit 1', and the operation and the puncture can be performed more safely. The method for using the bone marrow puncture unit 1' is the same as the method for using the bone marrow puncture unit 1.

In the bone marrow puncture unit 1', different bearings are provided to receive the drag in the rotating direction (radial direction) and the drag in the propulsion direction (axial direction) generated at the time of puncturing, respectively. However, the present invention is not limited to this, and one bearing may be used to receive the drag in the rotating direction and the drag in the propulsion direction. Further, a lubricating bearing or the like may be used as the bearing.

In the bone marrow puncture unit 1', the rotational force of the drive unit 71 is transferred to the second tubular body 4 via the gear 7. However, the present invention is not limited to this, and the rotational force of the drive unit 71 may be directly propagated to the second tubular body 4. As a specific example, the motor 71a may directly rotate the second tubular body 4, for example.

Each opening and connection member of the bone marrow puncture unit 1' may be sealed or covered with a sealing member such as a cap or a covering member such as a cover, for example. Thus, the bone marrow puncture needle can be sterilized, for example. Therefore, the inside of the bone marrow puncture needle can be brought to aseptic conditions, and sterility of the bone marrow puncture system 100 can be maintained.

(Configuration of Guide Tube)

Figure 4A:
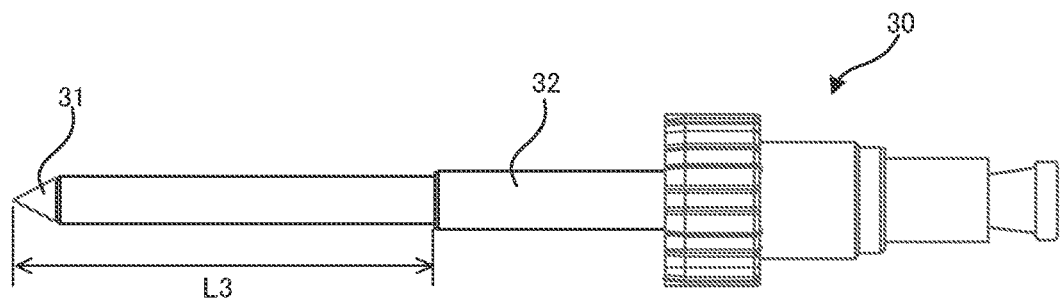
FIGS. 4A to 4E are drawings illustrating a guide tube.
Figure 4B:
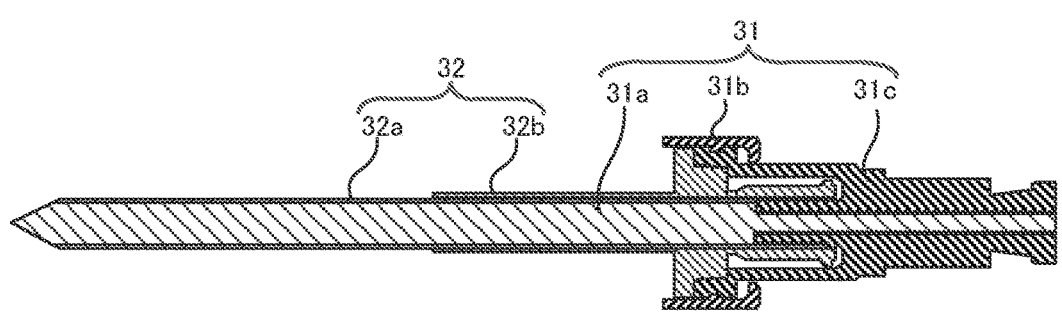
Figure 4C:
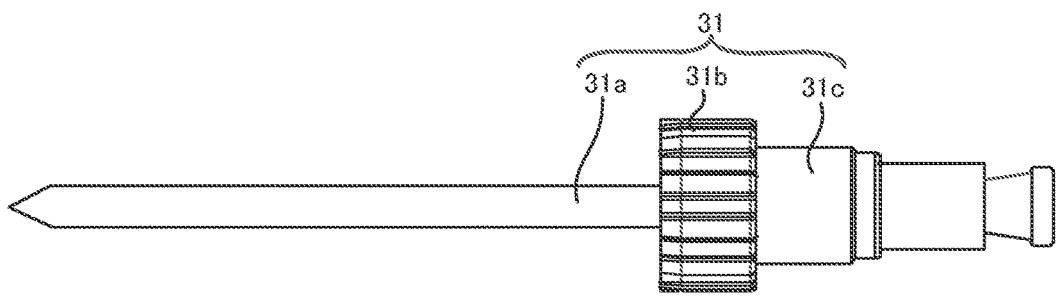
Figure 4D:
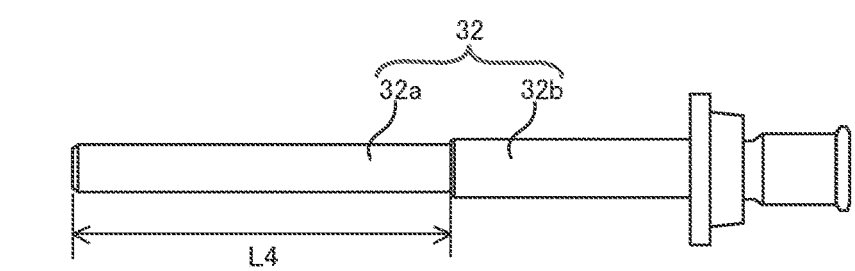
Figure 4E:
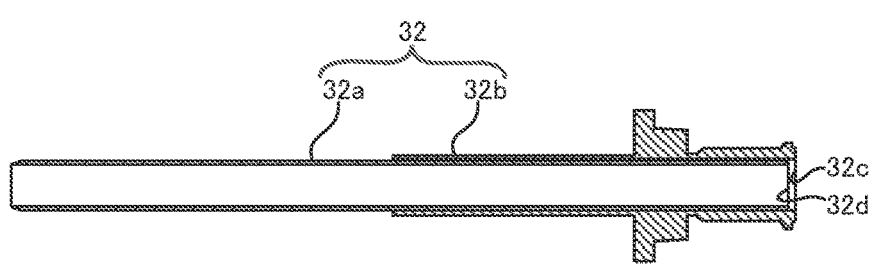

The configuration of the guide tube 30 is described below with reference to the drawings. FIGS. 4A to 4E are drawings illustrating a guide tube. FIG. 4A is a plan view illustrating the entire guide tube where an inner needle is inserted into an outer needle. FIG. 4B is a cross-sectional view of FIG. 4A. FIG. 4C is a plan view illustrating the outer needle. FIG. 4D is a plan view illustrating the inner needle. FIG. 4E is a cross-sectional view of FIG. 4D. In FIGS. 4A to 4E, a magnetic sensor used in navigation to be mentioned later is omitted.

In the bone marrow puncture system 100 according to the present embodiment, first, the guide tube 30 is inserted into the ilium or the like from above the skin of a donor, and then, a projection having a length L1 of the bone marrow puncture unit 1 is inserted into the hollow portion of the guide tube 30, thereby puncturing the bone marrow.

The guide tube 30 is configured by a combination of an inner needle 31 and an outer needle 32 as shown in FIGS. 4A and 4B. Semi-austenitic stainless steel is used as the material of the guide tube 30, for example. However, non-magnetic metal or high tensile steel may be used as the material of the guide tube 30. Non-metal may be used as the material of the guide tube 30.

As shown in FIGS. 4B and 4C, the inner needle 31 includes an inner needle member 31a, a ring member 31b, and an inner needle holder 31c. The inner needle member 31a is a rod-shaped body having a sharp tip and is supported by the inner needle holder 31c. The ring member 31b is rotatably attached to the inner needle holder 31c, and by rotating the ring member 31b, the inner needle 31 can be attached to and detached from the outer needle 32.

As shown in FIGS. 4B, 4D, and 4E, the outer needle 32 includes an outer needle portion 32a and an outer needle holder 32b. The outer needle holder 32b includes a hollow portion, and the outer needle portion 32a is supported within the hollow portion. The outer needle portion 32a is a hollow cylindrical body.

When the guide tube 30 is assembled, first, an inner needle member 31a is inserted from an opening 32c at the rear end of the outer needle holder 32b and an opening 32d at the rear end of the outer needle portion 32a shown in FIG. 4E. The outer needle holder 32b is then tightened by the inner needle holder 31c by rotating a ring member 31b, thereby assembling the guide tube 30 where the outer needle 32 and the inner needle 31 are integrated.

When the bone marrow is punctured, first, the guide tube 30 with the outer needle 32 and the inner needle 31 integrated therewith is inserted into the ilium or the like from above the skin of a donor. The number of revolutions of the inner needle 31 when the guide tube 30 is inserted into the ilium or the like is, for example, about 1000 rpm at maximum. A portion of the inner needle 31 inserted into the ilium or the like has a length L3 shown in FIG. 4A. Next, the ring member 31b is rotated to loosen the tightening of the outer needle holder 32b by the inner needle holder 31c and remove the inner needle 31 from the outer needle 32. Therefore, the inner needle 31 is placed in a state where the inner needle 31 is inserted into the ilium or the like. A portion of the inner needle 31 inserted into the ilium or the like has a length L4 shown in FIG. 4D. In this state, a projection having a length L1 of the bone marrow puncture unit 1 is inserted into the hollow portion of the outer needle portion 32a from the opening 32d at the rear end of the outer needle member 32a to puncture the bone marrow.

In the present embodiment, the bone marrow puncture unit 1 can be inserted at various angles from the guide tube 30 inserted from the same puncture hole (a hole in the skin) to puncture the bone marrow and collect a bone marrow fluid as mentioned below. Moreover, in the present embodiment, the guide tube 30 can be re-inserted into (can be used to re-puncture) the same puncture hole (hole in the cortical bone) at various angles to puncture another bone marrow and newly collect a bone marrow fluid.

(Configuration of Puncture Tip Section)

Figure 6:
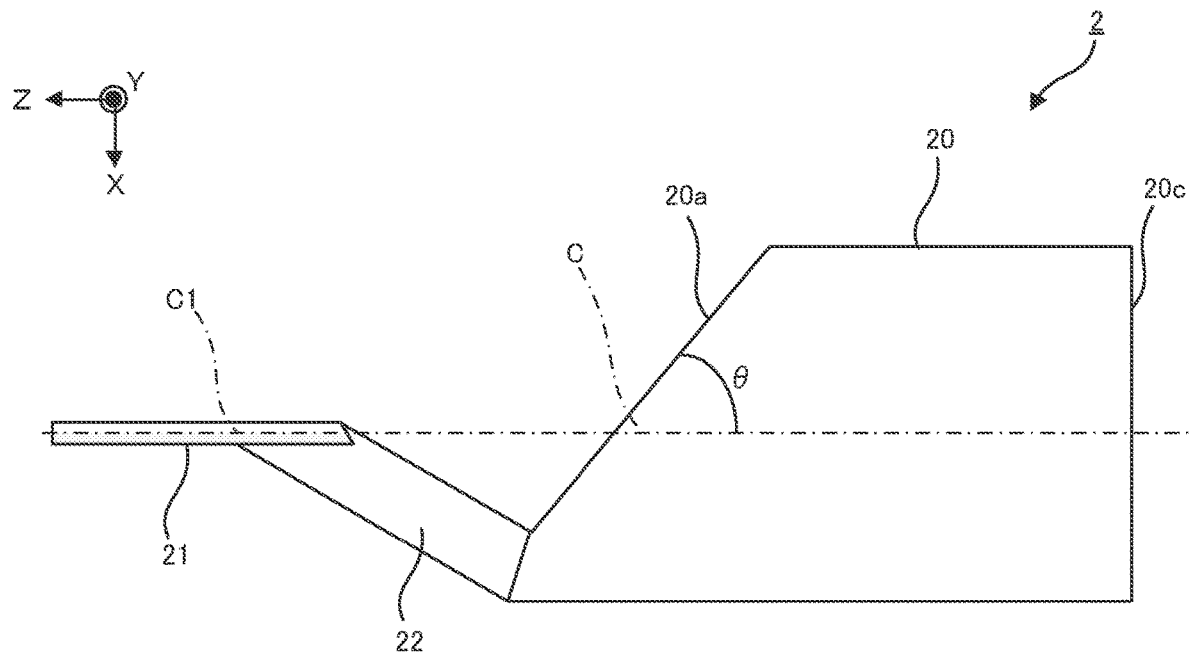
FIG. 6 is a side view illustrating the puncture tip section.
Figure 9A:
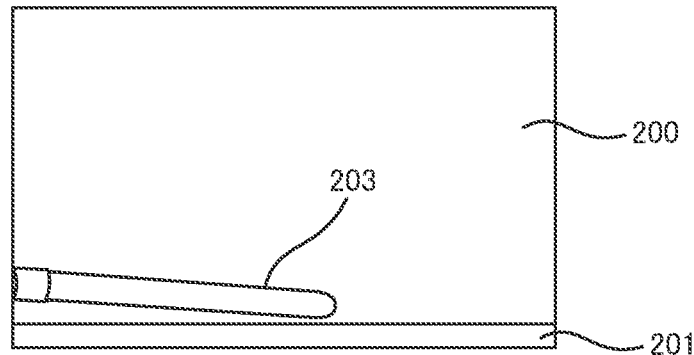
FIGS. 9A to 9C are drawings illustrating puncture marks when puncturing is performed using the bone marrow puncture unit according to an embodiment in a simulation using a plastic block having the same hardness as the cortical bone/cancellous bone of the human ilium.
Figure 9B:
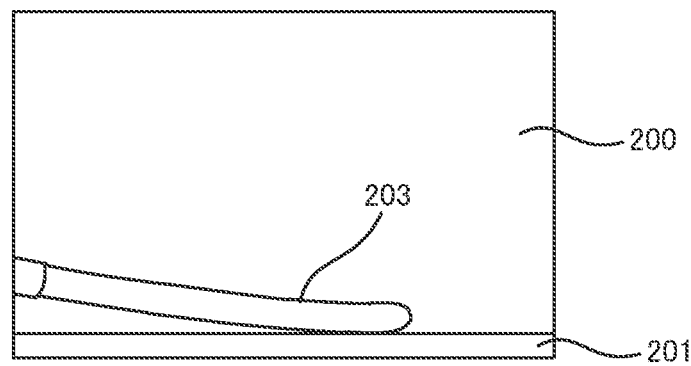
Figure 9C:
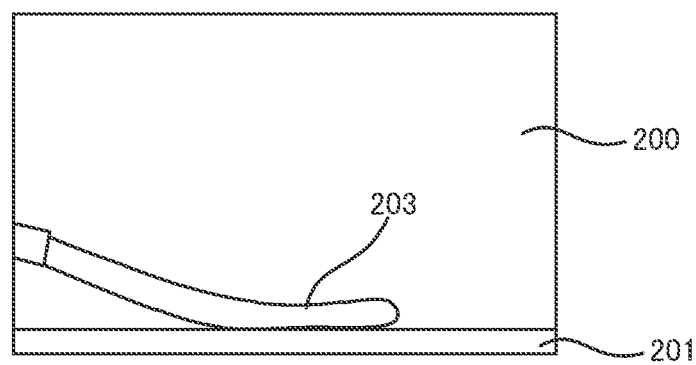

The puncture tip section 2 is described in details below with reference to the drawings. FIG. 5 is a perspective view illustrating the puncture tip section 2. FIG. 6 is a side view illustrating the puncture tip section 2. FIG. 7 is a plan view illustrating the puncture tip section 2. FIG. 8 is a front view illustrating the puncture tip section 2. FIGS. 9A to 9C are drawings illustrating puncture marks when puncturing is performed using the bone marrow puncture unit 1 according to the present embodiment in a simulation using a plastic block having the same hardness as the cortical bone/cancellous bone of the human ilium. FIG. 9A illustrates a puncture mark when puncturing is performed at an angle of entry of 5°. FIG. 9B illustrates a puncture mark at an angle of entry of 10°. FIG. 9C illustrates a puncture mark when puncturing is performed at an angle of entry of 15°.

The puncture tip section 2 includes, as mentioned above, a tube 20, a disc-shaped member 21, and a connection member 22. The tube 20 is a hollow cylindrical body. As shown in FIG. 6, the angle θ between the end surface 20a of the tube 20 and the central axis C of the tube 20 is set to an acute angle. In the present embodiment, the angle θ is set to, for example, 50° to 60°. As shown in FIGS. 5, 7, and 8, the end surface 20a includes an opening 20b intersecting the central axis C of the tube 20. In this way, since the opening 20b is formed in the end surface 20a such that the angle θ formed between the tube 20 and the central axis C becomes an acute angle, the opening 20b can be made larger than in the case where the opening is formed in the end surface perpendicular to the central axis C. As a result, a bone marrow fluid can be collected efficiently. Moreover, the opening 20b is formed in the puncture tip section 2 at a large size and at a single site. Thus, when the cancellous bone punctured with the puncture tip section 2 is aspirated into the tube 20, the negative pressure can be concentrated at the opening 20b to prevent clogging of the cancellous bone in the opening 20b. As a result, a bone marrow fluid can be collected efficiently.

As shown in FIG. 5, an opening 20d is formed in the rear end surface 20c of the tube 20. Thus, a bone marrow fluid passes through the opening 20b formed with a large size and is aspirated toward the first tubular body 3 side through the hollow portion and the opening 20d of the tube 20.

The disc-shaped member 21 has a radial central axis C1 that coincides with the central axis C of the tube 20. That is, the disc-shaped member 21 has a radial central axis C1 (in the Z direction) of the disc-shaped member 21 on the central axis C of the tube 20 and is positioned at the tip in the puncturing direction indicated by the arrow Z. The tube 20 rotates around the central axis C, e.g. counterclockwise or clockwise. However, since the radial central axis C1 of the disc-shaped member 21 coincides with the central axis C of the tube 20, smooth rotation is achieved without eccentricity. The tissue (e.g. the cancellous bone) in the medullary cavity is punctured by the rotation of the disc-shaped member 21. The minimum perforation hole (e.g. puncture hole) corresponding to the diameter R of the disc-shaped member 21 shown in FIG. 2 is formed by the non-eccentric rotation of the disc-shaped member 21. Moreover, the outer edge of the disc-shaped member 21, which is the tip in the puncturing direction, has an arc shape and does not include any sharp portion. Accordingly, the disc-shaped member 21 reaching the cortical bone does not damage to the cortical bone, and the disc-shaped member 21, which is the tip in the puncturing direction can be prevented from puncturing (perforating) from the inside of the medullary cavity to the outside. Moreover, the disc-shaped member 21 can perforate (puncture) the cancellous bone. Thus, with the puncture tip section 2, a bone marrow fluid can be efficiently collected also from the cancellous bone, for example. On the outer edge of the disc-shaped member 21, the disc-shaped surface and the side surface of the disc-shaped member 21 intersect with each other in the orthogonal direction. However, the present invention is not limited to this, and the outer edge of the disc-shaped member 21 may have R, i.e., a curved surface. With this configuration, the disc-shaped member 21 can maintain the perforating ability, and the outer edge of the disc-shaped member 21 does not have any sharp portion. Accordingly, the disc-shaped member 21 reaching the cortical bone does not damage the cortical bone, and the disc-shaped member 21, which is the tip in the puncturing direction can be more effectively prevented from puncturing (perforating) from the inside of the medullary cavity to the outside.

The shape of the disc-shaped member 21 as the tip rotation section is not limited to a partially-notched shape and may be a partially-notched elliptical plate or shape where a disc or an elliptical plate shape is combined with a plate with another shape as long as the shape of the tip in the puncturing direction is an arc shape. In addition to these shapes, the shape of the tip rotation section can be any of other various shapes. However, the extreme tip (distal end) surface preferably has a curved surface shape in order to prevent damage to the cortical bone, and the tip rotation section preferably has a plate shape which is thin in the direction perpendicular to the central axis C1 in order to improve the perforating ability (puncturing performance) of tissue in the medullary cavity.

As shown in FIG. 7, the diameter R of the disc-shaped member 21 is formed to be larger than the width W in the Y direction that is orthogonal to the central axis C of the tube 20. Thus, the first tubular body 3 covered with the tube 20, the mantle 5, and the mantle 5 can smoothly move to a perforation hole (puncture hole) formed by the disc-shaped member 21. The diameter R can be set, as appropriate, according to the inner diameter of the guide tube to be mentioned later, for example. The diameter R is, for example, around 8 gauge (G).

The tube 20 is an end portion of a tubular body, which continues from the second tubular body 4 and the first tubular body 3 and includes an opening 20b at the end surface 20a which is the surface at the distal end of the tubular body, as shown in FIGS. 5, 6, 7, and 8.

It is known that the bone marrow fluid can be collected only from the immediate vicinity of the aspiration point In the present embodiment, and the bone marrow fluid is aspirated from the opening 20b of the end surface (the surface at the distal end) 20a of the tubular body disposed behind the tip rotation section (disc-shaped member 21). The bone marrow fluid thus can be efficiently collected from a large area that has been perforated (punctured).

The angle θ formed between the end surface 20a and the central axis C of the tube 20 is not set to be perpendicular to each other but set to an acute angle. Thus, the opening 20b is not orthogonal to but intersects with the central axis of the tubular body (20, 3, 4). In the present embodiment, the angle θ is set to, for example, 50° to 60°.

In this way, the opening is formed in the end surface 20a such that the angle θ formed between the opening and the central axis C of the tubular bodies (20, 3, 4) is not set to be perpendicular but set to an acute angle. Thus, the opening 20b can be made larger than in the case where the opening is formed in the end surface perpendicular to the central axis C. As a result, a bone marrow fluid can be collected efficiently.

As shown in FIG. 5, an opening 20d is formed in the rear end surface 20c of the tube 20. Thus, a bone marrow fluid passes through the opening 20b formed with a large size and is aspirated toward the first tubular body 3 side through the hollow portion and the opening 20d of the tube 20.

As shown in FIGS. 5 and 7, a groove 22a that continues from the opening 20b of the tube 20 is formed in the connection member 22. Thus, the bone marrow perforated (punctured) by the disc-shaped member 21 is guided from the groove 22a to the opening 20b and is aspirated to the first tubular body 3 side by the negative pressure generated in the tube 20.

FIGS. 9A to 9C illustrate puncture marks when puncturing is performed using the bone marrow puncture unit 1 according to the present embodiment in a plastic block having the same hardness as the cortical bone/cancellous bone of the human ilium. In FIGS. 9A to 9C, the plastic block includes a foamed member 200 corresponding to the bone marrow and a laminated plate-shaped member 201 corresponding to the cortical bone. As shown in FIGS. 9A to 9C, it can be seen that the puncture mark 203 does not enter the laminated plate-shaped member 201 corresponding to cortical bone but is formed in the foamed member 200 when the angle of entry is any of 5 to 15°. In particular, as shown in FIG. 9C, it can be seen that the puncture mark 203 moves toward the laminated plate-shaped member 201 side at an angle at which the laminated plate-shaped member 201 enters, is then bent before the front surface of the laminated plate-shaped member 201, and moves along the surface of the laminated plate-shaped member 201 when the angle of entry is 15°. This is because the outer edge of the disc-shaped member 21 as the tip in the puncturing direction does not have any sharp portion, and the first tubular body 3 is formed into a coil shape and has flexibility.

Figure 20A:
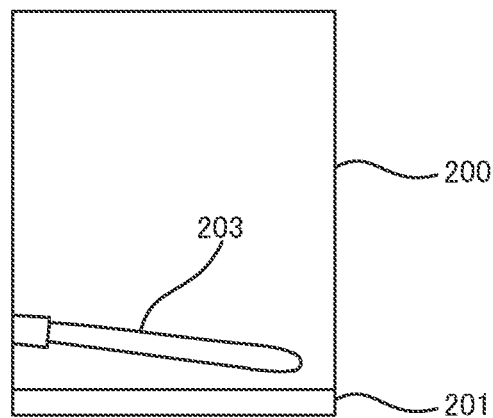
FIGS. 20A to 20C are drawings illustrating puncture marks when puncturing is performed using the bone marrow puncture unit according to a comparative example in a simulation using a plastic block having the same hardness as the cortical bone/cancellous bone of the human ilium.
Figure 20B:
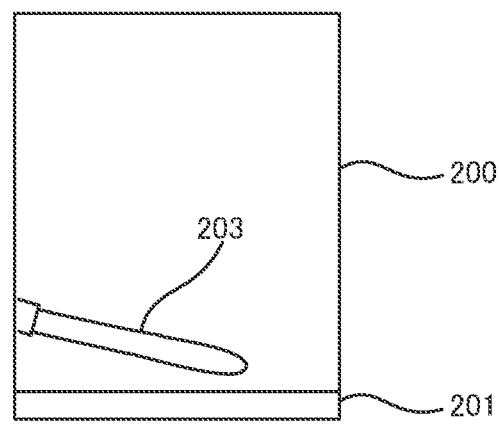
Figure 20C:
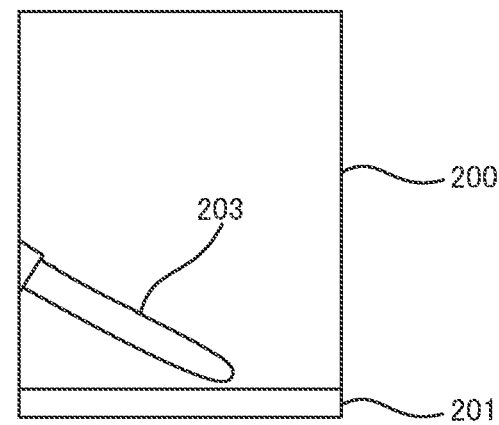

FIGS. 20A to 20C illustrate puncture marks when puncturing is performed in the same plastic block as shown in FIG. 9 using the bone marrow puncture unit according to the comparative example. FIG. 20A illustrates a puncture mark when puncturing is performed at an angle of entry of 5°. FIG. 20B illustrates a puncture mark at an angle of entry of 10°. FIG. 20C illustrates a puncture mark when puncturing is performed at an angle of entry of 20°. The bone marrow puncture unit according to the comparative example has a sharp puncture tip section, and all tubular bodies continuing to the puncture tip section were formed of a rigid body.

As shown in FIG. 20A, it can be seen that the puncture mark 203 does not enter the laminated plate-shaped member 201 when the angle of entry is 5°. However, as shown in FIGS. 20A and 20B, it can be seen that the puncture mark 203 moves toward the laminated plate-shaped member 201 side without being bent when the angle of entry is 10° and 20° C. Thus, it is understood that the tip in the puncturing direction may enter the laminated plate-shaped member 201 when the bone marrow puncture unit according to the comparative example moves forward.

As described above, in the present embodiment, the puncture tip section 2 of the bone marrow puncture unit 1 in the bone marrow puncture device is configured such that it includes a tube 20 that includes an opening 20b in the end surface 20a, a disc-shaped member 21 positioned at the tip in the puncturing direction, and a connection member 22 connecting between a part of the end surface 20a and the disc-shaped member 21. As a result, a bone marrow puncture device capable of efficiently aspirating the bone marrow fluid without puncturing (perforating) out the medullary cavity or the like by the tip in the puncturing direction can be provided. Moreover, in the present embodiment, the first tubular body 3 in the bone marrow puncture device (bone marrow puncture needle) is flexible. Therefore, the present embodiment is configured such that even if the puncture tip section 2 comes into contact with the cortical bone in the medullary cavity, the first tubular body 3 is bent. Thus, the risk of damage to the cortical bone caused by puncturing (perforating) with the tip in the puncturing direction from the inside of the medullary cavity to the outside can be reduced.

An opening that is different from the opening 20b may be provided in the side wall of the tube 20. It should be noted however that, in this case, the opening provided in the side wall is prone to be clogged due to a decrease in the negative pressure in the tube 20 or the like, and therefore, it is preferable to use only the opening 20b as an opening for collecting the bone marrow fluid from the viewpoint of aspirating the bone marrow fluid satisfactorily.

(Configurations of First Tubular Body and Drug Solution Supply Path)

Figure 10:
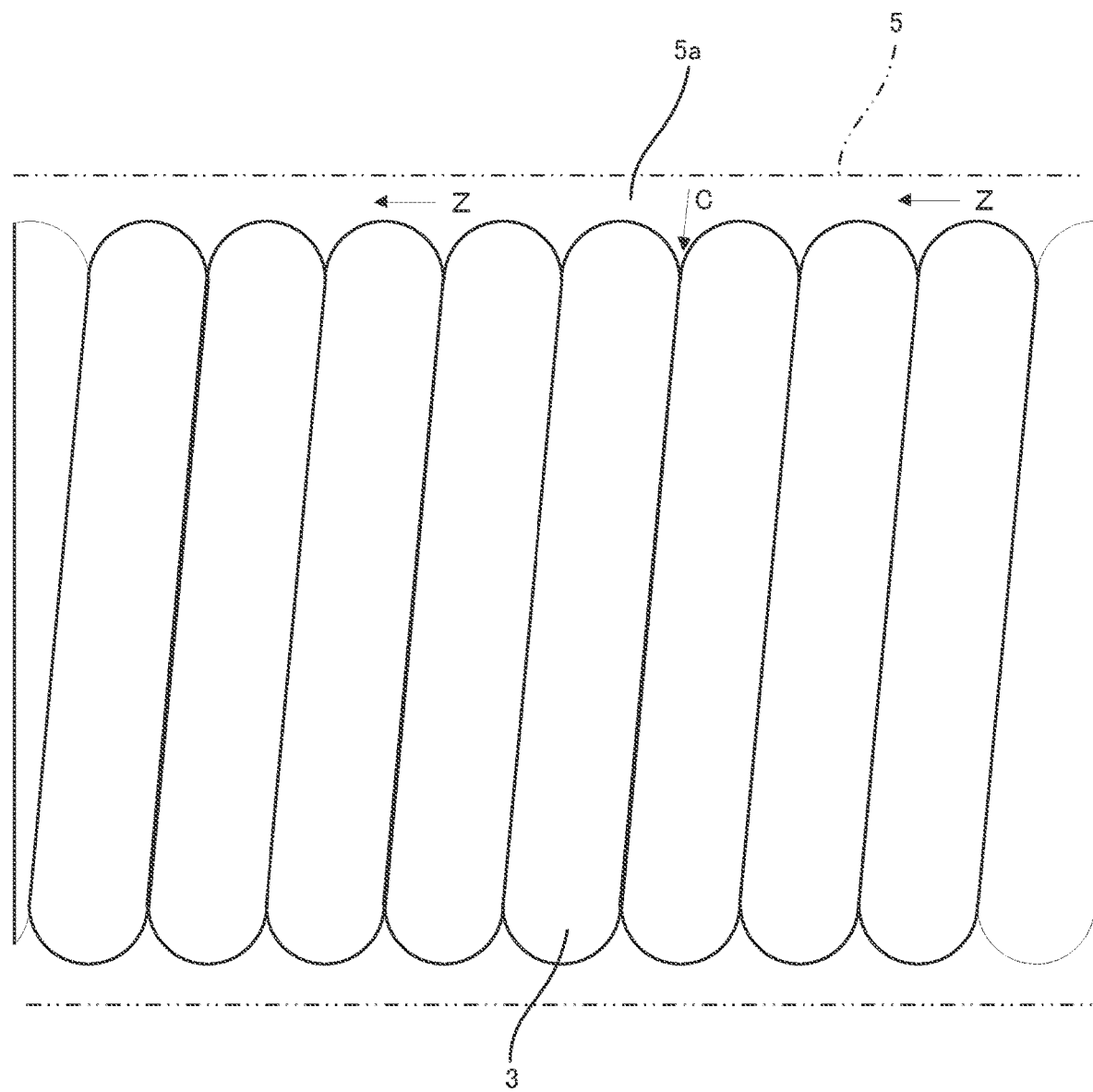
FIG. 10 is an enlarged side view of a portion of the first tubular body.
Figure 10:
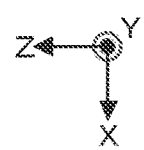

Next, the configurations of the first tubular body 3 and the drug solution supply path 5a will be described in detail. FIG. 10 is an enlarged side view of a portion of the first tubular body 3.

As shown in FIG. 10, the first tubular body 3 is formed by winding a round wire of stainless steel or the like into a coil shape, and the direction for winding the round wire agrees with the direction for rotating the first tubular body 3. Thus, the coiled round wire is rotated in the direction for tightening with rotation of the first tubular body 3. Accordingly, the outer diameter of the first tubular body 3 is not increased by the rotation. As a result, the first tubular body 3 can be rotated well within the mantle 5 while securing the drug solution supply path 5a between the first tubular body 3 and the mantle 5.

In the present embodiment, a syringe pump 150 shown in FIGS. 1 and 2 is connected to the inlet 6a of the first shaft 6 shown in FIG. 1, and an anticoagulant such as heparin is supplied, for example, at 40 μl/sec from the syringe pump 150. The anticoagulant supplied from the inlet 6a is transferred in the direction indicated by an arrow Z shown in FIG. 10 through the drug solution supply paths 6b and 5a and is supplied to the surface of the first tubular body 3.

The anticoagulant supplied to the surface of the first tubular body 3 enters gaps between coil turns of the round wire as indicated by the arrow C of FIG. 7 and is transferred in the direction indicated by an arrow Z along the direction for winding the coiled round wire. Some of the anticoagulant enters a hollow portion of the first tubular body 3 from gaps between coil turns of the round wire and is then mixed with a bone marrow fluid aspirated in the hollow portion. Further, in the vicinity of the connection member of the tube 20, the anticoagulant transferred in the direction indicated by the arrow Z enters the hollow portion of the first tubular body 3 from gaps between coil turns of the round wire and is then mixed with a bone marrow fluid immediately after the aspiration from the opening 20b of the tube 20. By rotation of the first tubular body 3 in a helical fashion, the bone marrow fluid immediately after the aspiration and the bone marrow fluid aspirated in the first tubular body 3 after the aspiration are efficiently mixed with the anticoagulant. Thus, the bone marrow fluid can be reliably prevented from coagulating.

As described above, the present embodiment is configured such that the first tubular body 3 is formed of the coiled round wire. Thus, the anticoagulant as a drug solution is permeable through the hollow portion of the first tubular body 3 from the surface of the first tubular body 3. Accordingly, an anticoagulant can be reliably supplied to the hollow portion of the first tubular body 3 that is used as an aspiration path of the bone marrow fluid without providing a tube or the like for supplying a drug solution. Therefore, the bone marrow fluid can be reliably prevented from coagulating while sufficiently securing the aspiration path for the bone marrow fluid without unnecessarily enlarging the perforation hole (puncture hole) for collecting the bone marrow fluid.

The present embodiment is configured such that the outer diameter of the first tubular body 3 is made smaller than the inner diameter of the mantle 5. Thus, the first tubular body 3 can be made rotatable inside the mantle 5, and the anticoagulant can be transferred to the vicinity of the tube 20 along the direction for winding the coiled round wire. Accordingly, the bone marrow fluid immediately after aspiration form the opening 20b of the tube 20 can be mixed with the anticoagulant, and the bone marrow fluid can be reliably prevented from coagulating.

The present embodiment is configured such that the outer diameter of the first tubular body 3 is made smaller than the inner diameter of the mantle 5. Accordingly, a drug solution supply path 5a can be provided between the outer peripheral surface of the first tubular body 3 and the inner peripheral surface of the mantle 5, and the anticoagulant can be reliably supplied to the surface of the first tubular body 3.

Moreover, the present embodiment is configured such that the mantle 5 also partially cover the rigid second tubular body 4 connected to the first tubular body 3, and the outer diameter of the second tubular body 4 is smaller than the inner diameter of the mantle 5. Accordingly, a drug solution supply path 5a can be provided also between the outer peripheral surface of the second tubular body 4 and the inner peripheral surface of the mantle 5, and the anticoagulant supplied from the inlet 6a can be reliably supplied to the surface of the first tubular body 3 from the drug solution supply path 5b.

As mentioned above, the negative pressure is generated by the pump in the hollow portion of the first tubular body 3. Thus, leakage of the anticoagulant from the opening 20b of the tube 20 to the outside does not occur.

Moreover, the first tubular body 3 is formed of a coiled round wire. Thus, the rotational force received from the second tubular body 4 can be reliably propagated to the tube 20, and a torque required in the tube 20 can be generated. Further, the present embodiment is configured such that the bone marrow puncture unit 1 is inserted into a guide tube called a trocar (not shown), and the first tubular body 3, a portion of the mantle 5 covering the first tubular body 3, and the puncture tip section 2 are only projected from the opening at the tip of the trocar. Thus, a portion of the bone marrow puncture unit 1 inserted into the medullary cavity is flexible due to the first tubular body 3 formed of a coiled round wire. Accordingly, as shown in FIGS. 9A to 9C, the puncture tip section 2 can be prevented from perforating the cortical bone or the like.

The present embodiment is described above with reference to an example where the first tubular body 3 is formed of a coiled round wire. The present invention, however, is not limited to such an example. Other configurations may be used if a material for forming a first tubular body 3 is a material through which a drug solution is permeable and which can reliably propagates a torque to the tube 20. For example, the first tubular body 3 may have a configuration where a round wire is woven or may be formed of a member having a permeation hole. However, the first tubular body 3 formed into a coil shape as in the present embodiment is preferable because it can assist transferring the drug solution to the tip region.

The present embodiment is described above with reference to an example where an anticoagulant is used as the drug solution. The present invention, however, is not limited to such an example. Drug solutions other than the anticoagulant can be used as needed.

The present embodiment is described above with reference to an example where the first tubular body 3 formed of a coiled round wire and the mantle 5 are used in a bone marrow puncture device. However, the first tubular body 3 and the mantle 5 can also be applied to other devices. For example, the first tubular body 3 and the mantle 5 can be provided inside a catheter or the like for collecting blood to supply a drug solution such as an anticoagulant.

The present embodiment is configured such that the mantle 5 partially covers the first tubular body 3 and the second tubular body 4. The present invention, however, is not limited to this configuration, and for example, the mantle 5 may partially cover only the first tubular body 3. However, the mantle 5 extending in the vicinity of the puncture tip section 2 is preferable because the drug solution can be efficiently supplied to the region where the treatment is performed by the puncture tip section 2.

Moreover, the present embodiment is configured such that the drug solution supply path 5a is formed by a gap between the mantle 5 and the first tubular body 3 and has a circular cross section in the direction perpendicular to the longitudinal direction of the first tubular body 3. However, the present invention is not limited to this configuration, and for example, the drug solution supply path may be a linear drug solution supply path provided in the mantle 5.

Figure 11:
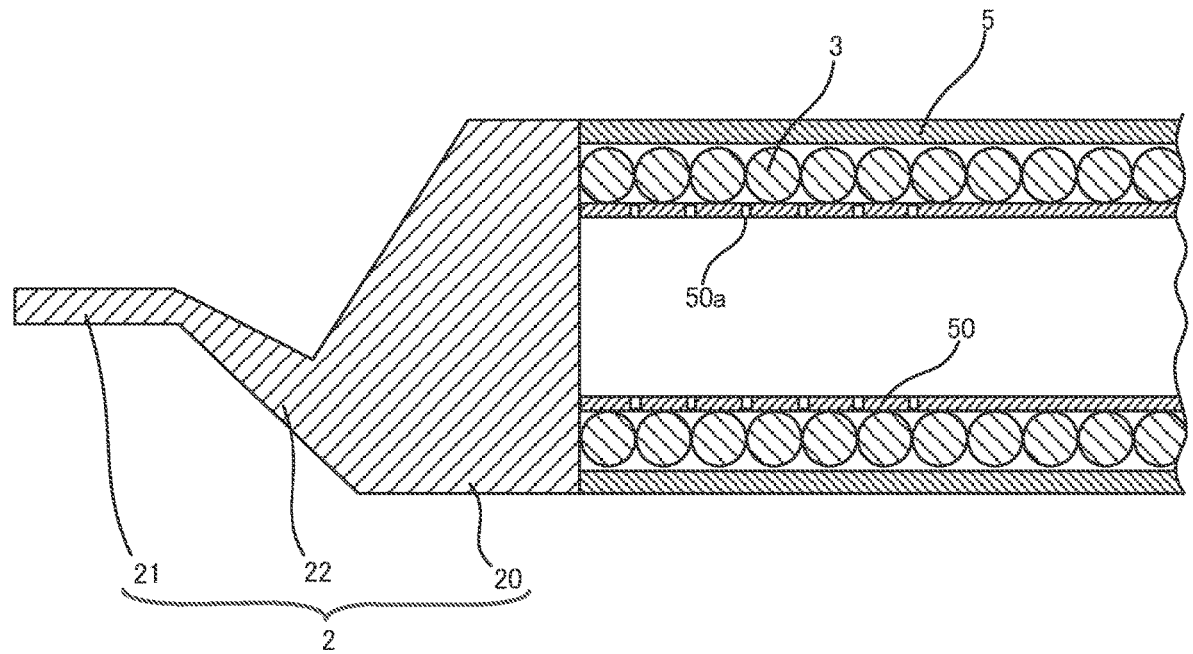
FIG. 11 is a cross-sectional view of a modification of the first tubular body.
Figure 12:
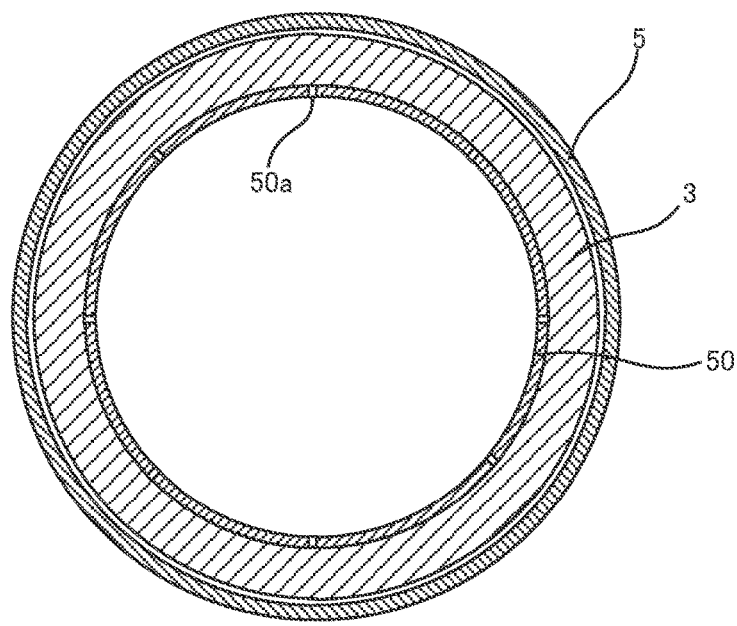
FIG. 12 is a front view of a modification of the first tubular body.

FIG. 11 is a cross-sectional view illustrating a modification of the first tubular body 3. FIG. 12 is a front view illustrating a modification of the first tubular body 3. As shown in FIGS. 11 and 12, an inner mantle 50 formed of a plastic such as PTFE, a resin, or the like may be provided on the inner periphery of the first tubular body 3. The inner mantle 50 is, for example, a flexible cylindrical tube. In this case, the first tubular body according to the present invention is configured by the first tubular body 3 and the inner mantle 50. In the case of this configuration, as shown in FIGS. 8 and 9A to 9C, an opening 50a may be formed in multiple sites of the inner mantle 50. Also in this case, the bone marrow fluid can be reliably prevented from coagulating while sufficiently securing the aspiration path for the bone marrow fluid without unnecessarily enlarging the perforation hole (puncture hole) for collecting the bone marrow fluid. Although an example of the case where an inner mantle 50 is provided on the inner periphery of the first tubular body 3 is taken, the inner mantle 50 may be provided as a first tubular body 3 as a substitute for the coiled first tubular body 3. In this case, the distal end of the inner mantle 50 is connected to, for example, the tube 20. Moreover, a space between the outer peripheral surface of the inner peripheral surface of the inner mantle 50 and the inner peripheral surface of the mantle 5 can be a drug solution supply path 5a.

The present embodiment is configured such that a drug solution supply path 5a is provided on the outer periphery of the first tubular body 3. The present invention, however, is not limited thereto, and the drug solution supply path 5a may not be provided. In this case, the first tubular body 3 preferably includes a drug placement portion on the inner periphery thereof, for example. For example, a mixture of a sustained-release property-imparting substance such as a gel, a polymer, or the like and a drug such at an anticoagulant is placed in the drug placement portion. It can also be said that the mixture is applied to the drug placement portion, for example. With this configuration, the drug placement portion can release the drug such as an anticoagulant from the drug placement portion at the time of aspiration of the bone marrow fluid. Thus, the drug solution supply paths 5a, 6a, and 6b and the syringe pump 150 can be omitted, for example. Accordingly, the configuration of the bone marrow puncture device 10 can be simplified.

Table 1 shows results obtained by collecting bone marrow fluids from the ilia of pigs using the bone marrow puncture device 10 including the bone marrow puncture unit 1 and the drug solution supply path 5a according to the present embodiment. In Table 1, the conventional method refers to a method where a mass-produced puncture needle is inserted from a hole made in the ilium, and a bone marrow fluid is aspirated from the tip of the puncture needle and is not a method where a bone marrow fluid is aspirated while moving the tip of the puncture tip forward as in the present embodiment.

In Table 1, the proportion of the number of cells in the CD34+ region and the CD45dim region refers to a value of the proportion of the number of cells in the CD34+ region and the CD45dim region in the lymphocyte and monocyte fraction (MNC fraction) of the collected bone marrow fluid. As can be seen from the results, according to the bone marrow puncture unit 1 and technique according to the present embodiment, the proportion of the number of cells in the CD34+ region and the CD45dim region, which can be a marker of hematopoietic stem cells, can be improved. That is, according to the bone marrow puncture unit 1 and the technique according to the present embodiment, the proportion of the hematopoietic stem cells required for transplantation of the bone marrow can be improved, and the bone marrow fluid can be efficiently collected. Therefore, for example, with the bone marrow puncture unit 1 and the technique according to the present embodiment, the time required for the collection can be shortened, and the number of times the perforation (puncturing) is performed can be reduced. Thus, the invasiveness to the donor can be greatly reduced, and a bone marrow fluid can be collected with local anesthesia.

TABLE 1

| Bone marrow collecting method | The amount of bone marrow fluid (mL) | The number of cells in CD34+ region and CD45dim region (×10⁵/mL) |
|---|---|---|
| Pig 1 Conventional method (six sites) | 34 | 1.6 |
| The present embodiment (four routes) | 108.5 | 4.9 |
| Pig 2 Conventional method (six sites) | 21 | 2.9 |
| The present embodiment (four routes) | 83.8 | 5.3 |
| Pig 3 Conventional method (three sites) | 15 | 0.8 |
| The present embodiment (four routes) | 64.4 | 5.2 |

Moreover, in the same manner as in Table 1, the amount of bone marrow fluid obtained from each of left and right ilia of one pig by each of the conventional method and the method according to the present embodiment, the total white blood cell (WBC) count, and the total number of CD34+ and CD45dim cells were compared. Table 2 shows the results of these.

TABLE 2

| | Bone marrow collecting method | The amount of bone marrow fluid (mL) | Total WBC (×10⁹) | CD34+, CD45dim (×106/mL) |
|---|---|---|---|---|
| Pig 1 | Conventional method (left and right ilia, six sites) | 17 | 0.6 | 4 |
| | The present embodiment Left ilium (four sites) | 42.5 | 1.4 | 31 |
| | Right ilium (four sites) | 100 | 3.2 | 35 |
| | Total (left and right ilia) | 142.5 | 4.6 | 66 |
| Pig 2 | Conventional method (left and right ilia, six sites) | 12.5 | 0.4 | 6 |
| | The present embodiment Left ilium (four sites) | 60 | 3.7 | 111 |
| | Right ilium (four sites) | 60 | 2.4 | 56 |
| | Total (left and right ilia) | 120 | 6.1 | 164 |

Among cell therapies, transplantation of hematopoietic stem cells requires the largest amount of bone marrow fluid and the highest number of stem cells. The number of CD34+ and CD45dim hematopoietic stem cells contained in 120 to 140 mL of bone marrow fluid collected by the collecting method using the bone marrow puncture device 10 including the bone marrow puncture unit 1 and the drug solution supply path 5a were comparable to the average value of $89.6 \pm 76.1 (\times 10^6)$ of hematopoietic stem cells contained in the average value of $927 \pm 163$ mL of human iliac bone marrow fluid collected by the conventional method. With the bone marrow puncture device 10 including the bone marrow puncture unit 1 and a drug solution supply path 5a, the number of hematopoietic stem cells required for transplantation of hematopoietic stem cells can be obtained from much less amount of bone marrow fluid, as compared with the conventional method. The amount of bone marrow fluid obtained by a single puncturing with the bone marrow puncture device 10 including the bone marrow puncture unit 1 and the drug solution supply path 5a is 15 to 20 mL, which does not widely vary. Thus, the amount of the bone marrow fluid to be collected can be adjusted by adjusting the number of times the puncturing is performed. The time required for the collection was about 2 minutes. The total time required for puncturing both ilia 8 to 10 times was 17 to 20 minutes. Thus, the collection could be performed in a very short time.

The bone marrow fluids obtained in Table 2 were subjected to colony forming unit-fibroblast (CFU-F) assay. Table 3 shows the results of these.

TABLE 3

| | Bone marrow collecting method | CFU-F/WBC (10⁷) | CFU-F/bone marrow fluid (mL) |
|---|---|---|---|
| Pig 1 | Conventional method | 24 | 79 |
| | Present embodiment | 320 | 1024 |
| Pig 2 | Conventional method | 85 | 264 |
| | Present embodiment | 515 | 2627 |

As shown in Table 3, each bone marrow fluid collected by the collecting method using the bone marrow puncture device 10 showed CFU-F colonies 6 to 13 times as many as each bone marrow fluid collected by the conventional method. These results demonstrate that the bone marrow fluid collected by the collecting method using the bone marrow puncture device 10 not only contains hematopoietic stem cells at high concentration but also contains mesenchymal stem cells at high concentration compared with the bone marrow fluid collected by the conventional method.

(Navigation)

Figure 13:
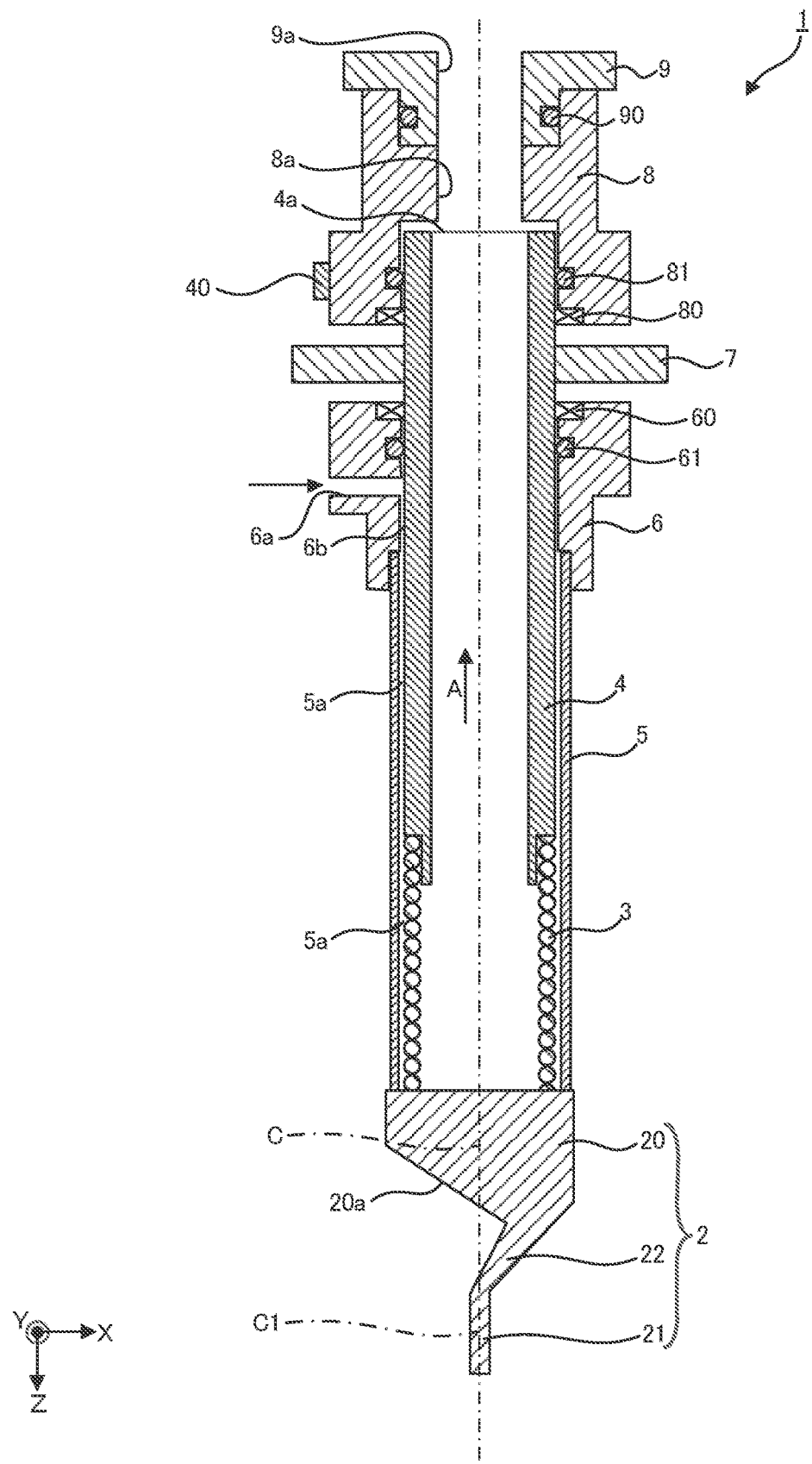
FIG. 13 is another cross-sectional view schematically illustrating a bone marrow puncture unit in the bone marrow puncture device.
Figure 14:
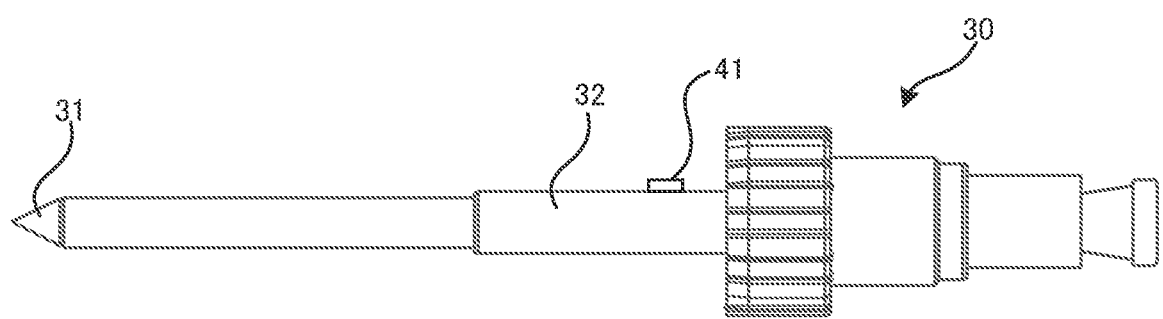
FIG. 14 is a plan view illustrating a guide tube.
Figure 15:
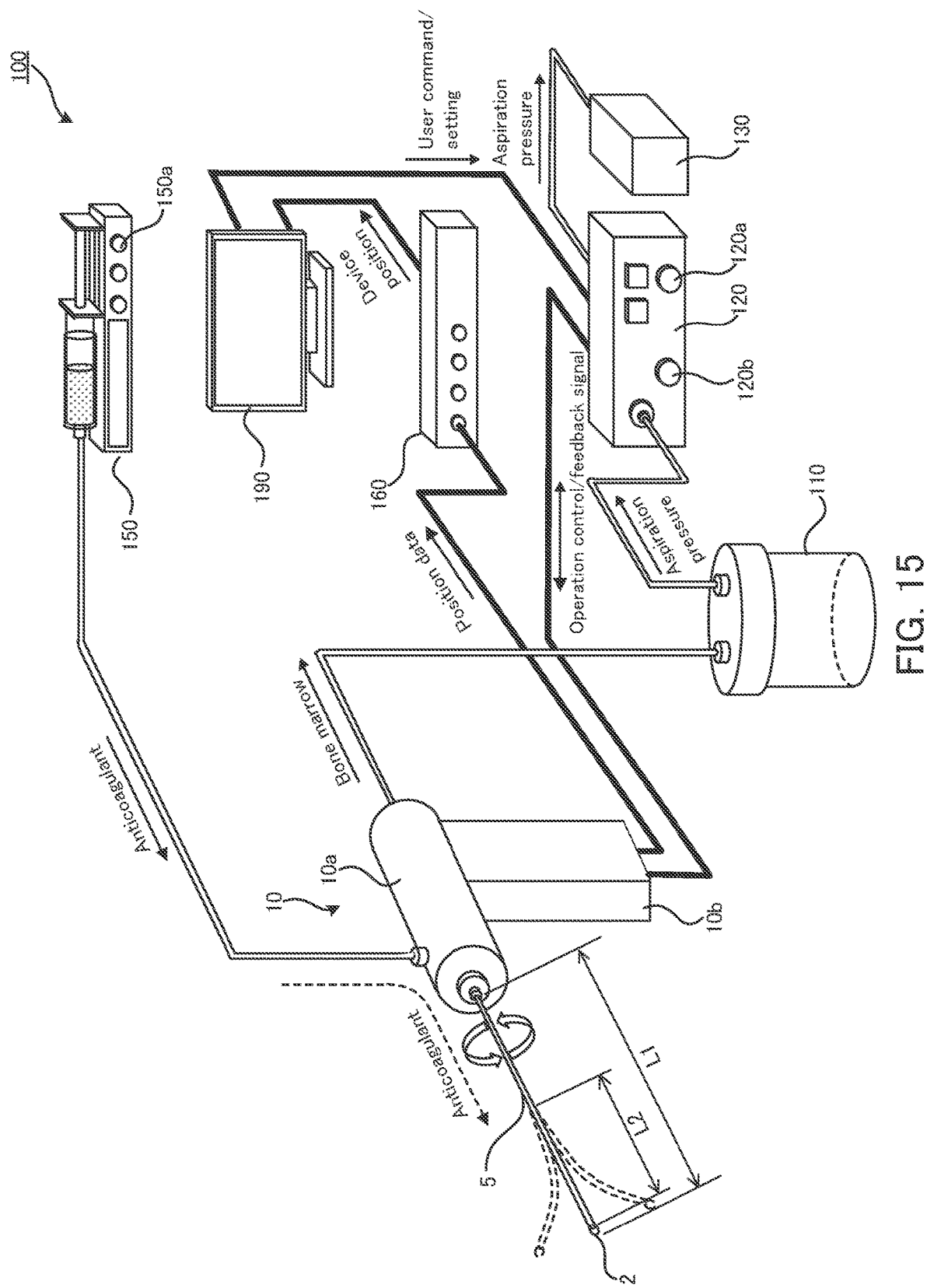
FIG. 15 is a drawing schematically illustrating a bone marrow puncture system.
Figure 16:
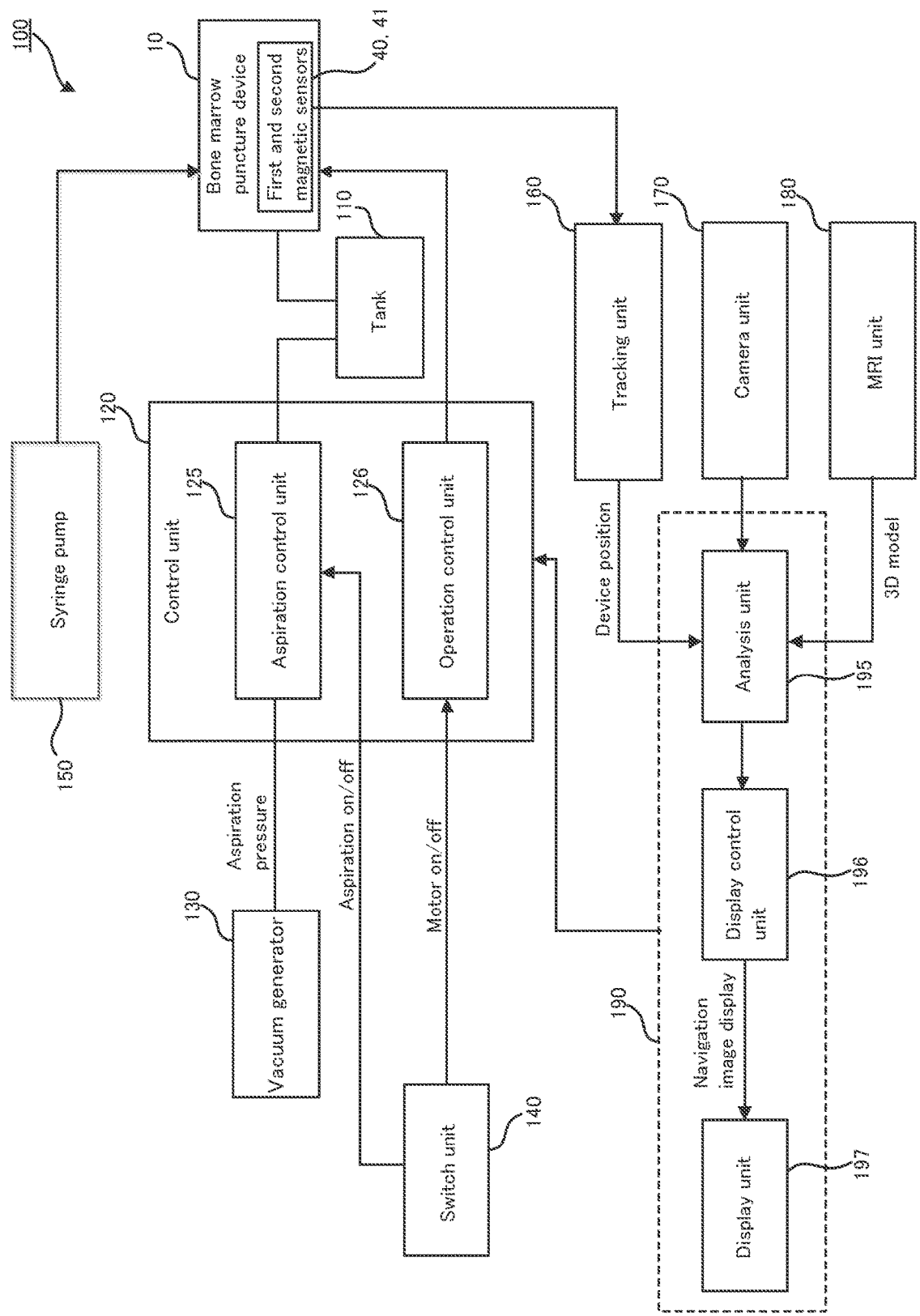
FIG. 16 is a block diagram illustrating a configuration of the bone marrow puncture system.
Figure 17:
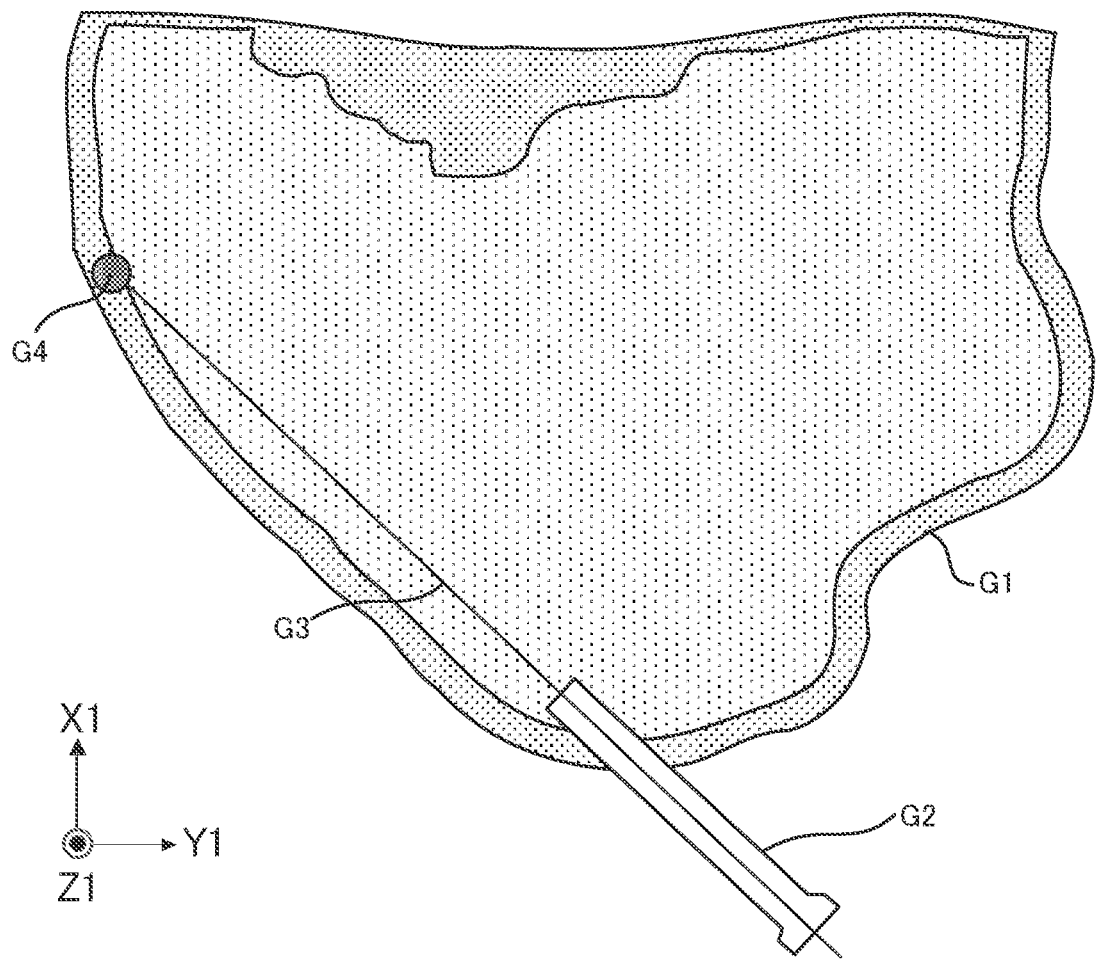
FIG. 17 is a drawing illustrating navigation in a bone marrow puncture system.
Figure 18:
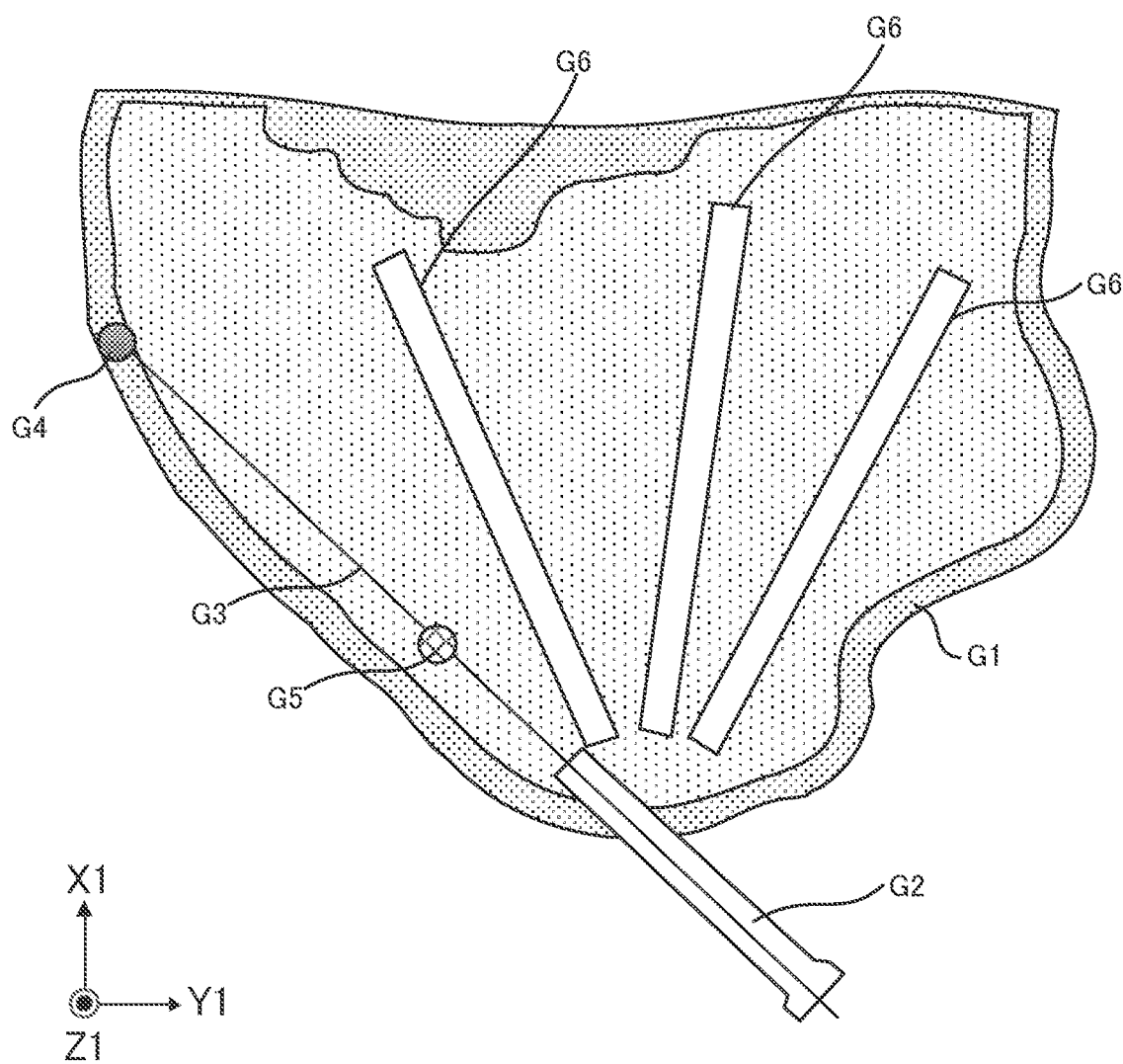
FIG. 18 is another drawing illustrating navigation in a bone marrow puncture system.
Figure 19:
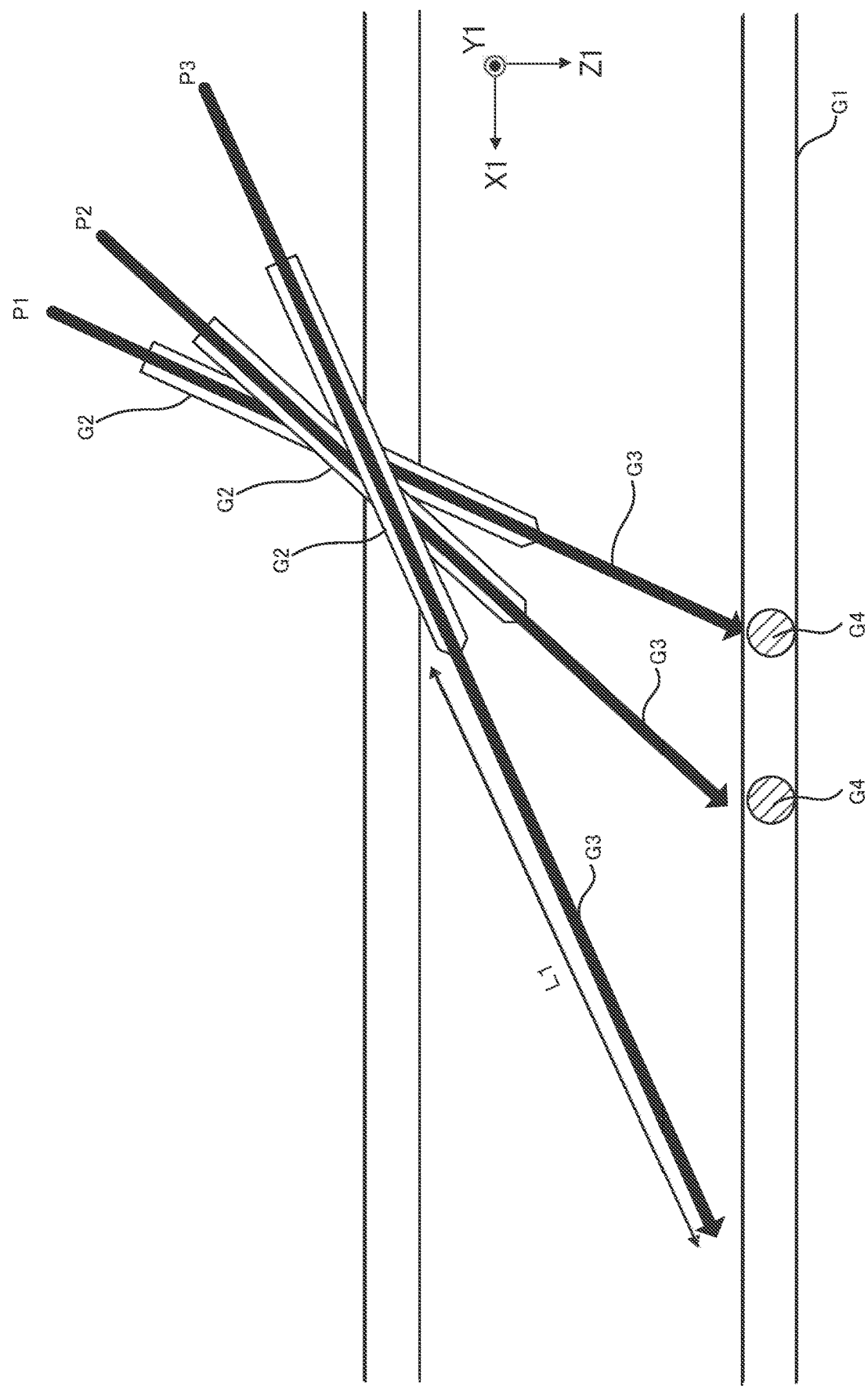
FIG. 19 is yet another drawing illustrating navigation in a bone marrow puncture system.

The configuration of the navigation will be described with reference to the drawings. FIGS. 13 to 19 are drawings for explaining the navigation. FIG. 13 is a cross-sectional view schematically illustrating a bone marrow puncture unit 1 in the bone marrow puncture device 10. FIG. 14 is a plan view illustrating the guide tube 30. FIG. 15 is a drawing schematically illustrating the bone marrow puncture system 100. FIG. 16 is a block diagram illustrating a configuration of the bone marrow puncture system 100. FIGS. 17 to 19 are schematic views for explaining operation of the navigation in the bone marrow puncture system.

In the present embodiment, as shown in FIG. 13, a first magnetic sensor 40 is attached to a second shaft 8 of a bone marrow puncture unit 1. Moreover, as shown in FIG. 14, a second magnetic sensor 41 is attached to the outer needle portion 32a of the guide tube 30.

The bone marrow puncture system 100 shown in FIGS. 15 and 16 differs from the bone marrow puncture system 100 shown in FIGS. 1 and 2 in that it includes a tracking unit 160, a camera unit 170, and an MRI unit 180 connected to the first magnetic sensor 40 and the second magnetic sensor 41. The camera unit 170 and the MRI unit 180 are not shown in FIG. 15. In the bone marrow puncture system 100 shown in FIGS. 15 and 16, the PC 190 functions as a display control unit 196 and a display unit 197.

The tracking unit 160 is connected to the first magnetic sensor 40 attached to the bone marrow puncture device 10 and the second magnetic sensor 41 attached to the guide tube 30 and receives position and angle data output from the first magnetic sensor 40 and the second magnetic sensor 41. The tracking unit 160 converts the received position and angle data into position and angle data displayable on the PC 190. The tracking unit 160 is connected to the PC 190 and sends the converted position and angle data to the PC 190.

The camera unit 170 takes images of the periphery of the ilium of a donor who is subjected to puncturing of the bone marrow. For example, three markers are attached to the periphery of the donor's ilium, and the location where bone marrow puncture is performed is surrounded by the markers. The camera unit 170 takes images of these markers and the location surrounded by the markers. The camera unit 170 is connected to the PC 190 and sends the taken images to the PC 190.

The MRI unit 180 creates a three-dimensional (3D) model of the ilium and the like based on the MRI images of the ilium and the like of the donor who is subjected to puncturing of the bone marrow, obtained by nuclear Magnetic Resonance Imaging. The MRI images are taken with markers attached to the periphery of the ilium and the like as mentioned above, and images of the markers are also taken as MRI images. The positions of the markers can be checked in the 3D model of the ilium and the like. The MRI unit 180 is connected to the PC 190 and sends the 3D model data of the ilium and the like to the PC 190.

The PC 190 functions as an analysis unit 195, a display control unit 196, and a display unit 197. The analysis unit 195 functions as a position calculation unit that calculates the position of the puncture tip section 2 on the basis of the output of the first magnetic sensor 40. The analysis unit 195 functions as a prediction unit that predicts the trajectory of the puncture tip section 2 and the contacting position of the puncture tip section 2 with the cortical bone on the basis of the output of the second magnetic sensor 41. The analysis unit 195 further functions as a moving rate calculation unit that calculates the moving rate of the puncture tip section 2 on the basis of the temporal change of the position of the puncture tip section 2 calculated by the function of the position calculation unit. The analysis unit 195 also functions as a recording unit that records the past trajectory of the puncture tip section 2 based on the position of the puncture tip section 2 calculated by the function of the position calculation unit.

The display control unit 196 successively displays a position of the puncture tip section 2 calculated by the analysis unit 195 on the display unit 197. The display control unit 196 displays a past trajectory of the puncture tip section 2 recorded on the analysis unit 195 that functions as a recording unit on the display unit 197. The display control unit 196 further displays the trajectory of the puncture tip section predicted by the analysis unit 195 that functions as a prediction unit and a contacting position of the puncture tip section 2 with the cortical bone on the display unit 197. The display control unit 196 also functions as a moving rate notification unit configured to notify a moving rate of the puncture tip section 2 calculated by the analysis unit 195 that functions as a moving rate calculation unit.

The display unit 197 is a display such as a liquid crystal display and displays the position of the puncture tip section 2, the past trajectory, the predicted trajectory, the predicted contacting position of the puncture tip section 2 with the cortical bone, the moving rate of the puncture tip section 2, and the like.

Next, navigation of the bone marrow puncture system 100 according to the present embodiment will be described. An example of collecting the bone marrow from the ilium of a donor is taken. An image of the donor's ilium was taken in advance by MRI, and the three markers mentioned above are affixed to the skin around the puncture site. The markers are reflected in the MRI image.

A 3D model of the ilium of the taken MRI image of the ilium is created by the MRI unit 180. This 3D model includes the markers. The 3D model of the ilium is sent from the MRI unit 180 to the PC 190 in advance.

In the case of puncturing the bone marrow, an image of a predetermined area including the sites around which the markers are affixed is taken by a camera unit 170, and the taken image is sent from the camera unit 170 to the PC 190. The analysis unit 195 of the PC 190 associates the 3D model of the ilium that has been received in advance with the image taken by the camera unit 170. In the association, the markers of the 3D model matches the markers of the image taken by the camera unit 170.

Next, the operator inserts the tip of the guide tube 30 where an inner needle 31 and an outer needle 32 are integrated, into the ilium from predetermined sites in an area surrounded by the markers on the skin, and the inner needle 31 is then removed such that the outer needle 32 is placed in the ilium. At that time, position and angle data sent from the second magnetic sensor 41 attached to the guide tube 30 are converted into displayable position and angle data by the tracking unit 160, and the displayable position and angle data are sent to the PC 190. The analysis unit 195 of the PC 190 superimposes an image data of the guide tube 30 on the 3D model on the basis of the received position and angle data regarding the guide tube 30. Further, the analysis unit 195 creates image data of predicted trajectory of the puncture tip section 2 in the bone marrow puncture unit 1 and image data of a predicted contacting position of the puncture tip section 2 with the cortical bone on the basis of the position and angle data of the guide tube 30 and superimposes these data on the image data. The analysis unit 195 outputs the image data created in the above-described manner to the display control unit 196. The display control unit 196 displays an image on the display unit 197 on the basis of the input image data.

FIG. 17 is a drawing illustrating an example of an image displayed on the display unit 197. In FIG. 17, a 3D model image G1 of the ilium, an image G2 corresponding to the outer needle 32 of the guide tube 30, an image G3 of a predicted trajectory of the puncture tip section 2, and an image G4 of a predicted contacting position of the puncture tip section 2 with the cortical bone are displayed.

As described above, in the present embodiment, the image G3 of a predicted trajectory of the puncture tip section 2 is displayed on the 3D model image G1 of the ilium. Thus, the operator can check the predicted trajectory of the puncture tip section 2 in a medullary cavity inside the ilium in which an ultrasound device is difficult to be used. When the predicted trajectory displayed is not positioned at a desired site, the operator changes an angle of the outer needle 32 of the guide tube 30, and a novel image G3 of a predicted trajectory of the puncture tip section 2 is then displayed. Thus, the operator can puncture the bone marrow in a desired trajectory with reference to these images.

When the operator checks the predicted trajectory of the puncture tip section 2 and determines that the bone marrow is punctured along this predicted trajectory, a projection with a length L1 of the bone marrow puncture device 10 is inserted into a hollow portion of the outer needle 32 of the guide tube 30. At that time, position and angle data sent from the first magnetic sensor 40 attached to the bone marrow puncture unit 1 of the bone marrow puncture device 10 are converted into displayable position and angle data by the tracking unit 160, and the displayable position and angle data are then sent to the PC 190. The analysis unit 195 of the PC 190 superimposes an image data of the position of the puncture tip section 2 in the bone marrow puncture unit 1 on the 3D model on the basis of the received position and angle data of the bone marrow puncture unit 1. In the present embodiment, the first magnetic sensor 40 is attached to the second shaft 8, and the length from the position at which the first magnetic sensor 40 is attached to the puncture tip section 2 is known. Thus, the position of the puncture tip section 2 can be calculated on the basis of the position and angle data. The analysis unit 195 outputs the image data created in the above-described manner to the display control unit 196. The display control unit 196 displays an image on the display unit 197 on the basis of the input image data.

FIG. 18 is a drawing illustrating an example image displayed on the display unit 197. In FIG. 18, an image data G5 of the position of the puncture tip section 2 is displayed in addition to the images shown in FIG. 17. As described above, in the present embodiment, the image G5 of the current position of the puncture tip section 2 is displayed on the 3D model image G1 of the ilium. Thus, the operator can check the position of the puncture tip section 2 in the medullary cavity inside the ilium in which an ultrasound device is difficult to be used. Therefore, the operator can puncture the bone marrow in a desired trajectory with reference to this image. Moreover, as mentioned above, the image G4 of the predicted contacting position of the puncture tip section 2 with the cortical bone is also displayed on the 3D model image G1 of the ilium. Thus, the puncture tip section 2 can be prevented from contacting with the cortical bone.

In FIG. 18, images G6 showing past trajectories of the puncture tip section 2 are also displayed on the 3D model image G1 of the ilium. The analysis unit 195 sequentially stores the current position of the puncture tip section 2 and creates an image data of the past trajectory on the basis of the stored data. The analysis unit 195 outputs the created image data of the past trajectories to the display control unit 196, and the display control unit 196 displays images G6 of the past trajectories on the display unit 197. In an example shown in FIG. 18, three past trajectories are displayed as images G6. Therefore, the operator can decide a trajectory in which next puncturing is performed while checking the past trajectory. Thus, duplication of the bone marrow puncture site can be prevented.

FIG. 19 shows an example of showing the 3D model image G1 of the ilium displayed from the cross-sectional side indicated by an arrow Z1. As shown in FIG. 19, when the outer needle 32 of the guide tube 30 is inserted from each position at each angle as indicated by P1 and P2, an image G4 of each predicted contacting position of the puncture tip section 2 with the cortical bone is displayed. However, when the outer needle 32 of the guide tube 30 is inserted from a position at an angle as indicated by P3, an image of a contacting position of the puncture tip section 2 with the cortical bone is not displayed. This is because it is known that the length of the projection of the bone marrow puncture unit 1 shown in FIG. 1 or the like is L1, and the thickness and the like of the medullary cavity of the ilium can be calculated based on the 3D model. As described above, the bone marrow can be safely punctured in the present embodiment by selecting a trajectory in which an image of a predicted contacting position of the puncture tip section 2 with the cortical bone is not displayed.

The analysis unit 195 calculates a temporal change in position and angle data obtained by the first magnetic sensor 40 to calculate a moving rate of the puncture tip section 2. The analysis unit 195 outputs the data of the calculated moving rate to the display control unit 196, and the display control unit 196 displays the moving rate on the display unit 197. Thus, the operator can puncture the bone marrow while checking the moving rate of the puncture tip section 2. In order to satisfactorily maintain quality of collecting a bone marrow fluid, the puncture tip section 2 is required to move at an appropriate rate associated with the aspiration rate (aspiration pressure). In the present invention, the bone marrow can be punctured while checking the moving rate of the puncture tip section 2. The quality of collecting a bone marrow fluid can be maintained satisfactorily regardless of the operator. The moving rate of the puncture tip section 2 may be constant when the aspiration rate (aspiration pressure) is constant, and the moving rate may be changed in accordance with the change in aspiration rate (aspiration pressure).

The display control unit 196 is used as a moving rate notification unit in the present embodiment. However, the present invention is not limited to this aspect. For example, a control unit configured to control output of sound such as a buzzer may be used as the moving rate notification unit. In this case, an aspect in which a comparison unit (not shown) compares a predetermined moving rate associated with the aspiration rate (aspiration pressure) and the moving rate of the puncture tip section 2, and when the moving rate of the puncture tip section 2 is outside the appropriate rate range, outputting a sound such as a buzzer is output may be considered. In addition, displaying the moving rate is not limited to the case where a value of the moving rate is displayed directly, and an appropriate rate range may be displayed by an indicator or the like. Alternatively, some or all of these aspects may be combined as appropriate.

Moreover, when the moving rate of the puncture tip section 2 is out of the appropriate rate range, the PC 190 may send a feedback signal to the control unit 120 to stop driving of a motor in the bone marrow puncture device 10.

As described above, the past trajectory, the predicted trajectory, and the current position of the puncture tip section 2 are displayed on the 3D model image of the ilium in the present embodiment. Thus, the operator is prevented from moving the puncture tip section 2 to the same site as the site where collection of the bone marrow was once performed. Specifically, the operator can be notified of the past trajectory, the predicted trajectory, the current position of the puncture tip section 2 in the medullary cavity inside the bone such as the ilium in which an ultrasound device is difficult to be used. Therefore, the present invention is very effective in puncturing the bone marrow. Accordingly, the efficiency of collecting the bone marrow can be improved.

Specifically in the case where the bone marrow puncture unit 1 is inserted from the guide tube 30 that has been inserted into the same puncture hole (a hole made in the skin or the cortical bone), the bone marrow puncture unit 1 highly probably follows the past trajectory. Thus, the navigation according to the present embodiment is effective.

Further, when the current position or the predicted trajectory of the puncture tip section 2 is on or is near the recorded past trajectory, a warning such as a buzzer may be output. This can be achieved by, for example, outputting a warning when several consecutive points (e.g., five points) of the current position being sampled and monitored are on or near a certain past trajectory, or when the predicted trajectory or the predicted contacting position with cortical bone is on or near the past trajectory.

Moreover, duplication of the bone marrow collecting site can be reliably prevented in the present embodiment. Thus, a bone marrow fluid can be efficiently collected in a short time, and the bone marrow fluid with high quality can be collected, and the burden on the donor can be reduced.

Further, the bone marrow can be punctured while checking the moving rate of the puncture tip section 2. Thus, the quality of collecting a bone marrow fluid can be maintained satisfactorily regardless of the operator.

The present embodiment is described above with reference to the case where the bone marrow collecting site is the ilium. However, the present invention can be applied to sites other than the ilium in the same manner as mentioned above.

Moreover, for example, the control of the moving rate and the control from the past trajectory to another trajectory in the navigation can also be applied to other puncture devices that subject the body tissue to predetermined treatments while moving in the body. Examples of the predetermined treatments include collection and aspiration of the tissue, cauterization of the tissue, and supply of a drug solution and do not include simply taking an image that does not cause a change in the body tissue.

In the navigation mentioned above, the first magnetic sensor and the second magnetic sensor are used. The present invention, however, is not limited to this, and position monitoring by ultrasound or the like can be used. However, it is preferable to use the magnetic sensor in terms of miniaturization of the device and accuracy of position monitoring.

Although the embodiment of the present invention is described above, the present invention can be implemented in various aspects as described below. The present invention can also be implemented by combining the aspects.

For example, the present invention includes: a puncture tip section, a first tubular body connected to the puncture tip section at a distal end, and an outer tubular body at least partially covering the first tubular body, the first tubular body is formed to be rotatable around an axis along the longitudinal direction and has an outer diameter smaller than an inner diameter of the outer tubular body, and a drug solution supply path is provided on the outside of the first tubular body. In the present invention, the first tubular body has, for example, a communication portion communicating the drug solution supply path with a hollow portion (inner portion) of the first tubular body. The communication portion is formed on the puncture tip section side of the first tubular body, for example.

In the present invention, a drug solution is transferred to the outer surface of the first tubular body through the drug solution supply path provided on the outside of the first tubular body, for example. The drug solution transferred to the outer surface of the first tubular body is transferred to the puncture tip section side and mixed with the tissue collected with the puncture tip section, such as a bone marrow fluid. Moreover, the first tubular body has an outer diameter smaller than an inner diameter of the outer tubular body and is rotatable around an axis along the longitudinal direction. The drug solution transferred to the outer surface of the first tubular body is thus transferred to the puncture tip section side and mixed with a bone marrow fluid or the like immediately after collection by the puncture tip section through the rotation of the first tubular body. The bone marrow fluid or the like can be reliably prevented from coagulating when an anticoagulant is used as the drug solution, for example. The first tubular body that transfers a drug solution is, for example, placed in the outer tubular body, so that the aspiration path for the bone marrow fluid or the like can be sufficiently secured without unnecessarily enlarging the perforation hole (puncture hole) for collecting the bone marrow fluid or the like.

In another aspect of the present invention, the drug solution supply path is formed such that a cross section of a surface perpendicular to the longitudinal direction of the first tubular body is formed to have a circular shape, for example. The drug solution supply path is formed such that a cross section of a surface perpendicular to the longitudinal direction of the first tubular body has a circular shape, for example.

In this aspect, the drug solution supply path is formed such that a cross section of a surface perpendicular to the longitudinal direction of the first tubular body has a circular shape, for example. Thus, the drug solution is spread over the outer surface of the first tubular body and is reliably transferred to the puncture tip section side.

In yet another aspect of the present invention, the drug solution supply path includes a gap between an inner peripheral surface of the outer tubular body and an outer peripheral surface of the first tubular body, for example.

In this aspect, the drug solution supply path includes a gap between an inner peripheral surface of the outer tubular body and an outer peripheral surface of the first tubular body, for example. Thus, a tubular member for supplying a drug solution is not required to be disposed separately, and an increase in outer diameter of the outer tubular body can be prevented.

In yet another aspect of the present invention, the drug solution supply path is extended to the vicinity of the puncture tip section, for example.

In this aspect, the drug solution supply path is extended to the vicinity of the puncture tip section, for example. Thus, the drug solution is supplied in the vicinity of the puncture tip section and mixed with the bone marrow fluid or the like immediately after the collection.

In yet another aspect of the present invention, the first tubular body is rotatable inside the outer tubular body relative to the outside of the outer tubular body, for example.

In this aspect, the first tubular body is rotatable inside the outer tubular body relative to the outside of the outer tubular body, for example. Thus, the rotation torque is reliably propagated to the puncture tip section, and a drug solution supplied to the drug solution supply path can be transferred by the rotational force.

In yet another aspect of the present invention, a second tubular body as a rigid body is connected to a proximal end of the first tubular body, for example.

In this aspect, when a rotational force is applied to the rigid second tubular body, the rotational force is propagated to the first tubular body connected to the proximal end of the second tubular body and is further propagated to the puncture tip section connected to the first tubular body, for example. Moreover, by rotation of the first tubular body, a drug solution is transferred as mentioned above, for example.

In yet another aspect of the present invention, the outer tubular body at least partially covers the second tubular body, the second tubular body has an outer diameter smaller than an inner diameter of the outer tubular body and is rotatable inside the outer tubular body together with the first tubular body, and the drug solution supply path continues from a gap between the outer peripheral surface of the first tubular body and the inner peripheral surface of the outer tubular body to a gap between the outer peripheral surface of the second tubular body and the inner peripheral surface and the outer tubular body, for example.

In this aspect, the drug solution supply path is provided in a gap between the outer peripheral surface of the second tubular body and the inner peripheral surface of the outer tubular body and continues to a gap between the outer peripheral surface of the first tubular body and the inner peripheral surface of the outer tubular body, for example. Thus, when a drug solution is supplied to the outer peripheral surface of the second tubular body, the drug solution is reliably supplied to the outer surface of the first tubular body through the drug solution supply path.

In yet another aspect of the present invention, the first tubular body is formed into a coil shape, for example.

In this aspect, the first tubular body is formed into a coil shape, for example. Thus, the drug solution supplied to the outer surface of the first tubular body is freely permeable through the hollow portion of the first tubular body and is reliably transferred to the puncture tip section side with the rotation of the first tubular body. Further, the first tubular body is formed into a coil shape, and the rotation torque thus can be reliably propagated to the puncture tip section.

In yet another aspect of the present invention, a direction for winding the coiled first tubular body agrees with a direction for rotating the first tubular body, for example.

In this aspect, the direction for winding the coiled first tubular body agrees with a direction for rotating the first tubular body, for example. Thus, when the first tubular body is rotated, the coiled first tubular body is rotated in the direction for tightening, and the outer diameter of the first tubular body is not increased. Accordingly, the above-mentioned drug solution supply path is secured, and the first tubular body is smoothly rotated in the mantle (outer tubular body).

Yet another aspect of the present invention includes an aspiration device configured to perform aspiration in an inner space of the first tubular body, and the first tubular body is formed such that a drug solution in the drug solution supply path is permeable through the inner portion of the first tubular body, for example.

In this aspect, the bone marrow fluid or the like collected with the puncture tip section is aspirated from the inside of the first tubular body by the aspiration device, for example. At that time, the drug solution in the drug solution supply path is permeable through the inner portion of the first tubular body. Thus, the drug solution and the bone marrow fluid or the like are mixed.

In yet another aspect of the present invention, the aspiration device aspirates a bone marrow fluid, and the drug solution supply path supplies an anticoagulant, for example.

In this aspect, the bone marrow fluid collected with the puncture tip section is aspirated from the inner portion of the first tubular body with an aspiration device, for example. At that time, the anticoagulant supplied through the drug solution supply path is mixed with the bone marrow fluid. Accordingly, the collected bone marrow fluid is prevented from coagulating.

For example, the present invention includes, in a bone marrow puncture device with a tip that is at least inserted into a medullary cavity to collect a bone marrow fluid, a tubular body comprising a distal end and an opening in a surface at the distal end; a tip rotation section (e.g., the puncture tip section) that is configured to perforate (puncture) a tissue in a medullary cavity while rotating together with the tubular body and is disposed on a distal side of the surface at the distal end in the tubular body; and a connection member configured to connect the tubular body and the tip rotation section. For example, the bone marrow puncture instrument (bone marrow puncture device) according to the present invention includes: a tubular body comprising an opening, a tip rotation section that can perforate (puncture) a tissue in a medullary cavity while rotating together with the tubular body, and a connection member configured to connect the tubular body and the tip rotation section, and the tip rotation section, the connection member, and the tubular body are disposed in this order. The connection member is, for example, connected to a surface at the opening (surface at the distal end) on the periphery of the opening in the tubular body.

In the present invention, the tip rotation section rotating with the tubular body perforates (punctures) a tissue in the medullary cavity, and an opening is provided in the surface at the distal end of the tubular body connected from the tip rotation section with the connection member, for example. Thus, the bone marrow fluid can be efficiently aspirated from the tissue in the medullary cavity perforated (punctured) by the tip rotation section.

In yet another aspect of the present invention, the tubular body is formed integrally with the tip rotation section and the connection member and at least includes a tube having an opening and a flexible first tubular body disposed on proximal side of the tube, for example. In yet another aspect of the present invention, the tubular body includes a tube having an opening and a flexible first tubular body, the tube is formed integrally with the tip rotation section and the connection member, and the tip rotation section, the connection member, the tube, and the first tubular body are disposed in this order, for example.

In this aspect, the tubular body at least includes a flexible first tubular body and a tube having an opening, for example. Thus, even if the tip rotation section reaches the cortical bone, the tip rotation section does not damage the cortical bone because of the flexibility of the first tubular body.

In yet another aspect of the present invention, the tip rotation section includes a disc-shaped member having a radial central axis on a central axis extending in the longitudinal direction of the tubular body, for example.

In this aspect, the tip rotation section includes a disc-shaped member, for example. The tip is not sharp, the tip in the puncturing direction does not puncture (perforate) out of the medullary cavity from the inside, and the occurrence of a serious accident can be prevented. Moreover, the radial central axis of the disc-shaped member is present on the central axis extending in the longitudinal direction of the tubular body, for example. Thus, the disc-shaped member rotates around the central axis of the tubular body without being eccentric, and the rotation is smoothly performed, and the necessary minimum perforation hole (puncture hole) is formed.

In yet another aspect of the present invention, a groove continuing from the opening is formed in the connection member, for example.

In this aspect, in the connection member connecting between the tip rotation section and the tubular body having an opening, a groove continuing to the opening is formed, for example. Thus, the bone marrow perforated (punctured) by the tip rotation section can be efficiently transferred to the opening via the groove of the connection member.

In yet another aspect of the present invention, the surface at the distal end is not orthogonal to the longitudinal direction of the tubular body, for example.

In this aspect, the surface at the distal end is not orthogonal to the longitudinal direction of the tubular body, for example. The opening provided in the tubular body is larger than that provided in the surface at the distal end perpendicular to the longitudinal direction of the tubular body (for example, the opening). Accordingly, the bone marrow perforated (punctured) by the tip rotation section can be efficiently aspirated through the opening.

In yet another aspect of the present invention, the width of the tip rotation section in a direction orthogonal to the longitudinal direction of the tubular body is larger than that of the tube in the same, for example.

In this aspect, a perforation hole formed by rotating the tip rotation section is larger than the width of the tubular body in the direction orthogonal to the longitudinal direction of the tubular body, for example. Thus, the tubular body smoothly moves in the perforation hole (puncture hole) formed in the tip rotation section.

In yet another aspect of the present invention, by inserting the puncture tip section (e.g., tip rotation section) and the tubular body (e.g., the first tubular body, the second tubular body, and/or the outer tubular body (mantle)), a guide tube that guides the puncture tip section (e.g., tip rotation section) and the tubular body may be formed. The tubular body includes a flexible first tubular body and a rigid second tubular body, and the length of the second tubular body is that of the guide tube or less, for example. The puncture tip section, the first tubular body, and the second tubular body are disposed from the distal end toward the proximal end side in this order, for example. In the present invention, the puncturing direction of the puncture tip section and the tubular body can be controlled by the guide tube, for example.

A drive for the tubular body according to the present invention includes a holding member configured to hold the tubular body, a drive unit configured to rotate the tubular body, and a drug solution supply section configured to supply a drug solution to the tubular body, for example. The tubular body is, for example, the puncture instrument (puncture needle) or bone marrow puncture instrument (bone marrow puncture needle) according to the present invention.

In the present invention, the tubular body can be efficiently rotated, and the drug solution can be efficiently supplied, for example. The holding member, the drive unit, and the drug solution supply section may be disposed in the housing, for example.

In yet another aspect of the present invention, it is preferred that the tubular body includes a first drug solution supply path configured to lead a drug solution, and the drug solution supply section communicates with the first drug solution supply path of the tubular body, for example. The drug solution supply section includes a second drug solution supply path configured to lead a drug solution, the second drug solution supply path is a space between the inner peripheral surface of the holding member and the outer peripheral surface of the tubular body, and the second drug solution supply path communicates with the first drug solution supply path. In the present invention, the drug solution supplied from the outside of the drive can be efficiently supplied to the tubular body, for example.

In yet another aspect of the present invention, the tubular body includes a bearing for the tubular body, and the holding member holds the tubular body via the bearing, for example. Specifically, the bearing is disposed on the outer periphery of the tubular body, and the holding member is disposed on the outer periphery of the bearing, for example. The bearing includes a first bearing for the drag in the rotating direction (radial direction) and a second bearing for the drag in the propulsion direction (axial direction), for example. Yet another aspect of the present invention may include a protection member (e.g., protective sheath) for the tubular body, for example. In this case, the tubular body includes a bearing for the tubular body, and the holding member holds the tubular body via the bearing, for example. Specifically, the protection member is disposed on the outer periphery of the tubular body, the bearing is positioned on the outer periphery of the protection member, and the holding member is disposed on the outer periphery of the bearing. In the present invention, the drag generated at the time of driving the tubular body is absorbed by the drive, for example. Thus, the drive can be easily operated. Moreover, in the present invention, the tubular body can be prevented from being damaged during rotation, for example.

For example, the present invention includes: a puncture unit that includes a puncture tip section and a tubular body connected to the puncture tip section and is configured to subject a body tissue to a predetermined treatment while moving in a body; and a moving rate calculation unit configured to calculate a moving rate of the puncture unit.

In the present invention, for example, when a position of puncture unit moving in the body is changed, the moving rate of the puncture unit is calculated by the moving rate calculation unit. Thus, in the present invention, by referring to the calculated moving rate of the puncture unit, the moving rate of the puncture unit can be set to be in an appropriate range, and the quality of the treatment can be kept constant regardless of the experience of the operator, for example.

Yet another aspect of the present invention includes a comparison unit configured to compare the moving rate calculated by the moving rate calculation unit with a predetermined moving rate, for example.

In this aspect, the moving rate calculated by the comparison unit is compared with the predetermined moving rate, for example. Thus, by referring to the result of the comparison between the moving rate of the puncture unit and the predetermined moving rate, the moving rate of the puncture unit can be set in an appropriate range, and the quality of the treatment can be kept constant regardless of the experience of the operator.

Yet another aspect of the present invention includes a moving rate notification unit configured to notify the moving rate of puncture unit on the basis of a comparison result obtained by the comparison unit, for example.

In this aspect, information on the moving rate of the puncture unit based on the result of the comparison obtained by the comparison unit is notified by the notification unit, for example. Thus, the operator can know the information on the moving rate of the puncture unit relative to the predetermined moving rate. Accordingly, in this aspect, the moving rate of the puncture unit can be set in an appropriate range, and the quality of the treatment can be kept constant regardless of the experience of the operator, for example.

For example, the present invention includes: a puncture unit that includes a puncture tip section and a tubular body connected to the puncture tip section and subjects a body tissue to a predetermined treatment while moving in a body; a position calculation unit configured to calculate a position of the puncture tip section; and a recording unit configured to record a past trajectory of the puncture tip section.

In the present invention, when the position of the puncture unit moves in the body, the position calculation unit calculates the position of the puncture tip section, for example. Thus, in the present invention, duplication of the collecting site can be prevented, and the efficiency of the treatment can be improved on the basis of the calculated position of the puncture tip section, for example. Moreover, in the present invention, the recording unit records the past trajectory of the puncture tip section, for example. Thus, the operator can know the recorded past trajectory. Accordingly, duplication of the treating site can be prevented, and the efficiency of the treatment can be improved. Moreover, in the present invention, by the improvement of the efficiency of the treatment, the time required for the treatment can be shortened, for example.

Yet another aspect of the present invention includes a display control unit configured to successively display a position of the puncture tip section and the past trajectory recorded by the recording unit, for example.

In this aspect, the display control unit displays the recorded past trajectory, for example. Thus, the operator can check the current position of the puncture tip section while checking the past trajectory. Accordingly, in this aspect, duplication of the treating site is further effectively prevented, and the efficiency of the treatment can be improved, for example. Moreover, in this aspect, by the improvement of the efficiency of the treatment, the time required for the treatment can be shortened, for example.

Yet another aspect of the present invention includes a prediction unit configured to predict a trajectory of the puncture tip section, and the display control unit further displays the trajectory of the puncture tip section predicted by the prediction unit, for example. Yet another aspect of the present invention includes a prediction unit configured to predict a trajectory of the puncture tip section and the display control unit configured to display the trajectory of the puncture tip section predicted by the prediction, for example.

In this aspect, the trajectory of the puncture tip section is predicted by the prediction unit, for example. The display control unit displays the predicted trajectory of the puncture tip section, for example. Thus, the operator can move the puncture tip section into the body while checking the predicted trajectory of the puncture tip section, for example.

Thus, duplication of the treating site can be more effectively prevented, and the efficiency of the treatment can be improved. Moreover, in this aspect, by the improvement of the efficiency of the treatment, the time required for the treatment can be shortened, for example.

Yet another aspect of the present invention includes a notification unit configured to compare the moving trajectory of the puncture tip section and the past trajectory recorded by the recording unit and make a notification when the moving trajectory is substantially the same or the same as the past trajectory, for example.

In this aspect, the notification unit makes a notification that the moving trajectory of the puncture tip section and the past trajectory recorded are substantially the same or the same, for example. Thus, in this aspect, duplication of the treating site can be further effectively prevented, and the efficiency of the treatment can be improved, for example. Moreover, in this aspect, by the improvement of the efficiency of the treatment, the time required for the treatment can be shortened, for example.

Yet another aspect of the present invention includes a notification unit configured to compare the trajectory of the puncture tip section predicted by the prediction unit and the past trajectory recorded by the recording unit and make a notification when the predicted trajectory is substantially the same or the same as the past trajectory, for example.

In this aspect, the notification unit make a notification that the moving trajectory of the puncture tip section and the past trajectory recorded by the recording unit are substantially the same or the same, for example. Thus, in this aspect, duplication of the treating site can be further effectively prevented, and the efficiency of the treatment can be improved, for example. Moreover, in this aspect, by the improvement of the efficiency of the treatment, the time required for the treatment can be shortened, for example.

Yet another aspect of the present invention includes a first magnetic sensor attached to the puncture unit, for example.

Yet another aspect of the present invention includes a guide tube that guides the puncture unit by inserting the puncture unit; and a second magnetic sensor attached to the guide tube, for example.

The present invention includes: a bone marrow puncture unit that includes a puncture tip section and a tubular body connected to the puncture tip section and aspirates a bone marrow fluid while moving in a body; a guide tube configured to guides the bone marrow puncture unit, and a moving rate calculation unit configured to calculate a moving rate of the bone marrow puncture unit moving forward through the guide tube, for example.

In the present invention, for example, when a position of the bone marrow puncture unit moving in the body is changed, the moving rate of the bone marrow puncture unit is calculated by the moving rate calculation unit. Thus, in the present invention, by referring to the calculated moving rate of the bone marrow puncture unit, the moving rate of the bone marrow puncture unit can be set to be in an appropriate range, and the quality of the collection of the bone marrow can be kept constant regardless of the experience of the operator, for example.

Yet another aspect of the present invention includes a comparison unit configured to compare the moving rate calculated by the moving rate calculation unit and a predetermined moving rate associated with an aspiration rate of the bone marrow fluid, for example.

In this aspect, the comparison unit compares the calculated moving rate with a predetermined moving rate associated with the aspiration rate of the bone marrow fluid, for example. Thus, by referring to the result of comparison between the moving rate of the bone marrow puncture unit and the predetermined moving rate, the moving rate of the bone marrow puncture unit can be set to be in an appropriate range, and the quality of the collection of the bone marrow can be kept constant regardless of the experience of the operator, for example.

For example, the present invention includes: a bone marrow puncture unit that includes a puncture tip section and a tubular body connected to the puncture tip section and is configured to aspirate a bone marrow fluid while moving in the body; a guide tube configured to guide the puncture unit; a position calculation unit configured to calculate a position of the puncture tip section; and a recording unit configured to record a past trajectory of the puncture tip section.

In the present invention, when the position of the bone marrow puncture unit moving in the body is changed, the position calculation unit calculates the position of the puncture tip section, for example. Thus, in the present invention, duplication of the collecting site can be prevented, and the efficiency of collecting the bone marrow can be improved on the basis of the calculated position of the puncture tip section, for example. Moreover, in the present invention, the recording unit records the past trajectory of the puncture tip section, for example. Thus, the operator can know the recorded past trajectory. Accordingly, duplication of the bone marrow collecting site can be prevented, and the efficiency of the collection of the bone marrow can be improved. Moreover, in the present invention, by the improvement of the efficiency of collecting the bone marrow, the time required for the collection of the bone marrow can be shortened, for example.

Yet another aspect of the present invention includes a display control unit configured to successively display a position of the puncture tip section and the past trajectory recorded by the recording unit, for example.

In this aspect, the display control unit displays the recorded past trajectory, for example. Thus, the operator can check the current position of the puncture tip section while checking the past trajectory. Accordingly, in this aspect, duplication of the bone marrow collecting site can be further effectively prevented, and the efficiency of collecting the bone marrow can be improved, for example. Moreover, in this aspect, by the improvement of the efficiency of collecting the bone marrow, the time required for the collection of the bone marrow can be shortened, for example.

Yet another aspect of the present invention includes a prediction unit configured to predict a trajectory of the puncture tip section and a contacting position of the puncture tip section with a cortical bone, and the display control unit further displays the trajectory of the puncture tip section and the contacting position predicted by the prediction unit, for example. Yet another aspect of the present invention includes a prediction unit configured to predict a trajectory of the puncture tip section and a contacting position of the puncture tip section with a cortical bone and a display control unit configured to display the trajectory of the puncture tip section and the contacting position predicted by the prediction unit, for example.

In this aspect, the display control unit displays the recorded past trajectory, for example. Thus, the operator can check the current position of the puncture tip section while checking the past trajectory. Accordingly, in this aspect, duplication of the bone marrow collecting site can be further effectively prevented, and the efficiency of collecting the bone marrow can be improved, for example. Moreover, in this aspect, by the improvement of the efficiency of collecting the bone marrow, the time required for the collection of the bone marrow can be shortened, for example.

In yet another aspect of the present invention, the display control unit displays a past trajectory of the puncture tip section inserted from the same puncture hole into which the puncture instrument has been inserted once, for example. Yet another aspect of the present invention includes the display control unit configured to display a past trajectory of the puncture tip section inserted from the same puncture hole into which the puncture instrument has been inserted once, for example.

In this aspect, the display control unit displays the recorded past trajectory, for example. Thus, the operator can check the current position of the puncture tip section while checking the past trajectory. Accordingly, in this aspect, duplication of the bone marrow collecting site can be further effectively prevented, and the efficiency of collecting the bone marrow can be improved, for example. Moreover, in this aspect, by the improvement of the efficiency of collecting the bone marrow, the time required for the collection of the bone marrow can be shortened, for example.

Although the present invention is described above with reference to embodiments and various aspects, the present invention is not limited to the above-described embodiments and various aspects. Various modifications can be made within the scope of the present invention which can be understood by those skilled in the art.

(Supplementary Notes)

Some or all of the above-described embodiments and examples may be described as the following Supplementary Notes. However, the present invention is not limited by the Supplementary Notes.

(Supplementary Note 1)

A puncture instrument comprising:

a puncture tip section;

a first tubular body connected to the puncture tip section at a distal end, and an outer tubular body at least partially covering the first tubular body, wherein the first tubular body is formed to be rotatable around an axis along the longitudinal direction, the first tubular body has an outer diameter smaller than an inner diameter of the outer tubular body, and a drug solution supply path is provided on the outside of the first tubular body.

(Supplementary Note 2)

The puncture instrument according to Supplementary Note 1, wherein the drug solution supply path is formed such that a cross section of a surface perpendicular to the longitudinal direction of the first tubular body is formed to have a circular shape.

(Supplementary Note 3)

The puncture instrument according to Supplementary Note 1, wherein the drug solution supply path comprises a gap between an inner peripheral surface of the outer tubular body and an outer peripheral surface of the first tubular body.

(Supplementary Note 4)

The puncture instrument according to any one of Supplementary Notes 1 to 3, wherein the drug solution supply path is extended to the vicinity of the puncture tip section.

(Supplementary Note 5)

The puncture instrument according to any one of Supplementary Notes 1 to 4, wherein the first tubular body is rotatable inside the outer tubular body relative to the outside of the outer tubular body.

(Supplementary Note 6)

The puncture instrument according to any one of Supplementary Notes 1 to 5, wherein a second tubular body as a rigid body is connected to a proximal end of the first tubular body.

(Supplementary Note 7)

The puncture instrument according to Supplementary Note 6, wherein the outer tubular body at least partially covers the second tubular body, the second tubular body has an outer diameter smaller than an inner diameter of the outer tubular body and is rotatable inside the outer tubular body together with the first tubular body, and the drug solution supply path is provided in a gap between the outer peripheral surface of the first tubular body and the inner peripheral surface of the outer tubular body and continues to a gap between the outer peripheral surface of the second tubular body and the inner peripheral surface of the outer tubular body.

(Supplementary Note 8)

The puncture instrument according to any one of Supplementary Notes 1 to 7, wherein the first tubular body is formed into a coil shape.

(Supplementary Note 9)

The puncture instrument according to Supplementary Note 8, wherein a direction for winding the coiled first tubular body agrees with a direction for rotating the first tubular body.

(Supplementary Note 10)

The puncture instrument according to any one of Supplementary Notes 1 to 9, comprising an aspiration device configured to perform aspiration in an inner space of the first tubular body, wherein the first tubular body is formed such that a drug solution in the drug solution supply path is permeable through an inner portion of the first tubular body.

(Supplementary Note 11)

The puncture instrument according to Supplementary Note 10, wherein the aspiration device aspirates a bone marrow fluid, and the drug solution supply path supplies an anticoagulant.

(Supplementary Note 12)

The puncture instrument according to any one of Supplementary Notes 1 to 11, wherein the puncture tip section comprises:

a tube comprising a distal end and an opening in a surface at the distal end, a tip rotation section configured to perforate (puncture) a tissue in a medullary cavity while rotating together with the tube, the tip rotation section being disposed on a distal side of the surface at the distal end in the tube, and a connection member configured to connect the tube and the tip rotation section.

(Supplementary Note 13)

The puncture instrument according to Supplementary Note 12, wherein the tube comprising the opening is integrally formed with the tip rotation section and the connection member, and the first tubular body is flexible and is disposed on a proximal side of the tube.

(Supplementary Note 14)

The puncture instrument according to Supplementary Note 12 or 13, wherein the tip rotation section comprises a disc-shaped member having a radial central axis on a central axis extending in the longitudinal direction of the tube.

(Supplementary Note 15)

The puncture instrument according to any one of Supplementary Notes 12 to 14, wherein a groove continuing from the opening of the tube is formed in the connection member.

(Supplementary Note 16)

The puncture instrument according to any one of Supplementary Notes 12 to 15, wherein the surface at the distal end is not orthogonal to the longitudinal direction of the tube.

(Supplementary Note 17)

The puncture instrument according to any one of Supplementary Notes 12 to 16, wherein the width of the tip rotation section in a direction orthogonal to the longitudinal direction of the tube is large than that of the tube in the same.

(Supplementary Note 18)

The puncture instrument according to any one of Supplementary Notes 1 to 17, being a bone marrow puncture instrument.

(Supplementary Note 19)

A puncture device comprising:

the puncture instrument according to any one of Supplementary Notes 1 to 18; and a moving rate calculation unit configured to calculate a moving rate of the puncture instrument.

(Supplementary Note 20)

The puncture device according to Supplementary Note 19, comprising a comparison unit configured to compare the moving rate calculated by the moving rate calculation unit with a predetermined moving rate.

(Supplementary Note 21)

The puncture device according to Supplementary Note 20, comprising a moving rate notification unit configured to notify the moving rate of the puncture device on the basis of a comparison result obtained by the comparison unit.

(Supplementary Note 22)

The puncture device according to any one of Supplementary Notes 19 to 22, comprising a position calculation unit configured to calculate a position of the puncture tip section; and a recording unit configured to record a past trajectory of the puncture tip section.

(Supplementary Note 23)

The puncture device according to Supplementary Note 22, comprising a display control unit configured to successively display a position of the puncture tip section and the past trajectory recorded by the recording unit.

(Supplementary Note 24)

The puncture device according to Supplementary Note 23, comprising a prediction unit configured to predict a trajectory of the puncture tip section, wherein the display control unit further displays the trajectory of the puncture tip section predicted by the prediction unit.

(Supplementary Note 25)

The puncture device according to Supplementary Note 24, wherein a notification unit configured to compare the trajectory of the puncture tip section predicted by the prediction unit and the past trajectory recorded by the recording unit and make a notification when the predicted trajectory is substantially the same or the same as the past trajectory.

(Supplementary Note 26)

The puncture device according to any one of Supplementary Notes 22 to 25, comprising a notification unit configured to compare the moving trajectory in which the puncture tip section is moving and the past trajectory recorded by the recording unit and make a notification when the moving trajectory is substantially the same or the same as the past trajectory.

(Supplementary Note 27)

The puncture device according to any one of Supplementary Notes 19 to 26, comprising a first magnetic sensor attached to the puncture device.

(Supplementary Note 28)

The puncture device according to Supplementary Note 27, comprising a guide tube that guides the puncture device by inserting the puncture instrument according to any one of Supplementary Notes 1 to 18; and a second magnetic sensor attached to the guide tube.

(Supplementary Note 29)

A puncture device comprising:

the puncture instrument according to any one of Supplementary Notes 1 to 18;

a guide tube that guides the puncture instrument; and a moving rate calculation unit configured to calculate a moving rate of the puncture instrument moving forward through the guide tube.

(Supplementary Note 30)

The puncture device according to Supplementary Note 29, comprising a comparison unit configured to compare the moving rate calculated by the moving rate calculation unit and a predetermined moving rate associated with an aspiration rate of the bone marrow fluid.

(Supplementary Note 31)

A puncture device comprising:

the puncture instrument according to any one of Supplementary Notes 1 to 18;

a guide tube that guides the puncture instrument;

a position calculation unit configured to calculate a position of the puncture tip section; and a recording unit configured to record a past trajectory of the puncture tip section.

(Supplementary Note 32)

The puncture device according to Supplementary Note 31, comprising a display control unit configured to successively display a position of the puncture tip section and the past trajectory recorded by the recording unit.

(Supplementary Note 33)

The puncture device according to Supplementary Note 32, comprising a prediction unit configured to predict a trajectory of the puncture tip section and a contacting position of the puncture tip section with a cortical bone, wherein the display control unit further displays the trajectory of the puncture tip section and the contacting position predicted by the prediction unit.

(Supplementary Note 34)

The puncture device according to any one of Supplementary Notes 31 to 33, wherein the display control unit displays a past trajectory of the puncture tip section inserted from the same puncture hole into which the puncture instrument has been inserted once.

(Supplementary Note 35)

A puncture instrument comprising, in a bone marrow puncture device with a tip that is at least inserted into a medullary cavity to collect a bone marrow fluid, a tubular body comprising a distal end and an opening in a surface at the distal end, a tip rotation section configured to perforate (puncture) a tissue in a medullary cavity while rotating together with the tubular body, the tip rotation section being disposed on a distal side of the surface at the distal end in the tubular body, and a connection member configured to connect the tubular body and the tip rotation section.

(Supplementary Note 36)

The puncture instrument according to Supplementary Note 35, wherein the tubular body comprises:

a tube that is integrally formed with the tip rotation section and the connection member and has the opening; and a flexible first tubular body disposed on an proximal side of the tube.

(Supplementary Note 37)

The puncture instrument according to Supplementary Note 35 or 36, wherein the tip rotation section comprises a disc-shaped member having a radial central axis on a central axis extending in the longitudinal direction of the tubular body.

(Supplementary Note 38)

The puncture instrument according to any one of Supplementary Notes 35 to 37, wherein a groove continuing from the opening of the tube is formed in the connection member.

(Supplementary Note 39)

The puncture instrument according to any one of Supplementary Notes 35 to 38, wherein the surface at the distal end is not orthogonal to the longitudinal direction of the tubular body.

(Supplementary Note 40)

The puncture instrument according to any one of Supplementary Notes 35 to 39, wherein the width of the tip rotation section in a direction orthogonal to the longitudinal direction of the tubular body is larger than that of the tubular body in the same.

(Supplementary Note 41)

The puncture instrument according to any one of Supplementary Notes 35 to 40, being a bone marrow puncture instrument.

(Supplementary Note 42)

A puncture device comprising:

the puncture instrument according to any one of Supplementary Notes 35 to 41; and a moving rate calculation unit configured to calculate a moving rate of the puncture instrument.

(Supplementary Note 43)

The puncture device according to Supplementary Note 42, comprising a comparison unit configured to compare the moving rate calculated by the moving rate calculation unit with a predetermined moving rate.

(Supplementary Note 44)

The puncture device according to Supplementary Note 43, comprising a moving rate notification unit configured to notify the moving rate of the puncture unit on the basis of a comparison result obtained by the comparison unit.

(Supplementary Note 45)

A puncture device comprising:

the puncture instrument according to any one of Supplementary Notes 35 to 41;

a position calculation unit configured to calculate a position of the puncture tip section; and a recording unit configured to record a past trajectory of the puncture tip section.

(Supplementary Note 46)

The puncture device according to Supplementary Note 45, comprising a display control unit configured to successively display a position of the puncture tip section and the past trajectory recorded by the recording unit.

(Supplementary Note 47)

The puncture device according to Supplementary Note 46, comprising a prediction unit configured to predict a trajectory of the puncture tip section, wherein the display control unit further displays the trajectory of the puncture tip section predicted by the prediction unit.

(Supplementary Note 48)

The puncture device according to Supplementary Note 47, comprising a notification unit configured to compare the trajectory of the puncture tip section predicted by the prediction unit and the past trajectory recorded by the recording unit and make a notification when the predicted trajectory is substantially the same or the same as the past trajectory.

(Supplementary Note 49)

The puncture device according to any one of Supplementary Notes 45 to 48, comprising a notification unit configured to compare the moving trajectory in which the puncture tip section is moving and the past trajectory recorded by the recording unit and make a notification when the moving trajectory is substantially the same or the same as the past trajectory.

(Supplementary Note 50)

The puncture device according to any one of Supplementary Notes 42 to 49, comprising a first magnetic sensor attached to the puncture unit.

(Supplementary Note 51)

The puncture device according to Supplementary Note 50, comprising:

a guide tube that guides the puncture unit by inserting the puncture unit; and a second magnetic sensor attached to the guide tube.

(Supplementary Note 52)

A puncture device comprising:

the puncture instrument according to any one of Supplementary Notes 35 to 41;

a guide tube that guides the bone marrow puncture unit; and a moving rate calculation unit configured to calculate a moving rate of the bone marrow puncture unit moving forward through the guide tube.

(Supplementary Note 53)

The puncture device according to Supplementary Note 52, comprising a comparison unit configured to compare the moving rate calculated by the moving rate calculation unit and a predetermined moving rate associated with an aspiration rate of the bone marrow fluid.

(Supplementary Note 54)

A puncture device comprising:

the puncture instrument according to any one of Supplementary Notes 35 to 41; and a guide tube that guides the puncture unit;

a position calculation unit configured to calculate a position of the puncture tip section; and a recording unit configured to record a past trajectory of the puncture tip section.

(Supplementary Note 55)

The puncture device according to Supplementary Note 54, comprising a display control unit configured to successively display a position of the puncture tip section and the past trajectory recorded by the recording unit.

(Supplementary Note 56)

The puncture device according to Supplementary Note 55, comprising a prediction unit configured to predict a trajectory of the puncture tip section and a contacting position of the puncture tip section with a cortical bone, wherein the display control unit further displays the trajectory of the puncture tip section and the contacting position predicted by the prediction unit.

(Supplementary Note 57)

The puncture device according to Supplementary Note 55 or 56, wherein the display control unit displays a past trajectory of the puncture tip section inserted from the same puncture hole into which the puncture instrument has been inserted once.

(Supplementary Note 58)

A puncture device comprising:

a puncture unit comprising a puncture tip section and a tubular body connected to the puncture tip section, the puncture unit being configured to subject a body tissue to a predetermined treatment while moving in a body; and a moving rate calculation unit configured to calculate a moving rate of the puncture unit.

(Supplementary Note 59)

The puncture device according to Supplementary Note 58, comprising a comparison unit configured to compare the moving rate calculated by the moving rate calculation unit with a predetermined moving rate.

(Supplementary Note 60)

The puncture device according to Supplementary Note 60, comprising a moving rate notification unit configured to notify the moving rate of the puncture unit on the basis of a comparison result obtained by the comparison unit.

(Supplementary Note 61)

A puncture device comprising:

a puncture unit comprising a puncture tip section and a tubular body connected to the puncture tip section, the puncture unit being configured to subject a body tissue to a predetermined treatment while moving in a body;

a position calculation unit configured to calculate a position of the puncture tip section; and a recording unit configured to record a past trajectory of the puncture tip section.

(Supplementary Note 62)

A puncture device according to Supplementary Note 61, comprising a display control unit configured to successively display a position of the puncture tip section and the past trajectory recorded by the recording unit.

(Supplementary Note 63)

The puncture device according to Supplementary Note 62, comprising a prediction unit configured to predict a trajectory of the puncture tip section, wherein the display control unit further displays the trajectory of the puncture tip section predicted by the prediction unit.

(Supplementary Note 64)

The puncture device according to Supplementary Note 63, comprising a notification unit configured to compare the trajectory of the puncture tip section predicted by the prediction unit and the past trajectory recorded by the recording unit and make a notification when the predicted trajectory is substantially the same or the same as the past trajectory.

(Supplementary Note 65)

The puncture device according to any one of Supplementary Notes 61 to 64, comprising a notification unit configured to compare the moving trajectory in which the puncture tip section is moving and the past trajectory recorded by the recording unit and make a notification when the moving trajectory is substantially the same or the same as the past trajectory.
(Supplementary Note 66)

The puncture device according to any one of Supplementary Notes 58 to 65, comprising a first magnetic sensor attached to the puncture unit.
(Supplementary Note 67)

The puncture device according to Supplementary Note 66, comprising
a guide tube that guides the puncture unit by inserting the puncture unit; and
a second magnetic sensor attached to the guide tube.
(Supplementary Note 68)

A puncture device comprising:
a bone marrow puncture unit comprising a puncture tip section, a tubular body connected to the puncture tip section, the bone marrow puncture unit being configured to aspirate a bone marrow fluid while moving in a body;
a guide tube that guides the bone marrow puncture unit; and
a moving rate calculation unit configured to calculate a moving rate of the bone marrow puncture unit moving forward through the guide tube.
(Supplementary Note 69)

The puncture device according to Supplementary Note 68, further comprising a comparison unit configured to compare the moving rate calculated by the moving rate calculation unit and a predetermined moving rate associated with an aspiration rate of the bone marrow fluid.
(Supplementary Note 70)

A puncture device comprising:
a bone marrow puncture unit comprising a puncture tip section, a tubular body connected to the puncture tip section, the bone marrow puncture unit being configured to aspirate a bone marrow fluid while moving in a body;
a guide tube that guides the puncture unit;
a position calculation unit configured to calculate a position of the puncture tip section; and
a recording unit configured to record a past trajectory of the puncture tip section.
(Supplementary Note 71)

The puncture device according to Supplementary Note 70, comprising a display control unit configured to successively display a position of the puncture tip section and the past trajectory recorded by the recording unit.
(Supplementary Note 72)

The puncture device according to Supplementary Note 71, comprising
a prediction unit configured to predict a trajectory of the puncture tip section and a contacting position of the puncture tip section with a cortical bone, wherein
the display control unit further displays the trajectory of the puncture tip section and the contacting position predicted by the prediction unit.
(Supplementary Note 73)

The puncture device according to Supplementary Note 71 or 72, wherein
the display control unit displays a past trajectory of the puncture tip section inserted from a puncture hole that is the same as a puncture hole into which the puncture unit has been inserted.

This application is based upon and claims the benefit of priority from Japanese patent application Nos. 2017-015764, 2017-015767, and 2017-015795, filed on Jan. 31, 2017, the disclosure of which is incorporated herein its entirety by reference.

INDUSTRIAL APPLICABILITY

As described above, with the first puncture instrument or puncture device according to the present invention, a drug solution can be administered. Moreover, with the first puncture instrument or puncture device according to the present invention, the bone marrow fluid or the like can be reliably prevented from coagulating when an anticoagulant is used as the drug solution, for example. Furthermore, in the first puncture instrument or puncture device according to the present invention, the first tubular body that transfers a drug solution is, for example, placed in the outer tubular body. Thus, the aspiration path for the bone marrow fluid or the like can be sufficiently secured without unnecessarily enlarging a perforation hole for collecting the bone marrow fluid or the like. The present invention is therefore really useful in, for example, technique in the medical field of transplantation medicine or regeneration medicine.

REFERENCE SIGNS LIST

1: bone marrow puncture unit
2: puncture tip section
3: first tubular body
4: second tubular body
5: mantle
5a: drug solution supply path
10: bone marrow puncture device
20: tube
20a: end surface
20b: opening
21: disc-shaped member
22: connection member
30: guide tube
40: first magnetic sensor
41: second magnetic sensor
100: bone marrow puncture system
160: tracking unit
195: analysis unit
196: display control unit
197: display unit

The invention claimed is:

1. A puncture instrument configured for use in a bone marrow puncture device with a tip that is at least inserted into a medullary cavity to collect a bone marrow fluid, the puncture instrument comprising:
a tubular body,
a tip rotation section, and
a connection member, wherein
the tubular body comprises
a distal end, and
an opening in a surface at the distal end,
the tip rotation section is configured to puncture a tissue in a medullary cavity while rotating together with the tubular body, and disposed on a distal side of the surface at the distal end in the tubular body, and
the connection member is configured to connect the tubular body and the tip rotation section.

2. The puncture instrument according to claim 1, wherein the tubular body comprises:
a tube that is integrally formed with the tip rotation section and the connection member and has the opening; and a flexible first tubular body disposed on a proximal side of the tube.

3. The puncture instrument according to claim 2, wherein the flexible first tubular body is formed into a coil shape.

4. The puncture instrument according to claim 3, wherein a direction for winding the coiled first tubular body corresponds to a direction for rotating the first tubular body.

5. The puncture instrument according to claim 1, wherein the tip rotation section comprises a disc-shaped member having a radial central axis on a central axis extending in the longitudinal direction of the tubular body.

6. The puncture instrument according to claim 1, wherein a groove continuing from the opening is formed in the connection member.

7. The puncture instrument according to claim 1, wherein the surface at the distal end is not orthogonal to the longitudinal direction of the tubular body.

8. The puncture instrument according to claim 1, wherein the width of the tip rotation section in a direction orthogonal to the longitudinal direction of the tubular body is larger than that of the tubular body in the same.

9. The puncture instrument according to claim 1, wherein an angle $\theta$ between a surface at the distal end of the tubular body and a central axis extending in the longitudinal direction of the tubular body is an acute angle.

10. The puncture instrument according to claim 9, wherein the angle $\theta$ is 50° to 60°.

11. The puncture instrument according to claim 1, wherein an outer edge of the tip rotation section at the distal side is an arc shape.

12. The puncture instrument according to claim 1, wherein a side surface at an outer edge of the tip rotation section is a curved surface.

* * * * *